US011408889B2

(12) United States Patent
Wang et al.

(10) Patent No.: US 11,408,889 B2
(45) **Date of Patent: *Aug. 9, 2022**

(54) ANTI-GITR ANTIBODIES FOR CANCER DIAGNOSTICS

(71) Applicant: BRISTOL-MYERS SQUIBB COMPANY, Princeton, NJ (US)

(72) Inventors: Xi-Tao Wang, Wellesley, MA (US); Olufemi A. Adelakun, Kendall Park, NJ (US); Anne C. Lewin, Lawrenceville, NJ (US); Alan J. Korman, Piedmont, CA (US); Mark J. Selby, San Francisco, CA (US); Changyu Wang, Union City, CA (US); Haichun Huang, Fremont, CA (US); Karla A. Henning, Milpitas, CA (US); Nils Lonberg, Woodside, CA (US); Mohan Srinivasan, Cupertino, CA (US); Michelle Minhua Han, Piedmont, CA (US); Guodong Chen, East Brunswick, NJ (US); Richard Y. Huang, Bridgewater, NJ (US); Indrani Chakraborty, Fremont, CA (US); Susan Chien-Szu Wong, Fremont, CA (US); Huiming Li, Lexington, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/870,006

(22) Filed: May 8, 2020

(65) Prior Publication Data

US 2021/0011022 A1 Jan. 14, 2021

Related U.S. Application Data

(63) Continuation of application No. 15/578,874, filed as application No. PCT/US2016/035514 on Jun. 2, 2016, now Pat. No. 10,690,674.

(60) Provisional application No. 62/170,579, filed on Jun. 3, 2015.

(51) Int. Cl.

*G01N 33/566* (2006.01)
*G01N 33/574* (2006.01)
*C07K 16/28* (2006.01)

(52) U.S. Cl.

CPC ... *G01N 33/57492* (2013.01); *C07K 16/2866* (2013.01); *C07K 16/2878* (2013.01); *G01N 33/566* (2013.01); *C07K 2317/21* (2013.01); *C07K 2317/24* (2013.01); *C07K 2317/56* (2013.01); *C07K 2317/92* (2013.01); *G01N 2333/4703* (2013.01); *G01N 2333/7051* (2013.01); *G01N 2333/70578* (2013.01); *G01N 2333/7151* (2013.01); *G01N 2800/52* (2013.01); *G01N 2800/7028* (2013.01)

(58) Field of Classification Search

CPC ............ G01N 33/57492
USPC ............ 424/173.1
See application file for complete search history.

(56) References Cited

U.S. PATENT DOCUMENTS

| | | | |
|---|---|---|---|
| 5,624,821 | A | 4/1997 | Winter et al. |
| 5,648,260 | A | 7/1997 | Winter et al. |
| 6,111,090 | A | 8/2000 | Gorman et al. |
| 6,509,173 | B1 | 1/2003 | Ni et al. |
| 7,025,962 | B1 | 4/2006 | Gorman et al. |
| 7,247,302 | B1 | 7/2007 | Rosok et al. |
| 7,812,135 | B2 | 10/2010 | Smith et al. |
| 8,709,424 | B2 | 4/2014 | Schebye et al. |
| 9,228,016 | B2 | 1/2016 | Wang et al. |
| 9,745,379 | B2 | 8/2017 | Wang et al. |
| 10,465,010 | B2 | 11/2019 | Wang et al. |
| 10,501,550 | B2 | 12/2019 | Wang et al. |
| 10,690,674 | B2 | 6/2020 | Wang et al. |
| 11,084,881 | B2 | 8/2021 | Wang et al. |
| 11,213,586 | B2 | 1/2022 | Wang et al. |
| 2002/0081597 | A1 | 6/2002 | Lowe et al. |
| 2006/0099171 | A1 | 5/2006 | Tone et al. |
| 2006/0281146 | A1 | 12/2006 | Bodary et al. |
| 2006/0286112 | A1 | 12/2006 | Kellermann et al. |

(Continued)

FOREIGN PATENT DOCUMENTS

| | | | |
|---|---|---|---|
| EP | 0920505 | B1 | 6/2008 |
| EP | 2343320 | A1 | 7/2011 |

(Continued)

OTHER PUBLICATIONS

An Investigational Immuno-therapy Study of Experimental Medication BMS-986156, Given by Itself or in Combination With Nivolumab in Patients With Solid Cancers or Cancers That Have Spread, ClinicalTrials.gov Identifier: NCT02598960, date first posted: Nov. 6, 2015, dated last updated: Feb. 1, 2018, 7 pages, date retrieved: Feb. 14, 2018 <https://clinicaltrials.gov/ct2/show/NCT02598960?term=BMS-986156&rank=1>.

(Continued)

*Primary Examiner* — Sean E Aeder
(74) *Attorney, Agent, or Firm* — Nelson Mullins Riley & Scarborough LLP; Jane E. Remillard, Esq.; Christopher L. Frank

(57) ABSTRACT

Provided herein are diagnostic antibodies that bind to glucocorticoid-induced tumor necrosis factor receptor (GITR). Such antibodies are useful for methods of detecting the expression of GITR in biological samples, for example, tumor tissue, and identifying a cancer patient likely to respond to anti-GITR immunotherapy or predicting whether a cancer patient will respond to anti-GITR immunotherapy.

20 Claims, 10 Drawing Sheets

Specification includes a Sequence Listing.

(56) References Cited

U.S. PATENT DOCUMENTS

| | | | |
|---|---|---|---|
| 2007/0037148 | A1 | 2/2007 | Fong et al. |
| 2007/0048301 | A1 | 3/2007 | Bodary-Winter et al. |
| 2007/0098719 | A1 | 5/2007 | Smith et al. |
| 2007/0185017 | A1 | 8/2007 | Aggarwal et al. |
| 2012/0328616 | A1 | 12/2012 | Li et al. |
| 2014/0065152 | A1 | 3/2014 | Kwon |
| 2015/0064204 | A1 | 3/2015 | Beers et al. |
| 2015/0073043 | A1 | 3/2015 | Li et al. |
| 2015/0353637 | A1 | 12/2015 | Wang et al. |
| 2016/0145342 | A1 | 5/2016 | Wang et al. |
| 2017/0145104 | A1 | 5/2017 | Wang et al. |
| 2018/0002432 | A1 | 1/2018 | Wang et al. |
| 2018/0164321 | A1 | 6/2018 | Wang et al. |
| 2018/0339042 | A1 | 11/2018 | Wang et al. |
| 2020/0079865 | A1 | 3/2020 | Wang et al. |
| 2020/0115463 | A1 | 4/2020 | Wang et al. |
| 2020/0291122 | A1 | 9/2020 | Krishnan et al. |

FOREIGN PATENT DOCUMENTS

| | | | |
|---|---|---|---|
| EP | 2481752 | A1 | 8/2012 |
| JP | 2008 278814 | A | 11/2008 |
| KR | 20080105674 | A | 12/2008 |
| WO | 98/06842 | A1 | 2/1998 |
| WO | 98/24895 | A1 | 6/1998 |
| WO | 99/20758 | A1 | 4/1999 |
| WO | 99/25834 | A1 | 5/1999 |
| WO | 99/40196 | A1 | 8/1999 |
| WO | 00/05374 | A2 | 2/2000 |
| WO | 00/32221 | A2 | 6/2000 |
| WO | 00/32778 | A2 | 6/2000 |
| WO | 00/50459 | A1 | 8/2000 |
| WO | 2001003720 | A2 | 1/2001 |
| WO | 2001/46232 | A2 | 6/2001 |
| WO | 2001/46261 | A1 | 6/2001 |
| WO | 2001040464 | A1 | 6/2001 |
| WO | 2001/90304 | A2 | 11/2001 |
| WO | 2002/22153 | A2 | 3/2002 |
| WO | 2002/072607 | A2 | 9/2002 |
| WO | 2003/006058 | A1 | 1/2003 |
| WO | 2003068257 | A1 | 8/2003 |
| WO | 2004/107618 | A2 | 12/2004 |
| WO | 2005/007190 | A1 | 1/2005 |
| WO | 2005/007699 | A2 | 1/2005 |
| WO | 2005/016962 | A2 | 2/2005 |
| WO | 2005/019258 | A2 | 3/2005 |
| WO | 2005/052000 | A2 | 6/2005 |
| WO | 2005/052001 | A2 | 6/2005 |
| WO | 2005/100402 | A1 | 10/2005 |
| WO | 2006050172 | A2 | 5/2006 |
| WO | 06/078911 | A2 | 7/2006 |
| WO | 2006/105021 | A2 | 10/2006 |
| WO | 2006/124269 | A2 | 11/2006 |
| WO | 2006/132272 | A1 | 12/2006 |
| WO | 2007/002223 | A2 | 1/2007 |
| WO | 2007120368 | A2 | 10/2007 |
| WO | 2007/133822 | A1 | 11/2007 |
| WO | 2008/070593 | A2 | 6/2008 |
| WO | 2009/009116 | A2 | 1/2009 |
| WO | 2009/100309 | A2 | 8/2009 |
| WO | 2009/120922 | A2 | 10/2009 |
| WO | 2011/028683 | A1 | 3/2011 |
| WO | 2011109789 | A2 | 9/2011 |
| WO | 2011/120134 | A1 | 10/2011 |
| WO | 2012016227 | A2 | 2/2012 |
| WO | 2012087928 | A2 | 6/2012 |
| WO | 2012/098113 | A1 | 7/2012 |
| WO | 2013/039954 | A1 | 3/2013 |
| WO | 2013/043569 | A1 | 3/2013 |
| WO | 2013/177101 | A2 | 11/2013 |
| WO | 2014/089113 | A1 | 6/2014 |
| WO | 2015026684 | A1 | 2/2015 |
| WO | 2015/145360 | A1 | 10/2015 |
| WO | 2015/184099 | A1 | 12/2015 |
| WO | 2015/187835 | A2 | 12/2015 |
| WO | 2016054638 | A1 | 4/2016 |
| WO | 2016/196792 | A1 | 12/2016 |

OTHER PUBLICATIONS

Arnett, S. et al., "IBC's 21st Annual Antibody Engineering and 8th Annual Antibody Therapeutics International Conferences and 2010 Annual Meeting of the Antibody Society," Dec. 5-9, 2010, San Diego, CA USA, mAbs, vol. 3(2), Mar./Apr. 2011, 133-152.

Avogadri, F. et al., "Modulation of CTLA-4 and GITR for Cancer Immunotherapy," Curr Top Microbiol Immunol, vol. 344: 211-244 (2011).

Baecher-Allan, B. et al., "Inhibition of Human CD4+CD25+ high Regulatory T Cell Function," J. Immunol., vol. 169, 3210-6217 (2002).

Balint, R. et al., "Antibody Engineering by Parsimonious Mutagenesis," Gene, vol. 137: 109-118 (1993).

Barrios, Y. et al., "Length of the antibody heavy chain complementarity determining region 3 as a specificity determining factor," J Molecular Recognition, vol. 17: 332-338 (2004).

Birebent, B. et al., "Suppressive properties of human CD4+CD25+ regulatory T cells are dependent on CTLA-4 expression," Eur. J. Immunol., vol. 34:3485-3496 (2004).

Bulliard, et al., "Activating Fc y receptors contribute to the antitumor activities of immunoregulatory receptor-targeting antibodies," JEM, vol. 210 (9): 1685-1693 (2013).

Bulliard, et al., "Activating Fc y receptors contribute to the antitumor activities of immunoregulatory receptortargeting antibodies," Novartis Institutes for Biomedical Research and Dana Farber Cancer Institutes USA, No date, 1-3.

Carter et al., "Humanization of an anti-p185HER2 antibody for human cancer therapy," PNAS, vol. 89, 4285-4289 (1992).

Coe, D. et al., "Depletion of regulatory T cells by anti-GITR mAb as a novel mechanism for cancer immunotherapy," Cancer Immunol Immunother, vol. 59, 1367-1377 (2010).

Cohen et al., "Synergistic Tumor Immunity Induced by Chemotherapy and Agonist Anti-GITR Antibody," Blood, ASH Annual Meeting Abstracts, Dec. 8-11, 2007, vol. 110 (11), 1788.

Cohen, et al., "Agonist Anti-GITR Antibody Enhances Vaccine-Induced CD8+ T-Cell Responses and Tumor Immunity," Cancer Res., vol. 66: (9):4904-4912 (2006).

Davies et al., "Affinity improvement of single antibody VH domains: residues in all three hypervanable regions affect antigen bnding," Immunotechnology, vol. 2, 169-179 (1996).

Dittmer et al., "Functional impairment of CD8+ T cellls by regulatory T cells during persistent retroviral infection," Immunity, vol. 20, 293-303 (2004).

Glaus et al., "In vivo SPECT/CT imaging of an anti-GITR antibody: A novel cancer immunotherapeutic," J Nucl Med., vol. 54 (Supplement 2):327 (2013).

Godrey et al., "Cord blood CD4+ CD25+-derived T regulatory cell lines express FoxP3 protein and manifest potent suppressor function," Blood, vol. 105 No. 2, 750-758 (2005).

Gross et al., "TACI-lg Neutralizes Molecules Critical for B Cell Development and Autoimmune Disease: Impaired B Cell Maturation in Mice Lacking BLyS," Immunity, vol. 15:289-302 (2001).

Gurney et al., "Identification of a new member of the tumor necrosis factor family and its receptor, a human ortholog of mouse GITR," Current Biology, vol. 9 (4), 215-218 (1999).

Hawkins, R.E. et al., "Selection of Phage Antibodies by Binding Affinity Mimicking Affinity Maturation," J. Mol. Biol., vol. 226(3): 889-896 (1992).

Hiroyoshi Nishikawa, "Application of Modulators of Cancer Immunosuppression for Immunotherapy—GITR and CTLA-4," The Medical Frontline, vol. 64 (11): 100-105 (2009).

Holt, L. et al., "Domain antibodies: proteins for therapy," Trends in Biotechnology, vol. 21 (11): 484-490 (2003).

Houot et al., "T-cell modulation combined with intratumoral CpG cures lymphoma in a mouse model without the need or chemotherapy," Blood, vol. 113 (15):3546-3552 (2009).

(56) References Cited

OTHER PUBLICATIONS

International Preliminary Reporton Patentability, PCT/US2015/033991, dated Dec. 6, 2016, 11 pages.
International Preliminary Report on Patentability, PCT/US2016/062540, dated May 22, 2018, 17 pages.
International Search Report and Written Opinion, PCT/US2015/033991, dated Dec. 8, 2015,17 pages.
International Search Report and Written Opinion, PCT/US2016/062540, dated Jun. 26, 2017, 26 pages.
Invitation to Pay Additional Fees and, Where Applicable, Protest Fees, PCT/US2016/062540, dated May 3, 2017, 25 pages.
Kanamaru et al., "Costimulation via Glucocorticoid-Induced TNF Receptor in Both Conventional and CD25+ Regulatory CD4+ T Cells," The Journal of Immunology, 7306-7314 (2004).
Kim et al., "Fcy receptors enable anticancer action of proapoptotic and immune-modulatory antibodies," J Exp Med., vol. 210 (9) 1647-1651 (2013).
Ko et al., "A Combination of Chemoimmunotherapies Can Efficiently Break Self-Tolerance and Induce Antitumor Immunity in a Tolerogenic Murine Tumor Model," Cancer Research, vol. 67 (15) 7477-7486 (2007).
Ko et al., "Treatment of advanced tumors with agonistic anti-GITR mAb and its effects on tumor-infiltrating Foxp3+ CD25+ CD4+ regulatory T cells," JEM, vol. 202 (7), 885-891 (2005).
Kuenen, B. et al., "A phase I pharmacologic study of necitumumab (IMC-11F8), a fully human IgG1 monoclonal antibody directed against EGFR in patients with advanced solid malignancies," Clin Cancer Res., vol. 16(6): 1915-1923 (2010).
Kwon et al., "Identification of a Novel Activation-inducible Protein of the Tumor Necrosis Factor Receptor Superfamily and Its Ligand," Journal of Biol Chem, vol. 274 (10) 6056-6061 (1999).
Little et al., "Of Mice and Men: hybridoma and recombinant antibodies," Immunology Today, vol. 21(8): 364-370 (2000).
Lu et al. "Combined PD-1 blockade and GITR triggering induce a potent antitumor immunity in murine cancer models and synergizes with chemotherapeutic drugs," Journal of Translational Medicine, vol. 12 (36), 1-11 (2014).
Marks, J. et al, "By-Passing Immunization: Building High Affinity Human Antibodies By Chain Shuffling," Biotechnology, vol. 10(7): 779-783 (1992).
McHugh et al., "CD4+CD25+ Immunoregulatory T Cells: Gene Expression Analysis Reveals a Functional Role for the Glucocorticoid-Induced TNF Receptor," Immunity, vol. 16, 311-323 (2002).
Melero et al., "Agonist Antibodies to TNFR Molecules That Costimulate Tand NK Cells," Clinical Cancer Research, vol. 19 (5): 1044-1053, 1913 (2013).
Melero et al., "Clinical Development of Immunostimulatory Monoclonal Antibodies and Opportunities for Combination," Clinical Cancer Research, vol. 19(5), 997-1008 (2013).
Melero, I., "Immunological targets: Basic aspects," IL29, Annals of Oncology, vol. 22 (Supplement 3), 1 page, (2011) doi:10.1093/annonc/mdr103.
Mitsui et al, "Two Distinct Mechanisms of Augmented Antitumor Activity by Modulation of Immunostimulatory/Inhibitory Signals," Clinical Cancer Res, vol. 16, 2781-2791(2010).
National Cancer Institute, Immunotherapy Agent workshop Jul. 12, 2007, 1-77.
Nocentini et al., "A new member of the tumor necrosis factor/nerve growth factor receptor family inhibits T cell receptor-induced apoptosis," PNAS, vol. 94, 6216-6221 (1997).
Nocentini et al., "GITR: a multifaceted regulator of immunity belonging to the tumor necrosis factor receptor superfamily," Eur J of Immunol, vol. 35 Iss 4, 1016-1022 (2005).
Nocentini et al., "Identification of three novel mRNA splice variants of GITR," Cell Death and Differentiation, vol. 7, 408-410 (2000).
Patel, M. et al., "Agonist anti-GITR monoclonal antibody and stereotactic radiation induce immune-mediated survival advantage in murine intracranial glioma," Journal for ImmunoTherapy of Cancer, vol. 4(28)13 pages (2016).
Piatesi, A. et al., "Immunological Optimization of a Generic Hydrophobic Pocket for High Affinity Hapten Binding and Diets-Alder Activity," ChemBio Chem., vol. 5: 460-466 (2004).
Ponte et al., "Enhancement of humoral and cellular immunity with an antiglucocorticoid-induced tumour necrosis factor receptor monoclonal antibody," Immunology, vol. 130, 231-242 (2010).
Press Release, Tolerx Presents Preclinical Data on Novel T-cell Modulator, TRX518, for Antitumor Immune Response at Federation of Clinical Immunology Societies Scientific Meeting, Cambridge, MA, Jun. 25, 2015, PR Newswire, 1-3.
Baltz, K. et al., "Cancer immunoediting by GITR (glucocorticoidinduced TNF-related protein) ligand in humans: NK cell/tumor cell interactions," The FASEB Journal, Research Communication, vol. 21(8): 2442-2454 (2007).
Chang, W. et al., "Clinical significance of regulatory T cells and CD8+ effector populations in patients with human endometrial carcinoma," Cancer, vol. 116 (24): 5777-5788 (2010).
Cohen et al., "Agonist Anti-GITR Monoclonal Antibody Induces Melanoma Tumor Immunity in Mice by Altering Regulatory T Cell Stability and Intra-Tumor Accumulation," PLoS One, vol. 5, Iss. 5, 1-12 (2010).
Gasparoto, T. et al., "Patients with oral squamous cell carcinoma are characterized by increased frequency of suppressive regulatory T cells in the blood and tumor microenvironment," Cancer Immunology, Immunotherapy, vol. 59: 819-828 (2010).
Padovani, C. et al., "Glucocorticoid-induced tumor necrosis factor receptor expression in patients with cervical human papillomavirus infection," Revista DA Sociedada Brasileira De Medicina Tropical, vol. 46(3):288-292 :(2013).
U.S. Appl. No. 15/578,874, filed Dec. 1, 2017, Xi-Tao Wang.
U.S. Appl. No. 15/369,290, filed Dec. 5, 2016, Changyu Wang.
U.S. Appl. No. 16/663,583, filed Oct. 25, 2019, Changyu Wang.
U.S. Appl. No. 16/578,987, filed Sep. 23, 2019, Changyu Wang.
U.S. Appl. No. 15/646,558, filed Jul. 11, 2017, Changyu Wang.
U.S. Appl. No. 14/949,424, filed Nov. 23, 2015, Changyu Wang.
U.S. Appl. No. 14/732,082, filed Jun. 5, 2015, Changyu Wang.
U.S. Appl. No. 15/776,591, filed May 16, 2018, Changyu Wang.
U.S. Appl. No. 15/578,874, Feb. 10, 2020, S. Aeder.
U.S. Appl. No. 15/578,874, Oct. 10, 2019, J. Roark.
U.S. Appl. No. 15/369,290, Oct. 24, 2019, J. Roark.
U.S. Appl. No. 15/369,290, Jul. 25, 2019, J. Roark.
U.S. Appl. No. 15/369,290, Nov. 8, 2018, J. Roark.
U.S. Appl. No. 15/369,290, Jul. 16, 2018, J. Roark.
U.S. Appl. No. 15/369,290, Feb. 8, 2018, J. Roark.
U.S. Appl. No. 15/776,591, Sep. 29, 2020, M. Pak.
U.S. Appl. No. 15/776,591, Jan. 29, 2020, S. Shafer.
U.S. Appl. No. 15/776,591, Nov. 4, 2019, S. Shafer.
U.S. Appl. No. 16/578,987, Apr. 27, 2020, S. Shafer.
U.S. Appl. No. 15/646,558, Jun. 21, 2019, S. Shafer.
U.S. Appl. No. 15/646,558, Feb. 4, 2019, S. Shafer.
U.S. Appl. No. 15/646,558, Sep. 26, 2018, S. Shafer.
U.S. Appl. No. 15/646,558, May 30, 2018, S. Shafer.
U.S. Appl. No. 14/949,424, Apr. 20, 2017, S. Shafer.
U.S. Appl. No. 14/949,424, Apr. 13, 2017, S. Shafer.
U.S. Appl. No. 14/949,424, Jan. 25, 2017, S. Shafer.
U.S. Appl. No. 14/949,424, Nov. 4, 2016, S. Shafer.
U.S. Appl. No. 14/732,082, Aug. 24, 2015, S. Shafer.
U.S. Appl. No. 14/732,082, Jul. 13, 2015, S. Shafer.
U.S. Appl. No. 16/578,987, Oct. 16, 2020, M. Pak.
U.S. Appl. No. 15/776,591, Jan. 1, 2021, M. Pak.
Printout from the R&D Systems website showing a list of available anti-GITR antibodies, Jul. 2, 2014, 1-2.
Reichert, J., "Monoclonal antibodies in the clinic," Nat. Biotech, vol. 19, 819-822 (2001).
Ronchetti et al., "GITR, a member of the TNF receptor superfamily, is costimulatory to mouse T lymphocyte subpopulations," Eur J Immunol, vol. 34, 613-622 (2004).
Rosenzweig et al., "Development of TRX518, an aglycosyl humanized monoclonal antibody (Mab) agonist of huGITR.," ASCO Meeting Library 2010 Annual Meeting, 1-2.
Rudikoff, S. et al., "Single amino acid substitution altering antigen-binding specificity," PNAS, vol. 79: 1979-1983 (1982).

(56) References Cited

OTHER PUBLICATIONS

Safety Study of AMG 228 to Treat Solid Tumors, ClinicalTrials.gov Identifier: NCT02437916, date first posted: May 8, 2015, date last updated: Feb. 6, 2017,date retrieved: Feb. 14, 2018, 7 pages, <https://clinicaltrials.gov/show/NCT02437916>.
Schaer et al., "Anti-GITR antibodies—Potential Clinical applications for tumor immunotherapy," Curr Opin in Investigational Drugs, vol. 11 (12), 1378-1386 (2010).
Schaer, et al. "Modulation of GITR for cancer immunotherapy," Curr Opin in Immunol, vol. 24, 217-224 (2012).
Schimizu et al., "Stimulation of CD25+CD4+ regulatory T cells through GITR breaks immunological self-tolerance," Mature Immunol, vol. 3 (2), 135-142 (2002).
Siu, L. et al., "Preliminary results of a phase I/IIa study of BMS-986156 (glucocorticoid-induced tumor necrosis factor receptor-related gene [GITR] agonist), alone and in combination with nivolumab in pts with advanced solid tumors," Journal of Clinical Oncology, vol. 35 (15):Supp. 104: (May 2017) 4 page, retrieved date: Feb. 14, 2018, <http://ascopubs.org/doi/abs/10.1200/JCO.2017.35.15_suppl.104>.
Siu, L. et al., Preliminary Results of a Phase 1/2a Study of BMS-986156 (glucocorticoid-induced tumor necrosis factor receptor-related gene [GITR] agonist) Alone and in Combination With Nivolumab in Patients With Advanced Solid Tumors, slides presented at the ASCO Annual Meeting 2017, Jun. 2, 2017, 18 pages.
Study of MK-1248 With and Without Pembrolizumab (MK-3475) for Participants With Advanced Solid Tumors (MK-1248-001), ClinicalTrials.gov Identifier: NCT02553499, date first posted: Sep. 17, 2015 date last updated: Feb. 2, 2018, date retrieved: Feb. 14, 2018, 6 pages <https://clinicaltrials.gov/show/NCT02553499>.
Study of MK-4166 and MK-4166 in Combination With Pembrolizumab (MK-3475) in Participants With Advanced Solid Tumors (MK-4166-001), ClinicalTrials.gov Identifier: NCT02132754, date first posted: May 7, 2014, date last updated: Jan. 25, 2018, date retrieved: Feb. 14, 2018, 7 pages <https://clinicaltrials.gov/ct2/show/NCT02132754?term=mk4166&rank=1>.
Turk, et al., "Concomitant Tumor Immunity to a Poorly Immunogenic Melanoma Is Prevented by Regulatory T Cells," Journal of Exp Medicine, vol. 200 (6) 771-782 (2004).
U.S. Appl. No. 60/665,322, filed Mar. 25, 2005, 62 pages.
U.S. Appl. No. 60/687,265, filed Jun. 3, 2005, 71 pages.
Wang, H. et al., "Integration of Nonclinical PK/PD Data for First-in-Human Starting Dose Selection of Cancer Immune therapeutics," presented on Oct. 18, 2017 at 2017 (ISoP) International Society of Pharmacometrics—8th American Conference on Pharmacometrics (ACoP 8), 17 pages.
Website Information for Monoclonal Anti-human GITR/TNFRSF 18 MAb (Clone 110416), Catalog No. MAB689, 1-2, Sep. 21, 2004.
White, A. et al., "Conformation of the Human Immunoglobulin G2 Hinge Imparts Superagonistic Properties to Immunostimulatory Anticancer Antibodies," Cancer Cell, vol. 27(1):138-148 (2015).
Whiteside, S. et al., "IkB proteins: structure, function and regulation," Seminars in Cancer Biology, vol. 8, 75-82 (1997).
Yang, W. et al., "CDR Walking Mutagenesis for the Affinity Maturation of a Potent Human Anti-HIV-1 Antibody into the Picomolar Range," J. Mol. Biol., vol. 254 (3): 392-403 (1995).
Page 39 of the 1988 Stratagene Catalog, 2 pages.

Anti-GITR 6G10 VH (hIgG2)

V segment: 3-33
D segment: 3-10
J segment: JH6b

```
         Q   V   Q   L   V   E   S   G   G   D   V   V   Q   P   G   R   S
1       CAG GTG CAG CTG GTG GAG TCT GGG GGA GAC GTG GTC CAG CCT GGG AGG TCC

                                                       _CDR1___________
         L   R   L   S   C   A   A   S   G   F   T   F   S   T   Y   G   M
52      CTG AGA CTC TCC TGT GCA GCG TCT GGA TTC ACC TTC AGT ACC TAT GGC ATG

        ___                                                    _CDR2__
         H   W   V   R   Q   A   P   G   K   G   L   E   W   V   A   V   T
103     CAC TGG GTC CGC CAG GCT CCA GGC AAG GGG CTG GAG TGG GTG GCA GTT ACA

        _____________________________________________________________
         W   Y   A   G   S   N   K   F   Y   A   D   S   V   K   G   R   F
154     TGG TAT GCT GGA AGT AAT AAA TTT TAT GCA GAC TCC GTG AAG GGC CGA TTC

         T   I   S   R   D   N   S   K   N   T   L   Y   L   Q   M   N   S
205     ACC ATC TCC AGA GAC AAT TCC AAG AAC ACG CTG TAT CTG CAA ATG AAC AGC

                                                       _CDR3___________
         L   R   A   E   D   T   A   V   Y   Y   C   A   R   G   G   S   M
256     CTG AGA GCC GAG GAC ACG GCT GTG TAT TAC TGT GCG AGA GGA GGT AGT ATG

        ____________________________________________
         V   R   G   L   Y   Y   Y   G   M   D   V   W   G   Q   G   T   T
307     GTT CGG GGA CTT TAT TAT TAC GGT ATG GAC GTC TGG GGC CAA GGG ACC ACG

         V   T   V   S   S
358     GTC ACC GTC TCC TCA
```

FIG. 1

Anti-GITR 6G10 VK1 (hKappa)
V segment: L18
J segment: JK2

```
          A   I   Q   L   T   Q   S   P   S   S   L   S   A   S   V   G   D
1         GCC ATC CAG TTG ACC CAG TCT CCA TCC TCC CTG TCT GCA TCT GTA GGA GAC

                                  __CDR1_______________________________________
          R   V   T   I   T   C   R   A   S   Q   G   I   S   S   A   L   A
52        AGA GTC ACC ATC ACT TGC CGG GCA AGT CAG GGC ATT AGC AGT GCT TTA GCC

                                                                      __CDR2____
          W   Y   Q   Q   K   P   G   K   A   P   K   L   L   I   Y   D   A
103       TGG TAT CAG CAG AAA CCA GGG AAA GCT CCT AAG CTC CTG ATC TAT GAT GCC

          ___________________
          S   S   L   E   S   G   V   P   S   R   F   S   G   S   G   S   G
154       TCC AGT TTG GAA AGT GGG GTC CCA TCA AGG TTC AGC GGC AGT GGA TCT GGG

          T   D   F   T   L   T   I   S   S   L   Q   P   E   D   F   A   T
205       ACA GAT TTC ACT CTC ACC ATC AGC AGC CTG CAG CCT GAA GAT TTT GCA ACT

                      __CDR3______________________________
          Y   Y   C   Q   Q   F   N   S   Y   P   Y   T   F   G   Q   G   T
256       TAT TAC TGT CAA CAG TTT AAT AGT TAC CCG TAC ACT TTT GGC CAG GGG ACC

          K   L   E   I   K
307       AAG CTG GAG ATC AAA
```

FIG. 2

Anti-GITR 6G10 VH (hIgG2)

| | | | | | | | | | | | | | | | | | | | | | | | |
|---|---|---|---|---|---|---|---|---|---|---|---|---|---|---|---|---|---|---|---|---|---|---|---|
| 3-33 | Q | V | Q | L | V | E | S | G | G | G | V | V | Q | P | G | R | S | L | R | L | S | C | A |
| INPUT | - | - | - | - | - | - | - | - | - | D | - | - | - | - | - | - | - | - | - | - | - | - | - |
| | | | | | | | | _CDR1____ | | | | | | | | | | | | | | | |
| 3-33 | A | S | G | F | T | F | S | S | Y | G | M | H | W | V | R | Q | A | P | G | K | G | L | E |
| INPUT | - | - | - | - | - | - | - | T | - | - | - | - | - | - | - | - | - | - | - | - | - | - | - |
| | | | | _CDR2____ | | | | | | | | | | | | | | | | | | | |
| 3-33 | W | V | A | V | I | W | Y | D | G | S | N | K | Y | Y | A | D | S | V | K | G | R | F | T |
| INPUT | - | - | - | - | T | - | - | A | - | - | - | - | F | - | - | - | - | - | - | - | - | - | - |
| 3-33 | I | S | R | D | N | S | K | N | T | L | Y | L | Q | M | N | S | L | R | A | E | D | T | A |
| INPUT | - | - | - | - | - | - | - | - | - | - | - | - | - | - | - | - | - | - | - | - | - | - | - |
| | | | | | | | _CDR3____ | | | | | | | | | | | | | | | | |
| 3-33 | V | Y | Y | C | A | R | | | | | | | | | | | | | | | | | |
| 3-10 | | | | | | | | | | M | V | R | G | | | | | | | | | | |
| JH6 | | | | | | | | | | | | | | | Y | Y | Y | G | M | D | V | W | G |
| INPUT | - | - | - | - | - | - | G | G | S | - | - | - | - | L | - | - | - | - | - | - | - | - | - |
| JH6 | Q | G | T | T | V | T | V | S | S | | | | | | | | | | | | | | |
| INPUT | - | - | - | - | - | - | - | - | - | | | | | | | | | | | | | | |

FIG. 3

Anti-GITR 6G10 VK1 (hKappa)

```
L18      A  I  Q  L  T  Q  S  P  S  S  L  S  A  S  V  G  D  R  V  T  I  T  C
INPUT    -  -  -  -  -  -  -  -  -  -  -  -  -  -  -  -  -  -  -  -  -  -  -

         _CDR1______________________
L18      R  A  S  Q  G  I  S  S  A  L  A  W  Y  Q  Q  K  P  G  K  A  P  K  L
INPUT    -  -  -  -  -  -  -  -  -  -  -  -  -  -  -  -  -  -  -  -  -  -  -

                  _CDR2_______________
L18      L  I  Y  D  A  S  S  L  E  S  G  V  P  S  R  F  S  G  S  G  S  G  T
INPUT    -  -  -  -  -  -  -  -  -  -  -  -  -  -  -  -  -  -  -  -  -  -  -

                                                           _CDR3_______
L18      D  F  T  L  T  I  S  S  L  Q  P  E  D  F  A  T  Y  Y  C  Q  Q  F  N
INPUT    -  -  -  -  -  -  -  -  -  -  -  -  -  -  -  -  -  -  -  -  -  -  -

        ________________
L18      N  Y
JK2               Y  T  F  G  Q  G  T  K  L  E  I  K
INPUT    S  -  P  -  -  -  -  -  -  -  -  -  -  -  -
```

FIG. 4

```
         GITR 6G10 VH
    ~~~~~~~~~~~~~~~~~~~~~~~~~~~~~~~~~~~~~~~~~~~~~~~~~~~~~~~~~~~
     Q   V   Q   L   V   E   S   G   G   D   V   V   Q   P   G
  1 CAG GTG CAG CTG GTG GAG TCT GGG GGA GAC GTG GTC CAG CCT GGG
                    GITR 6G10 VH
    ~~~~~~~~~~~~~~~~~~~~~~~~~~~~~~~~~~~~~~~~~~~~~~~~~~~~~~~~~~~
     R   S   L   R   L   S   C   A   A   S   G   F   T   F   S
 46 AGG TCC CTG AGA CTC TCC TGT GCA GCG TCT GGA TTC ACC TTC AGT
                    GITR 6G10 VH
    ~~~~~~~~~~~~~~~~~~~~~~~~~~~~~~~~~~~~~~~~~~~~~~~~~~~~~~~~~~~
     T   Y   G   M   H   W   V   R   Q   A   P   G   K   G   L
 91 ACC TAT GGC ATG CAC TGG GTC CGC CAG GCT CCA GGC AAG GGG CTG
                    GITR 6G10 VH
    ~~~~~~~~~~~~~~~~~~~~~~~~~~~~~~~~~~~~~~~~~~~~~~~~~~~~~~~~~~~
     E   W   V   A   V   T   W   Y   A   G   S   N   K   F   Y
136 GAG TGG GTG GCA GTT ACA TGG TAT GCT GGA AGT AAT AAA TTT TAT
                    GITR 6G10 VH
    ~~~~~~~~~~~~~~~~~~~~~~~~~~~~~~~~~~~~~~~~~~~~~~~~~~~~~~~~~~~
     A   D   S   V   K   G   R   F   T   I   S   R   D   N   S
181 GCA GAC TCC GTG AAG GGC CGA TTC ACC ATC TCC AGA GAC AAT TCC
                    GITR 6G10 VH
    ~~~~~~~~~~~~~~~~~~~~~~~~~~~~~~~~~~~~~~~~~~~~~~~~~~~~~~~~~~~
     K   N   T   L   Y   L   Q   M   N   S   L   R   A   E   D
226 AAG AAC ACG CTG TAT CTG CAA ATG AAC AGC CTG AGA GCC GAG GAC
                    GITR 6G10 VH
    ~~~~~~~~~~~~~~~~~~~~~~~~~~~~~~~~~~~~~~~~~~~~~~~~~~~~~~~~~~~
     T   A   V   Y   Y   C   A   R   G   G   S   M   V   R   G
271 ACG GCT GTG TAT TAC TGT GCG AGA GGA GGT AGT ATG GTT CGG GGA
                    GITR 6G10 VH
    ~~~~~~~~~~~~~~~~~~~~~~~~~~~~~~~~~~~~~~~~~~~~~~~~~~~~~~~~~~~
     L   Y   Y   Y   G   M   D   V   W   G   Q   G   T   T   V
316 CTT TAT TAT TAC GGT ATG GAC GTC TGG GGC CAA GGG ACC ACG GTC
                                 mIgG2a constant
                        ~~~~~~~~~~~~~~~~~~~~~~~~~~~~~~~~~~~~~~~~
    GITR 6G10 VH
    ~~~~~~~~~~~~~~~~
     T   V   S   S   A   K   T   T   A   P   S   V   Y   P   L
361 ACC GTC TCC TCA GCC AAA ACA ACA GCC CCA TCG GTC TAT CCG CTA
                   mIgG2a constant
    ~~~~~~~~~~~~~~~~~~~~~~~~~~~~~~~~~~~~~~~~~~~~~~~~~~~~~~~~~~~
     A   P   V   C   G   D   T   T   G   S   S   V   T   L   G
406 GCC CCT GTG TGT GGA GAT ACA ACT GGC TCC TCG GTG ACT CTA GGA
                   mIgG2a constant
    ~~~~~~~~~~~~~~~~~~~~~~~~~~~~~~~~~~~~~~~~~~~~~~~~~~~~~~~~~~~
     C   L   V   K   G   Y   F   P   E   P   V   T   L   T   W
451 TGC CTG GTC AAG GGT TAT TTC CCT GAG CCA GTG ACC TTG ACC TGG
                   mIgG2a constant
    ~~~~~~~~~~~~~~~~~~~~~~~~~~~~~~~~~~~~~~~~~~~~~~~~~~~~~~~~~~~
     N   S   G   S   L   S   S   G   V   H   T   F   P   A   V
496 AAC TCT GGA TCC CTG TCC AGT GGT GTG CAC ACC TTC CCA GCT GTC
                   mIgG2a constant
    ~~~~~~~~~~~~~~~~~~~~~~~~~~~~~~~~~~~~~~~~~~~~~~~~~~~~~~~~~~~
     L   Q   S   D   L   Y   T   L   S   S   S   V   T   V   T
541 CTG CAG TCT GAC CTC TAC ACC CTC AGC AGC TCA GTG ACT GTA ACC
                   mIgG2a constant
    ~~~~~~~~~~~~~~~~~~~~~~~~~~~~~~~~~~~~~~~~~~~~~~~~~~~~~~~~~~~
     S   S   T   W   P   S   Q   S   I   T   C   N   V   A   H
586 TCG AGC ACC TGG CCC AGC CAG TCC ATC ACC TGC AAT GTG GCC CAC
                   mIgG2a constant
    ~~~~~~~~~~~~~~~~~~~~~~~~~~~~~~~~~~~~~~~~~~~~~~~~~~~~~~~~~~~
     P   A   S   S   T   K   V   D   K   K   I   E   P   R   G
631 CCG GCA AGC AGC ACC AAG GTG GAC AAG AAA ATT GAG CCC AGA GGG
                   mIgG2a constant
```

FIG. 5

```
    ~~~~~~~~~~~~~~~~~~~~~~~~~~~~~~~~~~~~~~~~~~~~~~~~~~~~~~~~~~~
     P   T   I   K   P   C   P   P   C   K   C   P   A   P   N
 676 CCC ACA ATC AAG CCC TGT CCT CCA TGC AAA TGC CCA GCA CCT AAC
                    mIgG2a constant
    ~~~~~~~~~~~~~~~~~~~~~~~~~~~~~~~~~~~~~~~~~~~~~~~~~~~~~~~~~~~
     L   L   G   G   P   S   V   F   I   F   P   P   K   I   K
 721 CTC TTG GGT GGA CCA TCC GTC TTC ATC TTC CCT CCA AAG ATC AAG
                    mIgG2a constant
    ~~~~~~~~~~~~~~~~~~~~~~~~~~~~~~~~~~~~~~~~~~~~~~~~~~~~~~~~~~~
     D   V   L   M   I   S   L   S   P   I   V   T   C   V   V
 766 GAT GTA CTC ATG ATC TCC CTG AGC CCC ATA GTC ACA TGT GTG GTG
                    mIgG2a constant
    ~~~~~~~~~~~~~~~~~~~~~~~~~~~~~~~~~~~~~~~~~~~~~~~~~~~~~~~~~~~
     V   D   V   S   E   D   D   P   D   V   Q   I   S   W   F
 811 GTG GAT GTG AGC GAG GAT GAC CCA GAT GTC CAG ATC AGC TGG TTT
                    mIgG2a constant
    ~~~~~~~~~~~~~~~~~~~~~~~~~~~~~~~~~~~~~~~~~~~~~~~~~~~~~~~~~~~
     V   N   N   V   E   V   H   T   A   Q   T   Q   T   H   R
 856 GTG AAC AAC GTG GAA GTA CAC ACA GCT CAG ACA CAA ACC CAT AGA
                    mIgG2a constant
    ~~~~~~~~~~~~~~~~~~~~~~~~~~~~~~~~~~~~~~~~~~~~~~~~~~~~~~~~~~~
     E   D   Y   N   S   T   L   R   V   V   S   A   L   P   I
 901 GAG GAT TAC AAC AGT ACT CTC CGG GTG GTC AGT GCC CTC CCC ATC
                    mIgG2a constant
    ~~~~~~~~~~~~~~~~~~~~~~~~~~~~~~~~~~~~~~~~~~~~~~~~~~~~~~~~~~~
     Q   H   Q   D   W   M   S   G   K   E   F   K   C   K   V
 946 CAG CAC CAG GAC TGG ATG AGT GGC AAG GAG TTC AAA TGC AAG GTC
                    mIgG2a constant
    ~~~~~~~~~~~~~~~~~~~~~~~~~~~~~~~~~~~~~~~~~~~~~~~~~~~~~~~~~~~
     N   N   K   D   L   P   A   P   I   E   R   T   I   S   K
 991 AAC AAC AAA GAC CTC CCA GCG CCC ATC GAG AGA ACC ATC TCA AAA
                    mIgG2a constant
    ~~~~~~~~~~~~~~~~~~~~~~~~~~~~~~~~~~~~~~~~~~~~~~~~~~~~~~~~~~~
     P   K   G   S   V   R   A   P   Q   V   Y   V   L   P   P
1036 CCC AAA GGG TCA GTA AGA GCT CCA CAG GTA TAT GTC TTG CCT CCA
                    mIgG2a constant
    ~~~~~~~~~~~~~~~~~~~~~~~~~~~~~~~~~~~~~~~~~~~~~~~~~~~~~~~~~~~
     P   E   E   E   M   T   K   K   Q   V   T   L   T   C   M
1081 CCA GAA GAA GAG ATG ACT AAG AAA CAG GTC ACT CTG ACC TGC ATG
                    mIgG2a constant
    ~~~~~~~~~~~~~~~~~~~~~~~~~~~~~~~~~~~~~~~~~~~~~~~~~~~~~~~~~~~
     V   T   D   F   M   P   E   D   I   Y   V   E   W   T   N
1126 GTC ACA GAC TTC ATG CCT GAA GAC ATT TAC GTG GAG TGG ACC AAC
                    mIgG2a constant
    ~~~~~~~~~~~~~~~~~~~~~~~~~~~~~~~~~~~~~~~~~~~~~~~~~~~~~~~~~~~
     N   G   K   T   E   L   N   Y   K   N   T   E   P   V   L
1171 AAC GGG AAA ACA GAG CTA AAC TAC AAG AAC ACT GAA CCA GTC CTG
                    mIgG2a constant
    ~~~~~~~~~~~~~~~~~~~~~~~~~~~~~~~~~~~~~~~~~~~~~~~~~~~~~~~~~~~
     D   S   D   G   S   Y   F   M   Y   S   K   L   R   V   E
1216 GAC TCT GAT GGT TCT TAC TTC ATG TAC AGC AAG CTG AGA GTG GAA
                    mIgG2a constant
    ~~~~~~~~~~~~~~~~~~~~~~~~~~~~~~~~~~~~~~~~~~~~~~~~~~~~~~~~~~~
     K   K   N   W   V   E   R   N   S   Y   S   C   S   V   V
1261 AAG AAG AAC TGG GTG GAA AGA AAT AGC TAC TCC TGT TCA GTG GTC
```

FIG. 5 (continued)

```
                  mIgG2a constant
     ~~~~~~~~~~~~~~~~~~~~~~~~~~~~~~~~~~~~~~~~~~~~~~~~~~~~~~~~~~~~
      H   E   G   L   H   N   H   H   T   T   K   S   F   S   R
1306 CAC GAG GGT CTG CAC AAT CAC CAC ACG ACT AAG AGC TTC TCC CGG
     mIgG2a constant
     ~~~~~~~~~~~~~~~~~~~
      T   P   G   K   *
1351 ACT CCG GGT AAA TGA
```

FIG. 5 (continued)

```
GITR 6G10 VK
       ~~~~~~~~~~~~~~~~~~~~~~~~~~~~~~~~~~~~~~~~~~~~~~~~~~~~~~~~~~~
        A   I   Q   L   T   Q   S   P   S   S   L   S   A   S   V
     1 GCC ATC CAG TTG ACC CAG TCT CCA TCC TCC CTG TCT GCA TCT GTA
                       GITR 6G10 VK
       ~~~~~~~~~~~~~~~~~~~~~~~~~~~~~~~~~~~~~~~~~~~~~~~~~~~~~~~~~~~
        G   D   R   V   T   I   T   C   R   A   S   Q   G   I   S
    46 GGA GAC AGA GTC ACC ATC ACT TGC CGG GCA AGT CAG GGC ATT AGC
                       GITR 6G10 VK
       ~~~~~~~~~~~~~~~~~~~~~~~~~~~~~~~~~~~~~~~~~~~~~~~~~~~~~~~~~~~
        S   A   L   A   W   Y   Q   Q   K   P   G   K   A   P   K
    91 AGT GCT TTA GCC TGG TAT CAG CAG AAA CCA GGG AAA GCT CCT AAG
                       GITR 6G10 VK
       ~~~~~~~~~~~~~~~~~~~~~~~~~~~~~~~~~~~~~~~~~~~~~~~~~~~~~~~~~~~
        L   L   I   Y   D   A   S   S   L   E   S   G   V   P   S
   136 CTC CTG ATC TAT GAT GCC TCC AGT TTG GAA AGT GGG GTC CCA TCA
                       GITR 6G10 VK
       ~~~~~~~~~~~~~~~~~~~~~~~~~~~~~~~~~~~~~~~~~~~~~~~~~~~~~~~~~~~
        R   F   S   G   S   G   S   G   T   D   F   T   L   T   I
   181 AGG TTC AGC GGC AGT GGA TCT GGG ACA GAT TTC ACT CTC ACC ATC
                       GITR 6G10 VK
       ~~~~~~~~~~~~~~~~~~~~~~~~~~~~~~~~~~~~~~~~~~~~~~~~~~~~~~~~~~~
        S   S   L   Q   P   E   D   F   A   T   Y   Y   C   Q   Q
   226 AGC AGC CTG CAG CCT GAA GAT TTT GCA ACT TAT TAC TGT CAA CAG
                       GITR 6G10 VK
       ~~~~~~~~~~~~~~~~~~~~~~~~~~~~~~~~~~~~~~~~~~~~~~~~~~~~~~~~~~~
        F   N   S   Y   P   Y   T   F   G   Q   G   T   K   L   E
   271 TTT AAT AGT TAC CCG TAC ACT TTT GGC CAG GGG ACC AAG CTG GAG
                           murine kappa C
                   ~~~~~~~~~~~~~~~~~~~~~~~~~~~~~~~~~~~~~~~~~~~~~~~
       GITR 6G10 VK
       ~~~~~~~~
        I   K   R   A   D   A   A   P   T   V   S   I   F   P   P
   316 ATC AAA CGG GCT GAT GCT GCA CCA ACT GTA TCC ATC TTC CCA CCA
                                               ~~~~~~
                                                   DMTm89
                                   ~~~~~~~~~~~~~~~~~~~~~~
                                            DMTm88
                      murine kappa C
       ~~~~~~~~~~~~~~~~~~~~~~~~~~~~~~~~~~~~~~~~~~~~~~~~~~~~~~~~~~~
        S   S   E   Q   L   T   S   G   G   A   S   V   V   C   F
   361 TCC AGT GAG CAA TTG ACA TCT GGA GGT GCC TCA GTC GTG TGC TTC
       ~~~~~~
       .....
       ~~~~
       ...
                      murine kappa C
       ~~~~~~~~~~~~~~~~~~~~~~~~~~~~~~~~~~~~~~~~~~~~~~~~~~~~~~~~~~~
        L   N   N   F   Y   P   K   D   I   N   V   K   W   K   I
   406 TTG AAC AAC TTC TAC CCC AAA GAC ATC AAT GTC AAG TGG AAG ATT
                      murine kappa C
       ~~~~~~~~~~~~~~~~~~~~~~~~~~~~~~~~~~~~~~~~~~~~~~~~~~~~~~~~~~~
        D   G   S   E   R   Q   N   G   V   L   N   S   W   T   D
   451 GAT GGC AGT GAA CGA CAA AAT GGC GTC CTG AAC AGT TGG ACC GAT
                      murine kappa C
       ~~~~~~~~~~~~~~~~~~~~~~~~~~~~~~~~~~~~~~~~~~~~~~~~~~~~~~~~~~~
        Q   D   S   K   D   S   T   Y   S   M   S   S   T   L   T
   496 CAG GAC AGC AAA GAC AGC ACC TAC AGC ATG AGC AGC ACC CTC ACG
                      murine kappa C
       ~~~~~~~~~~~~~~~~~~~~~~~~~~~~~~~~~~~~~~~~~~~~~~~~~~~~~~~~~~~
        L   T   K   D   E   Y   E   R   H   N   S   Y   T   C   E
```

FIG. 6

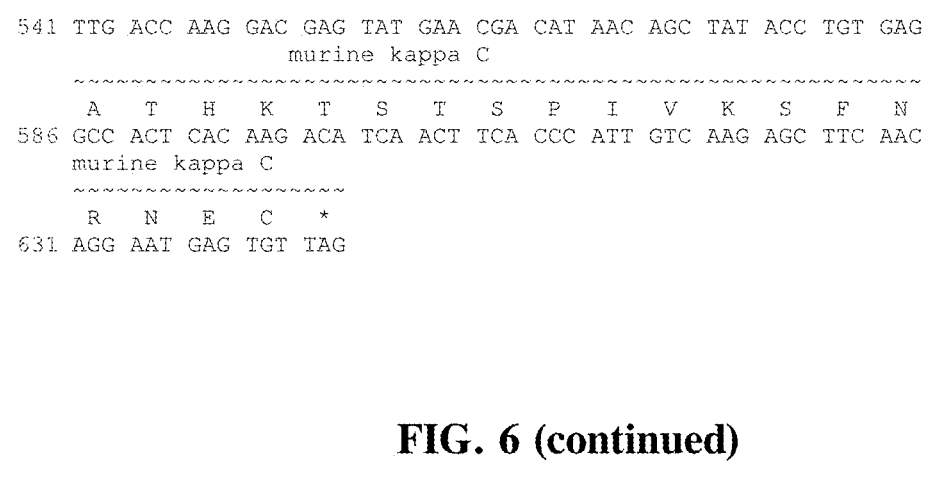

```
541 TTG ACC AAG GAC GAG TAT GAA CGA CAT AAC AGC TAT ACC TGT GAG
                   murine kappa C
    ~~~~~~~~~~~~~~~~~~~~~~~~~~~~~~~~~~~~~~~~~~~~~~~~~~~~~~~~~~~~
     A   T   H   K   T   S   T   S   P   I   V   K   S   F   N
586 GCC ACT CAC AAG ACA TCA ACT TCA CCC ATT GTC AAG AGC TTC AAC
    murine kappa C
    ~~~~~~~~~~~~~~~~~~~
     R   N   E   C   *
631 AGG AAT GAG TGT TAG
```

FIG. 6 (continued)

SEQUENCE LISTING

```
<160> NUMBER OF SEQ ID NOS: 228

<210> SEQ ID NO 1
<211> LENGTH: 241
<212> TYPE: PRT
<213> ORGANISM: Homo sapiens
<220> FEATURE:
<221> NAME/KEY: misc_feature
<222> LOCATION: (1)..(241)
<223> OTHER INFORMATION: human GITR isoform 1

<400> SEQUENCE: 1

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val


<210> SEQ ID NO 2
<211> LENGTH: 255
<212> TYPE: PRT
<213> ORGANISM: Homo sapiens
```

<220> FEATURE:
<221> NAME/KEY: misc_feature
<222> LOCATION: (1)..(255)
<223> OTHER INFORMATION: human GITR isoform 2

<400> SEQUENCE: 2

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Cys Trp Arg Cys Arg Arg Arg Pro Lys Thr
    130                 135                 140

Pro Glu Ala Ala Ser Ser Pro Arg Lys Ser Gly Ala Ser Asp Arg Gln
145                 150                 155                 160

Arg Arg Arg Gly Gly Trp Glu Thr Cys Gly Cys Glu Pro Gly Arg Pro
                165                 170                 175

Pro Gly Pro Pro Thr Ala Ala Ser Pro Ser Pro Gly Ala Pro Gln Ala
            180                 185                 190

Ala Gly Ala Leu Arg Ser Ala Leu Gly Arg Ala Leu Leu Pro Trp Gln
        195                 200                 205

Gln Lys Trp Val Gln Glu Gly Gly Ser Asp Gln Arg Pro Gly Pro Cys
    210                 215                 220

Ser Ser Ala Ala Ala Ala Gly Pro Cys Arg Arg Glu Arg Glu Thr Gln
225                 230                 235                 240

Ser Trp Pro Pro Ser Ser Leu Ala Gly Pro Asp Gly Val Gly Ser
                245                 250                 255
```

<210> SEQ ID NO 3
<211> LENGTH: 234
<212> TYPE: PRT
<213> ORGANISM: Homo sapiens
<220> FEATURE:
<221> NAME/KEY: misc_feature
<222> LOCATION: (1)..(234)
<223> OTHER INFORMATION: human GITR isoform 3

<400> SEQUENCE: 3

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60
```

-continued

```
Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Lys Thr Gln Leu Leu Leu Glu Val Pro Pro Ser Thr Glu Asp Ala
        195                 200                 205

Arg Ser Cys Gln Phe Pro Glu Glu Glu Arg Gly Glu Arg Ser Ala Glu
    210                 215                 220

Glu Lys Gly Arg Leu Gly Asp Leu Trp Val
225                 230
```

<210> SEQ ID NO 4
<211> LENGTH: 137
<212> TYPE: PRT
<213> ORGANISM: Homo sapiens
<220> FEATURE:
<221> NAME/KEY: misc_feature
<222> LOCATION: (1)..(137)
<223> OTHER INFORMATION: extracellular portion of mature human GITR

<400> SEQUENCE: 4

```
Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro
    130                 135
```

<210> SEQ ID NO 5
<211> LENGTH: 5
<212> TYPE: PRT
<213> ORGANISM: Artificial Sequence
<220> FEATURE:
<223> OTHER INFORMATION: Synthetic: 6G10 VH CDR1

<400> SEQUENCE: 5

Thr Tyr Gly Met His
1 5

<210> SEQ ID NO 6
<211> LENGTH: 17
<212> TYPE: PRT
<213> ORGANISM: Artificial Sequence
<220> FEATURE:
<223> OTHER INFORMATION: Synthetic: 6G10 VH CDR2

<400> SEQUENCE: 6

Val Thr Trp Tyr Ala Gly Ser Asn Lys Phe Tyr Ala Asp Ser Val Lys
1 5 10 15

Gly

<210> SEQ ID NO 7
<211> LENGTH: 15
<212> TYPE: PRT
<213> ORGANISM: Artificial Sequence
<220> FEATURE:
<223> OTHER INFORMATION: Synthetic: 6G10 VH CDR3

<400> SEQUENCE: 7

Gly Gly Ser Met Val Arg Gly Leu Tyr Tyr Tyr Gly Met Asp Val
1 5 10 15

<210> SEQ ID NO 8
<211> LENGTH: 11
<212> TYPE: PRT
<213> ORGANISM: Artificial Sequence
<220> FEATURE:
<223> OTHER INFORMATION: Synthetic: 6G10 VL CDR1

<400> SEQUENCE: 8

Arg Ala Ser Gln Gly Ile Ser Ser Ala Leu Ala
1 5 10

<210> SEQ ID NO 9
<211> LENGTH: 7
<212> TYPE: PRT
<213> ORGANISM: Artificial Sequence
<220> FEATURE:
<223> OTHER INFORMATION: Synthetic: 6G10 VL CDR2

<400> SEQUENCE: 9

Asp Ala Ser Ser Leu Glu Ser
1 5

<210> SEQ ID NO 10
<211> LENGTH: 9
<212> TYPE: PRT
<213> ORGANISM: Artificial Sequence
<220> FEATURE:
<223> OTHER INFORMATION: Synthetic: 6G10 VL CDR3

<400> SEQUENCE: 10

Gln Gln Phe Asn Ser Tyr Pro Tyr Thr
1 5

<210> SEQ ID NO 11
<211> LENGTH: 124
<212> TYPE: PRT
<213> ORGANISM: Artificial Sequence
<220> FEATURE:

<223> OTHER INFORMATION: Synthetic: 6G10 VH

<400> SEQUENCE: 11

Gln Val Gln Leu Val Glu Ser Gly Gly Asp Val Val Gln Pro Gly Arg
1 5 10 15

Ser Leu Arg Leu Ser Cys Ala Ala Ser Gly Phe Thr Phe Ser Thr Tyr
20 25 30

Gly Met His Trp Val Arg Gln Ala Pro Gly Lys Gly Leu Glu Trp Val
35 40 45

Ala Val Thr Trp Tyr Ala Gly Ser Asn Lys Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Ser Met Val Arg Gly Leu Tyr Tyr Tyr Gly Met Asp
100 105 110

Val Trp Gly Gln Gly Thr Thr Val Thr Val Ser Ser
115 120

<210> SEQ ID NO 12
<211> LENGTH: 107
<212> TYPE: PRT
<213> ORGANISM: Artificial Sequence
<220> FEATURE:
<223> OTHER INFORMATION: Synthetic: 6G10 VL

<400> SEQUENCE: 12

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Tyr
85 90 95

Thr Phe Gly Gln Gly Thr Lys Leu Glu Ile Lys
100 105

<210> SEQ ID NO 13
<211> LENGTH: 450
<212> TYPE: PRT
<213> ORGANISM: Artificial Sequence
<220> FEATURE:
<223> OTHER INFORMATION: Synthetic: 6G10 full length heavy chain

<400> SEQUENCE: 13

Gln Val Gln Leu Val Glu Ser Gly Gly Asp Val Val Gln Pro Gly Arg
1 5 10 15

Ser Leu Arg Leu Ser Cys Ala Ala Ser Gly Phe Thr Phe Ser Thr Tyr
20 25 30

Gly Met His Trp Val Arg Gln Ala Pro Gly Lys Gly Leu Glu Trp Val
35 40 45

Ala Val Thr Trp Tyr Ala Gly Ser Asn Lys Phe Tyr Ala Asp Ser Val

-continued

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 14
```

<211> LENGTH: 214
<212> TYPE: PRT
<213> ORGANISM: Artificial Sequence
<220> FEATURE:
<223> OTHER INFORMATION: Synthetic: 6G10 full length light chain

<400> SEQUENCE: 14

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 454
<212> TYPE: PRT
<213> ORGANISM: Artificial Sequence
<220> FEATURE:
<223> OTHER INFORMATION: Synthetic: chimeric 6G10 antibodyfull length heavy chain

<400> SEQUENCE: 15

```
Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Pro Glu Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
        435                 440                 445

Ser Arg Thr Pro Gly Lys
    450
```

<210> SEQ ID NO 16
<211> LENGTH: 214
<212> TYPE: PRT
<213> ORGANISM: Artificial Sequence
<220> FEATURE:
<223> OTHER INFORMATION: Synthetic: chimeric 6G10 antibodyfull length light chain

<400> SEQUENCE: 16

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 17
<211> LENGTH: 372
<212> TYPE: DNA
<213> ORGANISM: Artificial Sequence
<220> FEATURE:
<223> OTHER INFORMATION: Synthetic: 6G10 (VH) nucleotide sequence

<400> SEQUENCE: 17

```
caggtgcagc tggtggagtc tgggggagac gtggtccagc ctgggaggtc cctgagactc     60

tcctgtgcag cgtctggatt caccttcagt acctatggca tgcactgggt ccgccaggct    120

ccaggcaagg ggctggagtg ggtggcagtt acatggtatg ctggaagtaa taaattttat    180

gcagactccg tgaagggccg attcaccatc tccagagaca attccaagaa cacgctgtat    240

ctgcaaatga acagcctgag agccgaggac acggctgtgt attactgtgc gagaggaggt    300

agtatggttc ggggacttta ttattacggt atggacgtct ggggccaagg gaccacggtc    360

accgtctcct ca                                                         372
```

<210> SEQ ID NO 18
<211> LENGTH: 321
<212> TYPE: DNA
<213> ORGANISM: Artificial Sequence
<220> FEATURE:
<223> OTHER INFORMATION: Synthetic: 6G10 (VL) nucleotide sequence

<400> SEQUENCE: 18

```
gccatccagt tgacccagtc tccatcctcc ctgtctgcat ctgtaggaga cagagtcacc     60
```

atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgtacac ttttggccag 300
gggaccaagc tggagatcaa a 321

<210> SEQ ID NO 19
<211> LENGTH: 1350
<212> TYPE: DNA
<213> ORGANISM: Artificial Sequence
<220> FEATURE:
<223> OTHER INFORMATION: Synthetic: 6G10 (full length wild-type heavy chain) nucleotide sequence

<400> SEQUENCE: 19
caggtgcagc tggtggagtc tgggggagac gtggtccagc ctgggaggtc cctgagactc 60
tcctgtgcag cgtctggatt caccttcagt acctatggca tgcactgggt ccgccaggct 120
ccaggcaagg ggctggagtg ggtggcagtt acatggtatg ctggaagtaa taaattttat 180
gcagactccg tgaagggccg attcaccatc tccagagaca attccaagaa cacgctgtat 240
ctgcaaatga acagcctgag agccgaggac acggctgtgt attactgtgc gagaggaggt 300
agtatggttc ggggacttta ttattacggt atggacgtct ggggccaagg gaccacggtc 360
accgtctcct cagcctccac caagggccca tcggtcttcc ccctggcgcc ctgctccagg 420
agcacctccg agagcacagc ggccctgggc tgcctggtca aggactactt ccccgaaccg 480
gtgacggtgt cgtggaactc aggcgctctg accagcggcg tgcacacctt cccagctgtc 540
ctacagtcct caggactcta ctccctcagc agcgtggtga ccgtgccctc cagcaacttc 600
ggcacccaga cctacacctg caacgtagat cacaagccca gcaacaccaa ggtggacaag 660
acagttgagc gcaaatgttg tgtcgagtgc ccaccgtgcc cagcaccacc tgtggcagga 720
ccgtcagtct tcctcttccc cccaaaaccc aaggacaccc tcatgatctc ccggacccct 780
gaggtcacgt gcgtggtggt ggacgtgagc cacgaagacc ccgaggtcca gttcaactgg 840
tacgtggacg gcgtggaggt gcataatgcc aagacaaagc cacgggagga gcagttcaac 900
agcacgttcc gtgtggtcag cgtcctcacc gttgtgcacc aggactggct gaacggcaag 960
gagtacaagt gcaaggtctc caacaaaggc ctcccagccc ccatcgagaa aaccatctcc 1020
aaaaccaaag ggcagccccg agaaccacag gtgtacaccc tgcccccatc ccgggaggag 1080
atgaccaaga accaggtcag cctgacctgc ctggtcaaag gcttctaccc cagcgacatc 1140
gccgtggagt gggagagcaa tgggcagccg gagaacaact acaagaccac acctcccatg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 20
<211> LENGTH: 642
<212> TYPE: DNA
<213> ORGANISM: Artificial Sequence
<220> FEATURE:
<223> OTHER INFORMATION: Synthetic: 6G10 (full length wild-type light chain) nucleotide sequence

<400> SEQUENCE: 20
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgtacac ttttggccag 300
gggaccaagc tggagatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 21
<211> LENGTH: 1365
<212> TYPE: DNA
<213> ORGANISM: Artificial Sequence
<220> FEATURE:
<223> OTHER INFORMATION: Synthetic: chimeric 6G10 heavy chain

<400> SEQUENCE: 21
caggtgcagc tggtggagtc tgggggagac gtggtccagc ctgggaggtc cctgagactc 60
tcctgtgcag cgtctggatt caccttcagt acctatggca tgcactgggt ccgccaggct 120
ccaggcaagg ggctggagtg ggtggcagtt acatggtatg ctggaagtaa taaattttat 180
gcagactccg tgaagggccg attcaccatc tccagagaca attccaagaa cacgctgtat 240
ctgcaaatga acagcctgag agccgaggac acggctgtgt attactgtgc gagaggaggt 300
agtatggttc ggggacttta ttattacggt atggacgtct ggggccaagg gaccacggtc 360
accgtctcct cagccaaaac aacagcccca tcggtctatc cgctagcccc tgtgtgtgga 420
gatacaactg gctcctcggt gactctagga tgcctggtca agggttattt ccctgagcca 480
gtgaccttga cctggaactc tggatccctg tccagtggtg tgcacacctt cccagctgtc 540
ctgcagtctg acctctacac cctcagcagc tcagtgactg taacctcgag cacctggccc 600
agccagtcca tcacctgcaa tgtggcccac ccggcaagca gcaccaaggt ggacaagaaa 660
attgagccca gagggcccac aatcaagccc tgtcctccat gcaaatgccc agcacctaac 720
ctcttgggtg gaccatccgt cttcatcttc cctccaaaga tcaaggatgt actcatgatc 780
tccctgagcc ccatagtcac atgtgtggtg gtggatgtga gcgaggatga cccagatgtc 840
cagatcagct ggtttgtgaa caacgtggaa gtacacacag ctcagacaca aacccataga 900
gaggattaca acagtactct ccgggtggtc agtgccctcc ccatccagca ccaggactgg 960
atgagtggca aggagttcaa atgcaaggtc aacaacaaag acctcccagc gcccatcgag 1020
agaaccatct caaaacccaa agggtcagta agagctccac aggtatatgt cttgcctcca 1080
ccagaagaag agatgactaa gaaacaggtc actctgacct gcatggtcac agacttcatg 1140
cctgaagaca tttacgtgga gtggaccaac aacgggaaaa cagagctaaa ctacaagaac 1200
actgaaccag tcctggactc tgatggttct tacttcatgt acagcaagct gagagtggaa 1260
aagaagaact gggtggaaag aaatagctac tcctgttcag tggtccacga gggtctgcac 1320
aatcaccaca cgactaagag cttctcccgg actccgggta aatga 1365

<210> SEQ ID NO 22

<211> LENGTH: 645
<212> TYPE: DNA
<213> ORGANISM: Artificial Sequence
<220> FEATURE:
<223> OTHER INFORMATION: Synthetic: chimeric 6G10 light chain

<400> SEQUENCE: 22

```
gccatccagt tgacccagtc tccatcctcc ctgtctgcat ctgtaggaga cagagtcacc     60

atcacttgcc gggcaagtca gggcattagc agtgctttag cctggtatca gcagaaacca    120

gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt acccgtacac ttttggccag    300

gggaccaagc tggagatcaa acgggctgat gctgcaccaa ctgtatccat cttcccacca    360

tccagtgagc aattgacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ccgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 23
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: human IgG2 heavy chain constant region

<400> SEQUENCE: 23

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

```
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 24
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: human kappa light chain constant region

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 25
<211> LENGTH: 330
<212> TYPE: PRT
<213> ORGANISM: Mus musculus
<220> FEATURE:
<221> NAME/KEY: misc_feature
<222> LOCATION: (1)..(330)
<223> OTHER INFORMATION: mouse IgG2a heavy chain constant region

<400> SEQUENCE: 25

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45
```

Gly Val His Thr Phe Pro Ala Val Leu Gln Ser Asp Leu Tyr Thr Leu
50 55 60

Ser Ser Ser Val Thr Val Thr Ser Ser Thr Trp Pro Ser Gln Ser Ile
65 70 75 80

Thr Cys Asn Val Ala His Pro Ala Ser Ser Thr Lys Val Asp Lys Lys
85 90 95

Ile Glu Pro Arg Gly Pro Thr Ile Lys Pro Cys Pro Pro Cys Lys Cys
100 105 110

Pro Ala Pro Asn Leu Leu Gly Gly Pro Ser Val Phe Ile Phe Pro Pro
115 120 125

Lys Ile Lys Asp Val Leu Met Ile Ser Leu Ser Pro Ile Val Thr Cys
130 135 140

Val Val Val Asp Val Ser Glu Asp Asp Pro Asp Val Gln Ile Ser Trp
145 150 155 160

Phe Val Asn Asn Val Glu Val His Thr Ala Gln Thr Gln Thr His Arg
165 170 175

Glu Asp Tyr Asn Ser Thr Leu Arg Val Val Ser Ala Leu Pro Ile Gln
180 185 190

His Gln Asp Trp Met Ser Gly Lys Glu Phe Lys Cys Lys Val Asn Asn
195 200 205

Lys Asp Leu Pro Ala Pro Ile Glu Arg Thr Ile Ser Lys Pro Lys Gly
210 215 220

Ser Val Arg Ala Pro Gln Val Tyr Val Leu Pro Pro Pro Glu Glu Glu
225 230 235 240

Met Thr Lys Lys Gln Val Thr Leu Thr Cys Met Val Thr Asp Phe Met
245 250 255

Pro Glu Asp Ile Tyr Val Glu Trp Thr Asn Asn Gly Lys Thr Glu Leu
260 265 270

Asn Tyr Lys Asn Thr Glu Pro Val Leu Asp Ser Asp Gly Ser Tyr Phe
275 280 285

Met Tyr Ser Lys Leu Arg Val Glu Lys Lys Asn Trp Val Glu Arg Asn
290 295 300

Ser Tyr Ser Cys Ser Val Val His Glu Gly Leu His Asn His His Thr
305 310 315 320

Thr Lys Ser Phe Ser Arg Thr Pro Gly Lys
325 330

<210> SEQ ID NO 26
<211> LENGTH: 107
<212> TYPE: PRT
<213> ORGANISM: Mus musculus
<220> FEATURE:
<221> NAME/KEY: misc_feature
<222> LOCATION: (1)..(107)
<223> OTHER INFORMATION: mouse kappa light chain constant region

<400> SEQUENCE: 26

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

```
Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 27
<211> LENGTH: 124
<212> TYPE: PRT
<213> ORGANISM: Artificial Sequence
<220> FEATURE:
<223> OTHER INFORMATION: Synthetic: 28F3 (VH)

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser
        115                 120


<210> SEQ ID NO 28
<211> LENGTH: 107
<212> TYPE: PRT
<213> ORGANISM: Artificial Sequence
<220> FEATURE:
<223> OTHER INFORMATION: Synthetic: 28F3 (VL)

<400> SEQUENCE: 28

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105


<210> SEQ ID NO 29
<211> LENGTH: 450
<212> TYPE: PRT
<213> ORGANISM: Artificial Sequence
```

<220> FEATURE:
<223> OTHER INFORMATION: Synthetic: 28F3 (full length wild-type heavy chain)

<400> SEQUENCE: 29

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
```

-continued 385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 30
<211> LENGTH: 214
<212> TYPE: PRT
<213> ORGANISM: Artificial Sequence
<220> FEATURE:
<223> OTHER INFORMATION: Synthetic: 28F3 (full length wild-type light chain)

<400> SEQUENCE: 30

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 31
<211> LENGTH: 453
<212> TYPE: PRT
<213> ORGANISM: Artificial Sequence
<220> FEATURE:
<223> OTHER INFORMATION: Synthetic: 28F3.IgG1 (VH + IgG1)

<400> SEQUENCE: 31

Gln Val Gln Leu Val Glu Ser Gly Gly Gly Val Val Gln Pro Gly Arg
1 5 10 15

-continued

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly
    450


<210> SEQ ID NO 32
<211> LENGTH: 453
<212> TYPE: PRT
<213> ORGANISM: Artificial Sequence
<220> FEATURE:
<223> OTHER INFORMATION: Synthetic: 28F3.IgG1.1 (VH + IgG1.1)

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 33
<211> LENGTH: 214
<212> TYPE: PRT
<213> ORGANISM: Artificial Sequence
<220> FEATURE:
<223> OTHER INFORMATION: Synthetic: 28F3.IgG1 (VL + CL)

<400> SEQUENCE: 33

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 34
<211> LENGTH: 5
```

<212> TYPE: PRT
<213> ORGANISM: Artificial Sequence
<220> FEATURE:
<223> OTHER INFORMATION: Synthetic: 28F3 VH CDR1

<400> SEQUENCE: 34

Ser Tyr Gly Met His
1 5

<210> SEQ ID NO 35
<211> LENGTH: 17
<212> TYPE: PRT
<213> ORGANISM: Artificial Sequence
<220> FEATURE:
<223> OTHER INFORMATION: Synthetic: 28F3 VH CDR2

<400> SEQUENCE: 35

Val Ile Trp Tyr Glu Gly Ser Asn Lys Tyr Tyr Ala Asp Ser Val Lys
1 5 10 15

Gly

<210> SEQ ID NO 36
<211> LENGTH: 15
<212> TYPE: PRT
<213> ORGANISM: Artificial Sequence
<220> FEATURE:
<223> OTHER INFORMATION: Synthetic: 28F3 VH CDR3

<400> SEQUENCE: 36

Gly Gly Ser Met Val Arg Gly Asp Tyr Tyr Tyr Gly Met Asp Val
1 5 10 15

<210> SEQ ID NO 37
<211> LENGTH: 11
<212> TYPE: PRT
<213> ORGANISM: Artificial Sequence
<220> FEATURE:
<223> OTHER INFORMATION: Synthetic: 28F3 VL CDR1

<400> SEQUENCE: 37

Arg Ala Ser Gln Gly Ile Ser Ser Ala Leu Ala
1 5 10

<210> SEQ ID NO 38
<211> LENGTH: 7
<212> TYPE: PRT
<213> ORGANISM: Artificial Sequence
<220> FEATURE:
<223> OTHER INFORMATION: Synthetic: 28F3 VL CDR2

<400> SEQUENCE: 38

Asp Ala Ser Ser Leu Glu Ser
1 5

<210> SEQ ID NO 39
<211> LENGTH: 9
<212> TYPE: PRT
<213> ORGANISM: Artificial Sequence
<220> FEATURE:
<223> OTHER INFORMATION: Synthetic: 28F3 VL CDR3

<400> SEQUENCE: 39

Gln Gln Phe Asn Ser Tyr Pro Tyr Thr
1 5

<210> SEQ ID NO 40

<211> LENGTH: 449
<212> TYPE: PRT
<213> ORGANISM: Artificial Sequence
<220> FEATURE:
<223> OTHER INFORMATION: Synthetic: 28F3 (VH + G2(C219S)) or 28F3-IgG2-
C219S

<400> SEQUENCE: 40

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

-continued

```
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 41
<211> LENGTH: 450
<212> TYPE: PRT
<213> ORGANISM: Artificial Sequence
<220> FEATURE:
<223> OTHER INFORMATION: Synthetic: 28F3 (VH + G2.g1) or 28F3-IgG2-IgG1

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 42
<211> LENGTH: 449
<212> TYPE: PRT
<213> ORGANISM: Artificial Sequence
<220> FEATURE:
<223> OTHER INFORMATION: Synthetic: 28F3 (VH + G2.g1.1) or 28F3-IgG2-
      IgG1.1

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

```
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 43
<211> LENGTH: 450
<212> TYPE: PRT
<213> ORGANISM: Artificial Sequence
<220> FEATURE:
<223> OTHER INFORMATION: Synthetic: 28F3 (VH + G2(C219S).g1) or 28F3-
      IgG2-C219S-IgG1

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 44
<211> LENGTH: 449
<212> TYPE: PRT
<213> ORGANISM: Artificial Sequence
<220> FEATURE:
<223> OTHER INFORMATION: Synthetic: 28F3 (VH + G2(C219S).g1.1) or 28F3-
IgG2-C219S-IgG1.1

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp

```
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 45
<211> LENGTH: 141
<212> TYPE: PRT
<213> ORGANISM: Artificial Sequence
<220> FEATURE:
<223> OTHER INFORMATION: Synthetic: 28F3 (VH) (SEQ ID NO: 13) with
      signal peptide

<400> SEQUENCE: 45

Met Arg Ala Trp Ile Phe Phe Leu Leu Cys Leu Ala Gly Arg Ala Leu
1               5                   10                  15

Ala Gln Val Gln Leu Val Glu Ser Gly Gly Gly Val Val Gln Pro Gly
            20                  25                  30

Arg Ser Leu Arg Leu Ser Cys Ala Ala Ser Gly Phe Thr Phe Ser Ser
        35                  40                  45

Tyr Gly Met His Trp Val Arg Gln Ala Pro Gly Lys Gly Leu Glu Trp
    50                  55                  60

Val Ala Val Ile Trp Tyr Glu Gly Ser Asn Lys Tyr Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Arg Gly Gly Ser Met Val Arg Gly Asp Tyr Tyr Tyr Gly Met
        115                 120                 125

Asp Val Trp Gly Gln Gly Thr Thr Val Thr Val Ser Ser
    130                 135                 140


<210> SEQ ID NO 46
<211> LENGTH: 124
<212> TYPE: PRT
<213> ORGANISM: Artificial Sequence
<220> FEATURE:
<223> OTHER INFORMATION: Synthetic: 28F3 (VL) (SEQ ID NO: 14) with
      signal peptide

<400> SEQUENCE: 46

Met Arg Ala Trp Ile Phe Phe Leu Leu Cys Leu Ala Gly Arg Ala Leu
1               5                   10                  15

Ala Ala Ile Gln Leu Thr Gln Ser Pro Ser Ser Leu Ser Ala Ser Val
            20                  25                  30

Gly Asp Arg Val Thr Ile Thr Cys Arg Ala Ser Gln Gly Ile Ser Ser
        35                  40                  45

Ala Leu Ala Trp Tyr Gln Gln Lys Pro Gly Lys Ala Pro Lys Leu Leu
    50                  55                  60

Ile Tyr Asp Ala Ser Ser Leu Glu Ser Gly Val Pro Ser Arg Phe Ser
65                  70                  75                  80

Gly Ser Gly Ser Gly Thr Asp Phe Thr Leu Thr Ile Ser Ser Leu Gln
                85                  90                  95

Pro Glu Asp Phe Ala Thr Tyr Tyr Cys Gln Gln Phe Asn Ser Tyr Pro
            100                 105                 110
```

```
Tyr Thr Phe Gly Gln Gly Thr Lys Leu Glu Ile Lys
        115                 120


<210> SEQ ID NO 47
<211> LENGTH: 470
<212> TYPE: PRT
<213> ORGANISM: Artificial Sequence
<220> FEATURE:
<223> OTHER INFORMATION: Synthetic: 28F3.IgG1 (VH + IgG1) with signal
      peptide

<400> SEQUENCE: 47

Met Arg Ala Trp Ile Phe Phe Leu Leu Cys Leu Ala Gly Arg Ala Leu
1               5                   10                  15

Ala Gln Val Gln Leu Val Glu Ser Gly Gly Gly Val Val Gln Pro Gly
            20                  25                  30

Arg Ser Leu Arg Leu Ser Cys Ala Ala Ser Gly Phe Thr Phe Ser Ser
        35                  40                  45

Tyr Gly Met His Trp Val Arg Gln Ala Pro Gly Lys Gly Leu Glu Trp
    50                  55                  60

Val Ala Val Ile Trp Tyr Glu Gly Ser Asn Lys Tyr Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Arg Gly Gly Ser Met Val Arg Gly Asp Tyr Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
```

-continued

```
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470
```

<210> SEQ ID NO 48
<211> LENGTH: 470
<212> TYPE: PRT
<213> ORGANISM: Artificial Sequence
<220> FEATURE:
<223> OTHER INFORMATION: Synthetic: 28F3.IgG1.1 (VH + IgG1.1) with signal peptide

<400> SEQUENCE: 48

```
Met Arg Ala Trp Ile Phe Phe Leu Leu Cys Leu Ala Gly Arg Ala Leu
1               5                   10                  15

Ala Gln Val Gln Leu Val Glu Ser Gly Gly Gly Val Val Gln Pro Gly
            20                  25                  30

Arg Ser Leu Arg Leu Ser Cys Ala Ala Ser Gly Phe Thr Phe Ser Ser
        35                  40                  45

Tyr Gly Met His Trp Val Arg Gln Ala Pro Gly Lys Gly Leu Glu Trp
    50                  55                  60

Val Ala Val Ile Trp Tyr Glu Gly Ser Asn Lys Tyr Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Arg Gly Gly Ser Met Val Arg Gly Asp Tyr Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

-continued

```
Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Glu Gly Ala Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470


<210> SEQ ID NO 49
<211> LENGTH: 231
<212> TYPE: PRT
<213> ORGANISM: Artificial Sequence
<220> FEATURE:
<223> OTHER INFORMATION: Synthetic: 28F3.IgG1 (VL+CL) with signal
      peptide

<400> SEQUENCE: 49

Met Arg Ala Trp Ile Phe Phe Leu Leu Cys Leu Ala Gly Arg Ala Leu
1               5                   10                  15

Ala Ala Ile Gln Leu Thr Gln Ser Pro Ser Ser Leu Ser Ala Ser Val
            20                  25                  30

Gly Asp Arg Val Thr Ile Thr Cys Arg Ala Ser Gln Gly Ile Ser Ser
        35                  40                  45

Ala Leu Ala Trp Tyr Gln Gln Lys Pro Gly Lys Ala Pro Lys Leu Leu
    50                  55                  60

Ile Tyr Asp Ala Ser Ser Leu Glu Ser Gly Val Pro Ser Arg Phe Ser
65                  70                  75                  80

Gly Ser Gly Ser Gly Thr Asp Phe Thr Leu Thr Ile Ser Ser Leu Gln
                85                  90                  95

Pro Glu Asp Phe Ala Thr Tyr Tyr Cys Gln Gln Phe Asn Ser Tyr Pro
            100                 105                 110
```

Tyr Thr Phe Gly Gln Gly Thr Lys Leu Glu Ile Lys Arg Thr Val Ala
115 120 125

Ala Pro Ser Val Phe Ile Phe Pro Pro Ser Asp Glu Gln Leu Lys Ser
130 135 140

Gly Thr Ala Ser Val Val Cys Leu Leu Asn Asn Phe Tyr Pro Arg Glu
145 150 155 160

Ala Lys Val Gln Trp Lys Val Asp Asn Ala Leu Gln Ser Gly Asn Ser
165 170 175

Gln Glu Ser Val Thr Glu Gln Asp Ser Lys Asp Ser Thr Tyr Ser Leu
180 185 190

Ser Ser Thr Leu Thr Leu Ser Lys Ala Asp Tyr Glu Lys His Lys Val
195 200 205

Tyr Ala Cys Glu Val Thr His Gln Gly Leu Ser Ser Pro Val Thr Lys
210 215 220

Ser Phe Asn Arg Gly Glu Cys
225 230

<210> SEQ ID NO 50
<211> LENGTH: 123
<212> TYPE: PRT
<213> ORGANISM: Artificial Sequence
<220> FEATURE:
<223> OTHER INFORMATION: Synthetic: 19D3 (VH)

<400> SEQUENCE: 50

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Phe His Trp Val Arg Gln Ala Pro Gly Lys Gly Leu Glu Trp Val
35 40 45

Ala Val Ile Trp Tyr Ala Gly Ser Asn Lys Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Gln Leu Asp Tyr Tyr Tyr Tyr Tyr Val Met Asp Val
100 105 110

Trp Gly Gln Gly Thr Thr Val Thr Val Ser Ser
115 120

<210> SEQ ID NO 51
<211> LENGTH: 107
<212> TYPE: PRT
<213> ORGANISM: Artificial Sequence
<220> FEATURE:
<223> OTHER INFORMATION: Synthetic: 19D3 (VL)

<400> SEQUENCE: 51

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 52
<211> LENGTH: 449
<212> TYPE: PRT
<213> ORGANISM: Artificial Sequence
<220> FEATURE:
<223> OTHER INFORMATION: Synthetic: 19D3 (full length wild-type heavy
      chain)

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300
```

Val Ser Val Leu Thr Val Val His Gln Asp Trp Leu Asn Gly Lys Glu
305 310 315 320

Tyr Lys Cys Lys Val Ser Asn Lys Gly Leu Pro Ala Pro Ile Glu Lys
325 330 335

Thr Ile Ser Lys Thr Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Met Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 53
<211> LENGTH: 214
<212> TYPE: PRT
<213> ORGANISM: Artificial Sequence
<220> FEATURE:
<223> OTHER INFORMATION: Synthetic: 19D3 (full length wild-type light chain)

<400> SEQUENCE: 53

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

```
Phe Asn Arg Gly Glu Cys
    210


<210> SEQ ID NO 54
<211> LENGTH: 452
<212> TYPE: PRT
<213> ORGANISM: Artificial Sequence
<220> FEATURE:
<223> OTHER INFORMATION: Synthetic: 19D3.IgG1 (VH + IgG1)

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 55
<211> LENGTH: 452
<212> TYPE: PRT
<213> ORGANISM: Artificial Sequence
<220> FEATURE:
<223> OTHER INFORMATION: Synthetic: 19D3.IgG1.1 (VH + IgG1.1)

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
                245                 250                 255
```

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 56
<211> LENGTH: 214
<212> TYPE: PRT
<213> ORGANISM: Artificial Sequence
<220> FEATURE:
<223> OTHER INFORMATION: Synthetic: 19D3.IgG1 (VL + CL)

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 57
<211> LENGTH: 5
<212> TYPE: PRT
<213> ORGANISM: Artificial Sequence
<220> FEATURE:
<223> OTHER INFORMATION: Synthetic: 19D3 VH CDR1

<400> SEQUENCE: 57

Ser Tyr Gly Phe His
1               5


<210> SEQ ID NO 58
<211> LENGTH: 17
<212> TYPE: PRT
<213> ORGANISM: Artificial Sequence
<220> FEATURE:
<223> OTHER INFORMATION: Synthetic: 19D3 VH CDR2

<400> SEQUENCE: 58

Val Ile Trp Tyr Ala Gly Ser Asn Lys Phe Tyr Ala Asp Ser Val Lys
1               5                   10                  15

Gly


<210> SEQ ID NO 59
<211> LENGTH: 14
<212> TYPE: PRT
<213> ORGANISM: Artificial Sequence
<220> FEATURE:
<223> OTHER INFORMATION: Synthetic: 19D3 VH CDR3

<400> SEQUENCE: 59

Gly Gly Gln Leu Asp Tyr Tyr Tyr Tyr Tyr Val Met Asp Val
1               5                   10


<210> SEQ ID NO 60
<211> LENGTH: 11
<212> TYPE: PRT
<213> ORGANISM: Artificial Sequence
<220> FEATURE:
<223> OTHER INFORMATION: Synthetic: 19D3 VL CDR1

<400> SEQUENCE: 60

Arg Ala Ser Gln Gly Ile Ser Ser Trp Leu Ala
1               5                   10


<210> SEQ ID NO 61
<211> LENGTH: 7
<212> TYPE: PRT
<213> ORGANISM: Artificial Sequence
<220> FEATURE:
<223> OTHER INFORMATION: Synthetic: 19D3 VL CDR2

<400> SEQUENCE: 61

Ala Ala Ser Ser Leu Gln Ser
1               5
```

<210> SEQ ID NO 62
<211> LENGTH: 9
<212> TYPE: PRT
<213> ORGANISM: Artificial Sequence
<220> FEATURE:
<223> OTHER INFORMATION: Synthetic: 19D3 VL CDR3

<400> SEQUENCE: 62

Gln Gln Tyr Asn Ser Tyr Pro Tyr Thr
1               5

<210> SEQ ID NO 63
<211> LENGTH: 448
<212> TYPE: PRT
<213> ORGANISM: Artificial Sequence
<220> FEATURE:
<223> OTHER INFORMATION: Synthetic: 19D3 (VH + G2(C219S)) or 19D3-IgG2-
      C219S

<400> SEQUENCE: 63

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
```

```
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 64
<211> LENGTH: 449
<212> TYPE: PRT
<213> ORGANISM: Artificial Sequence
<220> FEATURE:
<223> OTHER INFORMATION: Synthetic: 19D3 (VH + G2.g1) or 19D3-IgG2-IgG1

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
```

```
    210                 215                 220

Cys Cys Val Glu Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 65
<211> LENGTH: 448
<212> TYPE: PRT
<213> ORGANISM: Artificial Sequence
<220> FEATURE:
<223> OTHER INFORMATION: Synthetic: 19D3 (VH + G2.g1.1) or 19D3-IgG2-
      IgG1.1

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
```

-continued

```
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 66
<211> LENGTH: 449
<212> TYPE: PRT
<213> ORGANISM: Artificial Sequence
<220> FEATURE:
<223> OTHER INFORMATION: Synthetic: 19D3 (VH + G2(C219S).g1) or 19D3-
      IgG2-C219S-IgG1

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 67
<211> LENGTH: 448
<212> TYPE: PRT
<213> ORGANISM: Artificial Sequence
<220> FEATURE:
<223> OTHER INFORMATION: Synthetic: 19D3 (VH + G2(C219S).g1.1) or 19D3-IgG2-C219S-IgG1.1

<400> SEQUENCE: 67

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 68
<211> LENGTH: 448
<212> TYPE: PRT
<213> ORGANISM: Artificial Sequence
<220> FEATURE:
<223> OTHER INFORMATION: Synthetic: 19D3 (VH + G2(C219S)) or 19D3-IgG2-
      C219S

<400> SEQUENCE: 68

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

-continued

```
Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 69
<211> LENGTH: 449
<212> TYPE: PRT
<213> ORGANISM: Artificial Sequence
<220> FEATURE:
<223> OTHER INFORMATION: Synthetic: 19D3 (VH + G2.g1) or 19D3-IgG2-IgG1

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 70
<211> LENGTH: 448
<212> TYPE: PRT
<213> ORGANISM: Artificial Sequence
<220> FEATURE:
<223> OTHER INFORMATION: Synthetic: 19D3 (VH + G2.g1.1) or 19D3-IgG2-
      IgG1.1

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Gly Gln Leu Asp Tyr Tyr Tyr Tyr Tyr Val Met Asp Val
100 105 110

Trp Gly Gln Gly Thr Thr Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Asn Phe Gly Thr Gln Thr Tyr Thr Cys Asn Val
195 200 205

Asp His Lys Pro Ser Asn Thr Lys Val Asp Lys Thr Val Glu Arg Lys
210 215 220

Cys Cys Val Glu Cys Pro Pro Cys Pro Ala Pro Pro Val Ala Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 71
<211> LENGTH: 449
<212> TYPE: PRT
<213> ORGANISM: Artificial Sequence
<220> FEATURE:
<223> OTHER INFORMATION: Synthetic: 19D3 (VH + G2(C219S).g1) or 19D3-
IgG2-C219S-IgG1

<400> SEQUENCE: 71

Gln Val Gln Leu Val Glu Ser Gly Gly Gly Val Val Gln Pro Gly Arg
1 5 10 15

```
Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

-continued

```
Glu Ala Leu His Asn His Tyr Thr Gln Lys Ser Leu Ser Leu Ser Pro
        435                 440                 445

Gly


<210> SEQ ID NO 72
<211> LENGTH: 448
<212> TYPE: PRT
<213> ORGANISM: Artificial Sequence
<220> FEATURE:
<223> OTHER INFORMATION: Synthetic: 19D3 (VH + G2(C219S).g1.1) or 19D3-
      IgG2-C219S-IgG1.1

<400> SEQUENCE: 72

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 73
<211> LENGTH: 123
<212> TYPE: PRT
<213> ORGANISM: Artificial Sequence
<220> FEATURE:
<223> OTHER INFORMATION: Synthetic: 18E10 (VH)

<400> SEQUENCE: 73

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser
        115                 120


<210> SEQ ID NO 74
<211> LENGTH: 107
<212> TYPE: PRT
<213> ORGANISM: Artificial Sequence
<220> FEATURE:
<223> OTHER INFORMATION: Synthetic: 18E10 (VL)

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 75
<211> LENGTH: 449
<212> TYPE: PRT
<213> ORGANISM: Artificial Sequence
<220> FEATURE:
<223> OTHER INFORMATION: Synthetic: 18E10 (full length wild-type heavy
      chain)

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
```

```
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 76
<211> LENGTH: 214
<212> TYPE: PRT
<213> ORGANISM: Artificial Sequence
<220> FEATURE:
<223> OTHER INFORMATION: Synthetic: 18E10 (full length wild-type light
      chain)

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 77
<211> LENGTH: 452
<212> TYPE: PRT
<213> ORGANISM: Artificial Sequence
<220> FEATURE:
<223> OTHER INFORMATION: Synthetic: 18E10.IgG1 (VH + IgG1)

<400> SEQUENCE: 77

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
```

```
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 78
<211> LENGTH: 452
<212> TYPE: PRT
<213> ORGANISM: Artificial Sequence
<220> FEATURE:
<223> OTHER INFORMATION: Synthetic: 18E10.IgG1.1 (VH + IgG1.1)

<400> SEQUENCE: 78

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

```
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 79
<211> LENGTH: 214
<212> TYPE: PRT
<213> ORGANISM: Artificial Sequence
<220> FEATURE:
<223> OTHER INFORMATION: Synthetic: 18E10.IgG1 (VL + CL)

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 80
<211> LENGTH: 5
<212> TYPE: PRT
<213> ORGANISM: Artificial Sequence
<220> FEATURE:
<223> OTHER INFORMATION: Synthetic: 18E10 VH CDR1

<400> SEQUENCE: 80

```
Ser Tyr Gly Met His
1               5
```

<210> SEQ ID NO 81
<211> LENGTH: 17
<212> TYPE: PRT
<213> ORGANISM: Artificial Sequence
<220> FEATURE:
<223> OTHER INFORMATION: Synthetic: 18E10 VH CDR2

<400> SEQUENCE: 81

```
Val Ile Trp Tyr Ala Gly Ser Asn Lys Tyr Tyr Ala Asp Ser Val Lys
1               5                   10                  15

Gly
```

<210> SEQ ID NO 82
<211> LENGTH: 14
<212> TYPE: PRT
<213> ORGANISM: Artificial Sequence
<220> FEATURE:
<223> OTHER INFORMATION: Synthetic: 18E10 VH CDR3

<400> SEQUENCE: 82

```
Gly Gly Arg Ile Ala Val Ala Phe Tyr Tyr Ser Met Asp Val
1               5                   10
```

<210> SEQ ID NO 83
<211> LENGTH: 11
<212> TYPE: PRT
<213> ORGANISM: Artificial Sequence
<220> FEATURE:
<223> OTHER INFORMATION: Synthetic: 18E10 VL CDR1

<400> SEQUENCE: 83

```
Arg Ala Ser Gln Gly Ile Ser Ser Trp Leu Ala
1               5                   10
```

<210> SEQ ID NO 84
<211> LENGTH: 7
<212> TYPE: PRT
<213> ORGANISM: Artificial Sequence
<220> FEATURE:
<223> OTHER INFORMATION: Synthetic: 18E10 VL CDR2

<400> SEQUENCE: 84

```
Ala Ala Ser Ser Leu Gln Ser
1               5
```

<210> SEQ ID NO 85
<211> LENGTH: 9
<212> TYPE: PRT

```
<213> ORGANISM: Artificial Sequence
<220> FEATURE:
<223> OTHER INFORMATION: Synthetic: 18E10 VL CDR3

<400> SEQUENCE: 85

Gln Gln Tyr Asn Ser Tyr Pro Tyr Thr
1               5


<210> SEQ ID NO 86
<211> LENGTH: 448
<212> TYPE: PRT
<213> ORGANISM: Artificial Sequence
<220> FEATURE:
<223> OTHER INFORMATION: Synthetic: 18E10 (VH + G2(C219S)) or 18E10-
      IgG2-C219S

<400> SEQUENCE: 86

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320
```

```
Tyr Lys Cys Lys Val Ser Asn Lys Gly Leu Pro Ala Pro Ile Glu Lys
            325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 87
<211> LENGTH: 449
<212> TYPE: PRT
<213> ORGANISM: Artificial Sequence
<220> FEATURE:
<223> OTHER INFORMATION: Synthetic: 18E10 (VH + G2.g1) or 18E10-IgG2-
      IgG1

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Glu Leu Leu Gly Gly
```

225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 88
<211> LENGTH: 448
<212> TYPE: PRT
<213> ORGANISM: Artificial Sequence
<220> FEATURE:
<223> OTHER INFORMATION: Synthetic: 18E10 (VH + G2.g1.1) or 18E10-IgG2-IgG1.1

<400> SEQUENCE: 88

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Ala Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Arg Ile Ala Val Ala Phe Tyr Tyr Ser Met Asp Val
100 105 110

Trp Gly Gln Gly Thr Thr Val Thr Val Ser Ser Ala Ser Thr Lys Gly
115 120 125

Pro Ser Val Phe Pro Leu Ala Pro Cys Ser Arg Ser Thr Ser Glu Ser

```
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 89
<211> LENGTH: 449
<212> TYPE: PRT
<213> ORGANISM: Artificial Sequence
<220> FEATURE:
<223> OTHER INFORMATION: Synthetic: 18E10 (VH + G2(C219S).g1) or 18E10-IgG2-C219S-IgG1

<400> SEQUENCE: 89

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 90

```
<211> LENGTH: 448
<212> TYPE: PRT
<213> ORGANISM: Artificial Sequence
<220> FEATURE:
<223> OTHER INFORMATION: Synthetic: 18E10 (VH + G2(C219S).g1.1) or
      18E10-IgG2-C219S-IgG1.1

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ile Ala Val Ala Phe Tyr Tyr Ser Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Ser Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 91
<211> LENGTH: 117
<212> TYPE: PRT
<213> ORGANISM: Artificial Sequence
<220> FEATURE:
<223> OTHER INFORMATION: Synthetic: 3C3 (VH)

<400> SEQUENCE: 91

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser
        115


<210> SEQ ID NO 92
<211> LENGTH: 107
<212> TYPE: PRT
<213> ORGANISM: Artificial Sequence
<220> FEATURE:
<223> OTHER INFORMATION: Synthetic: 3C3 (VL1)

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 93
<211> LENGTH: 106
<212> TYPE: PRT
<213> ORGANISM: Artificial Sequence
<220> FEATURE:
<223> OTHER INFORMATION: Synthetic: 3C3 (VL2)

<400> SEQUENCE: 93

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Thr
                85                  90                  95

Phe Gly Gln Gly Thr Lys Leu Glu Ile Lys
            100                 105
```

<210> SEQ ID NO 94
<211> LENGTH: 447
<212> TYPE: PRT
<213> ORGANISM: Artificial Sequence
<220> FEATURE:
<223> OTHER INFORMATION: Synthetic: 3C3 (full length wild-type heavy
      chain)

<400> SEQUENCE: 94

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 95
<211> LENGTH: 214
<212> TYPE: PRT
<213> ORGANISM: Artificial Sequence
<220> FEATURE:
<223> OTHER INFORMATION: Synthetic: 3C3 L1 (full length wild-type light chain 1)

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 96
<211> LENGTH: 213
<212> TYPE: PRT
<213> ORGANISM: Artificial Sequence
<220> FEATURE:
<223> OTHER INFORMATION: Synthetic: 3C3 L2 (full length wild-type light
      chain 2)

<400> SEQUENCE: 96

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 97
<211> LENGTH: 446
<212> TYPE: PRT
<213> ORGANISM: Artificial Sequence
```

<220> FEATURE:
<223> OTHER INFORMATION: Synthetic: 3C3.IgG1 (VH + IgG1)

<400> SEQUENCE: 97

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 98
<211> LENGTH: 446
<212> TYPE: PRT
<213> ORGANISM: Artificial Sequence
<220> FEATURE:
<223> OTHER INFORMATION: Synthetic: 3C3.IgG1.1 (VH + IgG1.1)

<400> SEQUENCE: 98

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Thr Trp Ile Arg Gln Pro Pro Gly Lys Gly Leu Glu Trp Ile
35 40 45

Gly Lys Ile Asn His Ser Gly Asn Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Leu Gly Ala Phe Asp Ala Phe Asp Ile Trp Gly Gln Gly Thr Met
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Ala Glu Gly Ala Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 99
<211> LENGTH: 214
<212> TYPE: PRT
<213> ORGANISM: Artificial Sequence
<220> FEATURE:
<223> OTHER INFORMATION: Synthetic: 3C3.IgG1 (VL1 + CL)

<400> SEQUENCE: 99

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 100

<211> LENGTH: 213
<212> TYPE: PRT
<213> ORGANISM: Artificial Sequence
<220> FEATURE:
<223> OTHER INFORMATION: Synthetic: 3C3IgG1.2 (VL2 + CL)

<400> SEQUENCE: 100

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 101
<211> LENGTH: 5
<212> TYPE: PRT
<213> ORGANISM: Artificial Sequence
<220> FEATURE:
<223> OTHER INFORMATION: Synthetic: 3C3 VH CDR1

<400> SEQUENCE: 101

```
Gly Tyr Tyr Trp Thr
1               5
```

<210> SEQ ID NO 102
<211> LENGTH: 16
<212> TYPE: PRT
<213> ORGANISM: Artificial Sequence
<220> FEATURE:
<223> OTHER INFORMATION: Synthetic: 3C3 VH CDR2

<400> SEQUENCE: 102

```
Lys Ile Asn His Ser Gly Asn Thr Asn Tyr Asn Pro Ser Leu Lys Ser
1               5                   10                  15
```

<210> SEQ ID NO 103
<211> LENGTH: 9

<212> TYPE: PRT
<213> ORGANISM: Artificial Sequence
<220> FEATURE:
<223> OTHER INFORMATION: Synthetic: 3C3 VH CDR3

<400> SEQUENCE: 103

Leu Gly Ala Phe Asp Ala Phe Asp Ile
1 5

<210> SEQ ID NO 104
<211> LENGTH: 11
<212> TYPE: PRT
<213> ORGANISM: Artificial Sequence
<220> FEATURE:
<223> OTHER INFORMATION: Synthetic: 3C3 VL1 CDR1

<400> SEQUENCE: 104

Arg Ala Ser Gln Gly Ile Ser Ser Trp Leu Ala
1 5 10

<210> SEQ ID NO 105
<211> LENGTH: 7
<212> TYPE: PRT
<213> ORGANISM: Artificial Sequence
<220> FEATURE:
<223> OTHER INFORMATION: Synthetic: 3C3 VL1 CDR2

<400> SEQUENCE: 105

Ala Ala Ser Ser Leu Gln Ser
1 5

<210> SEQ ID NO 106
<211> LENGTH: 9
<212> TYPE: PRT
<213> ORGANISM: Artificial Sequence
<220> FEATURE:
<223> OTHER INFORMATION: Synthetic: 3C3 VL1 CDR3

<400> SEQUENCE: 106

Gln Gln Tyr Asn Ser Tyr Pro Tyr Thr
1 5

<210> SEQ ID NO 107
<211> LENGTH: 11
<212> TYPE: PRT
<213> ORGANISM: Artificial Sequence
<220> FEATURE:
<223> OTHER INFORMATION: Synthetic: 3C3 VL2 CDR1

<400> SEQUENCE: 107

Arg Ala Ser Gln Gly Val Ser Ser Tyr Leu Ala
1 5 10

<210> SEQ ID NO 108
<211> LENGTH: 7
<212> TYPE: PRT
<213> ORGANISM: Artificial Sequence
<220> FEATURE:
<223> OTHER INFORMATION: Synthetic: 3C3 VL2 CDR2

<400> SEQUENCE: 108

Asp Ala Ser Asn Arg Ala Thr
1 5

<210> SEQ ID NO 109
<211> LENGTH: 8
<212> TYPE: PRT

<213> ORGANISM: Artificial Sequence
<220> FEATURE:
<223> OTHER INFORMATION: Synthetic: 3C3 VL2 CDR3

<400> SEQUENCE: 109

Gln Gln Arg Ser Asn Trp His Thr
1               5

<210> SEQ ID NO 110
<211> LENGTH: 442
<212> TYPE: PRT
<213> ORGANISM: Artificial Sequence
<220> FEATURE:
<223> OTHER INFORMATION: Synthetic: 3C3 (VH + G2) or 3C3-IgG2

<400> SEQUENCE: 110

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

```
Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440


<210> SEQ ID NO 111
<211> LENGTH: 442
<212> TYPE: PRT
<213> ORGANISM: Artificial Sequence
<220> FEATURE:
<223> OTHER INFORMATION: Synthetic: 3C3 (VH + G2(C219S)) or 3C3-IgG2-
      C219S

<400> SEQUENCE: 111

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240
```

```
Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly
    435                 440


<210> SEQ ID NO 112
<211> LENGTH: 443
<212> TYPE: PRT
<213> ORGANISM: Artificial Sequence
<220> FEATURE:
<223> OTHER INFORMATION: Synthetic: 3C3 (VH + G2.g1) or 3C3-IgG2-IgG1

<400> SEQUENCE: 112

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 113
<211> LENGTH: 442
<212> TYPE: PRT
<213> ORGANISM: Artificial Sequence
<220> FEATURE:
<223> OTHER INFORMATION: Synthetic: 3C3 (VH + G2.g1.1) or 3C3-IgG2-
      IgG1.1

<400> SEQUENCE: 113

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu

-continued

```
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440


<210> SEQ ID NO 114
<211> LENGTH: 443
<212> TYPE: PRT
<213> ORGANISM: Artificial Sequence
<220> FEATURE:
<223> OTHER INFORMATION: Synthetic: 3C3 (VH + G2(C219S).g1) or 3C3-IgG2-
      C219S-IgG1
```

<400> SEQUENCE: 114

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
```

-continued

```
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 115
<211> LENGTH: 442
<212> TYPE: PRT
<213> ORGANISM: Artificial Sequence
<220> FEATURE:
<223> OTHER INFORMATION: Synthetic: 3C3 (VH + G2(C219S).g1.1) or 3C3-
      IgG2-C219S-IgG1.1

<400> SEQUENCE: 115

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Lys Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Ala Phe Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320
```

```
Asn Lys Ala Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440


<210> SEQ ID NO 116
<211> LENGTH: 124
<212> TYPE: PRT
<213> ORGANISM: Artificial Sequence
<220> FEATURE:
<223> OTHER INFORMATION: Synthetic: 2G6 (VH)

<400> SEQUENCE: 116

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser
        115                 120


<210> SEQ ID NO 117
<211> LENGTH: 107
<212> TYPE: PRT
<213> ORGANISM: Artificial Sequence
<220> FEATURE:
<223> OTHER INFORMATION: Synthetic: 2G6 (VL)

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 118
<211> LENGTH: 450
<212> TYPE: PRT
<213> ORGANISM: Artificial Sequence
<220> FEATURE:
<223> OTHER INFORMATION: Synthetic: 2G6 (full length wild-type heavy
      chain)

<400> SEQUENCE: 118

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
```

```
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 119
<211> LENGTH: 214
<212> TYPE: PRT
<213> ORGANISM: Artificial Sequence
<220> FEATURE:
<223> OTHER INFORMATION: Synthetic: 2G6 (full length wild-type light
      chain)

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 120
<211> LENGTH: 453
<212> TYPE: PRT
<213> ORGANISM: Artificial Sequence
<220> FEATURE:
<223> OTHER INFORMATION: Synthetic: 2G6.IgG1 (VH + IgG1)

<400> SEQUENCE: 120

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

-continued

```
Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 121
<211> LENGTH: 453
<212> TYPE: PRT
<213> ORGANISM: Artificial Sequence
<220> FEATURE:
<223> OTHER INFORMATION: Synthetic: 2G6.IgG1.1 (VH + IgG1.1)

<400> SEQUENCE: 121

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 122
<211> LENGTH: 214
<212> TYPE: PRT
<213> ORGANISM: Artificial Sequence
<220> FEATURE:
<223> OTHER INFORMATION: Synthetic: 2G6.IgG1 (VL + CL)

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 123
<211> LENGTH: 5
<212> TYPE: PRT
<213> ORGANISM: Artificial Sequence
<220> FEATURE:
<223> OTHER INFORMATION: Synthetic: 2G6 VH CDR1

<400> SEQUENCE: 123

Asp Tyr Gly Met His
1               5


<210> SEQ ID NO 124
<211> LENGTH: 17
<212> TYPE: PRT
<213> ORGANISM: Artificial Sequence
<220> FEATURE:
<223> OTHER INFORMATION: Synthetic: 2G6 VH CDR2

<400> SEQUENCE: 124

Val Ile Trp Tyr Asp Gly Ser Asn Lys Phe Tyr Val Asp Ser Val Lys
1               5                   10                  15

Gly


<210> SEQ ID NO 125
<211> LENGTH: 15
<212> TYPE: PRT
<213> ORGANISM: Artificial Sequence
<220> FEATURE:
<223> OTHER INFORMATION: Synthetic: 2G6 VH CDR3

<400> SEQUENCE: 125

Gly Gly Arg Leu Ala Thr Gly His Phe Tyr Tyr Val Met Asp Val
1               5                   10                  15


<210> SEQ ID NO 126
<211> LENGTH: 11
<212> TYPE: PRT
<213> ORGANISM: Artificial Sequence
<220> FEATURE:
<223> OTHER INFORMATION: Synthetic: 2G6 VL CDR1

<400> SEQUENCE: 126

Arg Ala Ser Gln Gly Ile Ser Ser Trp Leu Ala
1               5                   10


<210> SEQ ID NO 127
<211> LENGTH: 7
<212> TYPE: PRT
<213> ORGANISM: Artificial Sequence
<220> FEATURE:
<223> OTHER INFORMATION: Synthetic: 2G6 VL CDR2

<400> SEQUENCE: 127

Ala Ala Ser Ser Leu Gln Ser
1               5
```

<210> SEQ ID NO 128
<211> LENGTH: 9
<212> TYPE: PRT
<213> ORGANISM: Artificial Sequence
<220> FEATURE:
<223> OTHER INFORMATION: Synthetic: 2G6 VL CDR3

<400> SEQUENCE: 128

Gln Gln Tyr Asn Ser Tyr Pro Tyr Thr
1               5

<210> SEQ ID NO 129
<211> LENGTH: 449
<212> TYPE: PRT
<213> ORGANISM: Artificial Sequence
<220> FEATURE:
<223> OTHER INFORMATION: Synthetic: 2G6 (VH + G2) or 2G6-IgG2

<400> SEQUENCE: 129

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300
```

```
Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 130
<211> LENGTH: 449
<212> TYPE: PRT
<213> ORGANISM: Artificial Sequence
<220> FEATURE:
<223> OTHER INFORMATION: Synthetic: 2G6 (VH + G2(C219S)) or2G6-IgG2-
      C219S

<400> SEQUENCE: 130

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205
```

```
Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 131
<211> LENGTH: 450
<212> TYPE: PRT
<213> ORGANISM: Artificial Sequence
<220> FEATURE:
<223> OTHER INFORMATION: Synthetic: 2G6 (VH + G2.g1) or2G6-IgG2-IgG1

<400> SEQUENCE: 131

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110
```

```
Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 132
<211> LENGTH: 449
<212> TYPE: PRT
<213> ORGANISM: Artificial Sequence
<220> FEATURE:
<223> OTHER INFORMATION: Synthetic: 2G6  (VH + G2.g1.1) or2G6-IgG2-
      IgG1.1

<400> SEQUENCE: 132

Gln Val Gln Leu Val Glu Ser Gly Gly Gly Val Val Gln Pro Gly Gly
1               5                   10                  15
```

-continued

```
Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly


<210> SEQ ID NO 133
<211> LENGTH: 450
<212> TYPE: PRT
<213> ORGANISM: Artificial Sequence
<220> FEATURE:
<223> OTHER INFORMATION: Synthetic: 2G6 (VH + G2(C219S).g1) or 2G6-IgG2-
      C219S-IgG1

<400> SEQUENCE: 133

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 134
<211> LENGTH: 449
<212> TYPE: PRT
<213> ORGANISM: Artificial Sequence
<220> FEATURE:
<223> OTHER INFORMATION: Synthetic: 2G6 (VH + G2(C219S).g1.1) or2G6-
      IgG2-C219S-IgG1.1

<400> SEQUENCE: 134

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Leu Ser Asp Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Gly Arg Leu Ala Thr Gly His Phe Tyr Tyr Val Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 135
<211> LENGTH: 124
<212> TYPE: PRT
<213> ORGANISM: Artificial Sequence
<220> FEATURE:
<223> OTHER INFORMATION: Synthetic: 8A6 (VH)

<400> SEQUENCE: 135

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser
        115                 120


<210> SEQ ID NO 136
<211> LENGTH: 107
```

<212> TYPE: PRT
<213> ORGANISM: Artificial Sequence
<220> FEATURE:
<223> OTHER INFORMATION: Synthetic: 8A6 (VL)

<400> SEQUENCE: 136

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105
```

<210> SEQ ID NO 137
<211> LENGTH: 450
<212> TYPE: PRT
<213> ORGANISM: Artificial Sequence
<220> FEATURE:
<223> OTHER INFORMATION: Synthetic: 8A6 (full length wild-type heavy chain)

<400> SEQUENCE: 137

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
```

```
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 138
<211> LENGTH: 214
<212> TYPE: PRT
<213> ORGANISM: Artificial Sequence
<220> FEATURE:
<223> OTHER INFORMATION: Synthetic: 8A6 (full length wild-type light
      chain)

<400> SEQUENCE: 138

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 139
<211> LENGTH: 453
<212> TYPE: PRT
<213> ORGANISM: Artificial Sequence
<220> FEATURE:
<223> OTHER INFORMATION: Synthetic: 8A6.IgG1 (VH + IgG1)

<400> SEQUENCE: 139

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

-continued

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 140
<211> LENGTH: 453
<212> TYPE: PRT
<213> ORGANISM: Artificial Sequence
<220> FEATURE:
<223> OTHER INFORMATION: Synthetic: 8A6.IgG1.1 (VH + IgG1.1)

<400> SEQUENCE: 140

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160
```

-continued

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 141
<211> LENGTH: 214
<212> TYPE: PRT
<213> ORGANISM: Artificial Sequence
<220> FEATURE:
<223> OTHER INFORMATION: Synthetic: 8A6.IgG1 (VL + CL)

<400> SEQUENCE: 141

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60
```

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 142
<211> LENGTH: 5
<212> TYPE: PRT
<213> ORGANISM: Artificial Sequence
<220> FEATURE:
<223> OTHER INFORMATION: Synthetic: 8A6 VH CDR1

<400> SEQUENCE: 142

Ser Tyr Gly Met Gln
1 5

<210> SEQ ID NO 143
<211> LENGTH: 17
<212> TYPE: PRT
<213> ORGANISM: Artificial Sequence
<220> FEATURE:
<223> OTHER INFORMATION: Synthetic: 8A6 VH CDR2

<400> SEQUENCE: 143

Val Ile Trp Tyr Glu Gly Ser Asn Lys Tyr Tyr Ala Asp Ser Val Lys
1 5 10 15

Gly

<210> SEQ ID NO 144
<211> LENGTH: 15
<212> TYPE: PRT
<213> ORGANISM: Artificial Sequence
<220> FEATURE:
<223> OTHER INFORMATION: Synthetic: 8A6 VH CDR3

<400> SEQUENCE: 144

Gly Gly Leu Met Val Arg Gly Leu Phe Tyr Tyr Gly Met Asp Val
1 5 10 15

<210> SEQ ID NO 145
<211> LENGTH: 11
<212> TYPE: PRT
<213> ORGANISM: Artificial Sequence
<220> FEATURE:
<223> OTHER INFORMATION: Synthetic: 8A6 VL CDR1

<400> SEQUENCE: 145

Arg Ala Ser Gln Gly Ile Ser Ser Ala Leu Ala
1 5 10

<210> SEQ ID NO 146
<211> LENGTH: 7
<212> TYPE: PRT
<213> ORGANISM: Artificial Sequence
<220> FEATURE:
<223> OTHER INFORMATION: Synthetic: 8A6 VL CDR2

<400> SEQUENCE: 146

Asp Ala Ser Ser Leu Glu Ser
1 5

<210> SEQ ID NO 147
<211> LENGTH: 9
<212> TYPE: PRT
<213> ORGANISM: Artificial Sequence
<220> FEATURE:
<223> OTHER INFORMATION: Synthetic: 8A6 VL CDR3

<400> SEQUENCE: 147

Gln Gln Phe Asn Ser Tyr Pro Tyr Thr
1 5

<210> SEQ ID NO 148
<211> LENGTH: 449
<212> TYPE: PRT
<213> ORGANISM: Artificial Sequence
<220> FEATURE:
<223> OTHER INFORMATION: Synthetic: 8A6 (VH + G2(C219S)) or 8A6-IgG2-
C219S

<400> SEQUENCE: 148

Gln Val Gln Leu Val Glu Ser Gly Gly Gly Val Val Gln Pro Gly Arg
1 5 10 15

Ser Leu Arg Leu Ser Cys Thr Ala Ser Gly Phe Thr Phe Ser Ser Tyr
20 25 30

Gly Met Gln Trp Val Arg Gln Ala Pro Gly Lys Gly Leu Glu Trp Val
35 40 45

Ala Val Ile Trp Tyr Glu Gly Ser Asn Lys Tyr Tyr Ala Asp Ser Val
50 55 60

Lys Gly Arg Phe Thr Ile Ser Arg Glu Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Leu Met Val Arg Gly Leu Phe Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Asn Phe Gly Thr Gln Thr Tyr Thr Cys Asn

-continued

```
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 149
<211> LENGTH: 450
<212> TYPE: PRT
<213> ORGANISM: Artificial Sequence
<220> FEATURE:
<223> OTHER INFORMATION: Synthetic: 8A6 (VH + G2.g1) or 8A6 -IgG2-IgG1

<400> SEQUENCE: 149

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110
```

```
Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 150
<211> LENGTH: 449
<212> TYPE: PRT
<213> ORGANISM: Artificial Sequence
<220> FEATURE:
<223> OTHER INFORMATION: Synthetic: 8A6 (VH + G2.g1.1) or 8A6 -IgG2-
      IgG1.1

<400> SEQUENCE: 150

Gln Val Gln Leu Val Glu Ser Gly Gly Gly Val Val Gln Pro Gly Arg
```

-continued

```
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly


<210> SEQ ID NO 151
<211> LENGTH: 450
<212> TYPE: PRT
<213> ORGANISM: Artificial Sequence
<220> FEATURE:
<223> OTHER INFORMATION: Synthetic: 8A6 (VH + G2(C219S).g1) or 8A6-IgG2-
      C219S-IgG1

<400> SEQUENCE: 151

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 152
<211> LENGTH: 449
<212> TYPE: PRT
<213> ORGANISM: Artificial Sequence
<220> FEATURE:
<223> OTHER INFORMATION: Synthetic: 8A6 (VH + G2(C219S).g1.1) or 8A6-
      IgG2-C219S-IgG1.1

<400> SEQUENCE: 152

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Met Val Arg Gly Leu Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
```

```
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 153
<211> LENGTH: 125
<212> TYPE: PRT
<213> ORGANISM: Artificial Sequence
<220> FEATURE:
<223> OTHER INFORMATION: Synthetic: 9G7 (VH)

<400> SEQUENCE: 153

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser
        115                 120                 125


<210> SEQ ID NO 154
```

<211> LENGTH: 108
<212> TYPE: PRT
<213> ORGANISM: Artificial Sequence
<220> FEATURE:
<223> OTHER INFORMATION: Synthetic: 9G7 (VL1)

<400> SEQUENCE: 154

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 155
<211> LENGTH: 108
<212> TYPE: PRT
<213> ORGANISM: Artificial Sequence
<220> FEATURE:
<223> OTHER INFORMATION: Synthetic: 9G7 (VL2)

<400> SEQUENCE: 155

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Glu Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Ile Thr Phe Gly Gln Gly Thr Arg Leu Glu Ile Lys
100 105

<210> SEQ ID NO 156
<211> LENGTH: 452
<212> TYPE: PRT
<213> ORGANISM: Artificial Sequence
<220> FEATURE:
<223> OTHER INFORMATION: Synthetic: 9G7 (full length wild-type heavy chain)

<400> SEQUENCE: 156

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Val
20 25 30

Trp Met Ser Trp Val Arg Gln Ala Pro Gly Lys Gly Leu Glu Trp Val
35 40 45

-continued

```
Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 157
<211> LENGTH: 215
<212> TYPE: PRT
<213> ORGANISM: Artificial Sequence
<220> FEATURE:
<223> OTHER INFORMATION: Synthetic: 9G7 L2 (full length wild-type light chain 2)

<400> SEQUENCE: 157

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Glu Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 158
<211> LENGTH: 454
<212> TYPE: PRT
<213> ORGANISM: Artificial Sequence
<220> FEATURE:
<223> OTHER INFORMATION: Synthetic: 9G7.IgG1 (VH + IgG1)

<400> SEQUENCE: 158

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
```

-continued

```
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 159
<211> LENGTH: 454
<212> TYPE: PRT
<213> ORGANISM: Artificial Sequence
<220> FEATURE:
<223> OTHER INFORMATION: Synthetic: 9G7.IgG1.1 (VH + IgG1.1)

<400> SEQUENCE: 159

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Val
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu His Thr Glu Asp Thr Ala Val Tyr
85 90 95

Tyr Cys Thr Thr Gly Gln Leu Ile Pro Tyr Ser Tyr Tyr Tyr Gly Met
100 105 110

Asp Val Trp Gly Gln Gly Thr Ser Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

```
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 160
<211> LENGTH: 215
<212> TYPE: PRT
<213> ORGANISM: Artificial Sequence
<220> FEATURE:
<223> OTHER INFORMATION: Synthetic: 9G7.IgG1 (VL1 + CL)

<400> SEQUENCE: 160

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 161
<211> LENGTH: 215
<212> TYPE: PRT
<213> ORGANISM: Artificial Sequence
<220> FEATURE:
<223> OTHER INFORMATION: Synthetic: 9G7.IgG1.2 (VL2 + CL)

<400> SEQUENCE: 161

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
```

35 40 45

Ile Tyr Gly Ala Ser Ser Arg Ala Thr Gly Ile Pro Glu Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Ile Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 162
<211> LENGTH: 5
<212> TYPE: PRT
<213> ORGANISM: Artificial Sequence
<220> FEATURE:
<223> OTHER INFORMATION: Synthetic: 9G7 VH CDR1

<400> SEQUENCE: 162

Thr Val Trp Met Ser
1 5

<210> SEQ ID NO 163
<211> LENGTH: 19
<212> TYPE: PRT
<213> ORGANISM: Artificial Sequence
<220> FEATURE:
<223> OTHER INFORMATION: Synthetic: 9G7 VH CDR2

<400> SEQUENCE: 163

Arg Ile Lys Ser Lys Thr Asp Gly Gly Thr Thr Asp Tyr Ala Ala Pro
1 5 10 15

Val Lys Gly

<210> SEQ ID NO 164
<211> LENGTH: 14
<212> TYPE: PRT
<213> ORGANISM: Artificial Sequence
<220> FEATURE:
<223> OTHER INFORMATION: Synthetic: 9G7 VH CDR3

<400> SEQUENCE: 164

Gly Gln Leu Ile Pro Tyr Ser Tyr Tyr Tyr Gly Met Asp Val
1 5 10

<210> SEQ ID NO 165
<211> LENGTH: 12

<212> TYPE: PRT
<213> ORGANISM: Artificial Sequence
<220> FEATURE:
<223> OTHER INFORMATION: Synthetic: 9G7 VL1 CDR1

<400> SEQUENCE: 165

Arg Ala Ser Gln Ser Val Ser Ser Ser Tyr Leu Ala
1 5 10

<210> SEQ ID NO 166
<211> LENGTH: 7
<212> TYPE: PRT
<213> ORGANISM: Artificial Sequence
<220> FEATURE:
<223> OTHER INFORMATION: Synthetic: 9G7 VL1 CDR2

<400> SEQUENCE: 166

Gly Ala Ser Ser Arg Ala Thr
1 5

<210> SEQ ID NO 167
<211> LENGTH: 9
<212> TYPE: PRT
<213> ORGANISM: Artificial Sequence
<220> FEATURE:
<223> OTHER INFORMATION: Synthetic: 9G7 VL1 CDR3

<400> SEQUENCE: 167

Gln Gln Tyr Gly Ser Ser Pro Trp Thr
1 5

<210> SEQ ID NO 168
<211> LENGTH: 12
<212> TYPE: PRT
<213> ORGANISM: Artificial Sequence
<220> FEATURE:
<223> OTHER INFORMATION: Synthetic: 9G7 VL2 CDR1

<400> SEQUENCE: 168

Arg Ala Ser Gln Ser Val Thr Ser Ser Tyr Leu Ala
1 5 10

<210> SEQ ID NO 169
<211> LENGTH: 7
<212> TYPE: PRT
<213> ORGANISM: Artificial Sequence
<220> FEATURE:
<223> OTHER INFORMATION: Synthetic: 9G7 VL2 CDR2

<400> SEQUENCE: 169

Gly Ala Ser Ser Arg Ala Thr
1 5

<210> SEQ ID NO 170
<211> LENGTH: 9
<212> TYPE: PRT
<213> ORGANISM: Artificial Sequence
<220> FEATURE:
<223> OTHER INFORMATION: Synthetic: 9G7 VL2 CDR3

<400> SEQUENCE: 170

Gln Gln Tyr Gly Ser Ser Pro Ile Thr
1 5

<210> SEQ ID NO 171
<211> LENGTH: 450
<212> TYPE: PRT

-continued

<213> ORGANISM: Artificial Sequence
<220> FEATURE:
<223> OTHER INFORMATION: Synthetic: 9G7 (VH + G2) or 9G7-IgG2

<400> SEQUENCE: 171

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 172
<211> LENGTH: 450
<212> TYPE: PRT
<213> ORGANISM: Artificial Sequence
<220> FEATURE:
<223> OTHER INFORMATION: Synthetic: 9G7 (VH + G2(C219S)) or 9G7-IgG2-
      C219S

<400> SEQUENCE: 172

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Ser Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285
```

His Asn Ala Lys Thr Lys Pro Arg Glu Glu Gln Phe Asn Ser Thr Phe
290 295 300

Arg Val Val Ser Val Leu Thr Val Val His Gln Asp Trp Leu Asn Gly
305 310 315 320

Lys Glu Tyr Lys Cys Lys Val Ser Asn Lys Gly Leu Pro Ala Pro Ile
325 330 335

Glu Lys Thr Ile Ser Lys Thr Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Met Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 173
<211> LENGTH: 451
<212> TYPE: PRT
<213> ORGANISM: Artificial Sequence
<220> FEATURE:
<223> OTHER INFORMATION: Synthetic: 9G7 (VH + G2.g1) or 9G7-IgG2-IgG1

<400> SEQUENCE: 173

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Val
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu His Thr Glu Asp Thr Ala Val Tyr
85 90 95

Tyr Cys Thr Thr Gly Gln Leu Ile Pro Tyr Ser Tyr Tyr Tyr Gly Met
100 105 110

Asp Val Trp Gly Gln Gly Thr Ser Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Asn Phe Gly Thr Gln Thr Tyr Thr Cys
195 200 205

Asn Val Asp His Lys Pro Ser Asn Thr Lys Val Asp Lys Thr Val Glu
210 215 220

Arg Lys Cys Cys Val Glu Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly
450

<210> SEQ ID NO 174
<211> LENGTH: 450
<212> TYPE: PRT
<213> ORGANISM: Artificial Sequence
<220> FEATURE:
<223> OTHER INFORMATION: Synthetic: 9G7 (VH + G2.g1.1) or 9G7-IgG2-IgG1.1

<400> SEQUENCE: 174

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Val
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu His Thr Glu Asp Thr Ala Val Tyr
85 90 95

```
Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 175
<211> LENGTH: 451
<212> TYPE: PRT
<213> ORGANISM: Artificial Sequence
<220> FEATURE:
<223> OTHER INFORMATION: Synthetic: 9G7 (VH + G2(C219S).g1) or 9G7-IgG2-
C219S-IgG1

<400> SEQUENCE: 175

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Ser Cys Val Glu Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 176
<211> LENGTH: 450
<212> TYPE: PRT
<213> ORGANISM: Artificial Sequence
<220> FEATURE:
<223> OTHER INFORMATION: Synthetic: 9G7 (VH + G2(C219S).g1.1) or 9G7-
      IgG2-C219S-IgG1.1

<400> SEQUENCE: 176

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Val
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu His Thr Glu Asp Thr Ala Val Tyr
                85                  90                  95

Tyr Cys Thr Thr Gly Gln Leu Ile Pro Tyr Ser Tyr Tyr Tyr Gly Met
            100                 105                 110

Asp Val Trp Gly Gln Gly Thr Ser Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Ser Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 177
<211> LENGTH: 215
<212> TYPE: PRT
<213> ORGANISM: Artificial Sequence
<220> FEATURE:
<223> OTHER INFORMATION: Synthetic: 9G7 L1 (full length wild-type light
      chain 1)

<400> SEQUENCE: 177

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215


<210> SEQ ID NO 178
<211> LENGTH: 117
<212> TYPE: PRT
<213> ORGANISM: Artificial Sequence
<220> FEATURE:
<223> OTHER INFORMATION: Synthetic: 14E3 (VH)

<400> SEQUENCE: 178

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser
        115


<210> SEQ ID NO 179
<211> LENGTH: 107
<212> TYPE: PRT
<213> ORGANISM: Artificial Sequence
<220> FEATURE:
<223> OTHER INFORMATION: Synthetic: 14E3 (VL)

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105


<210> SEQ ID NO 180
<211> LENGTH: 447
<212> TYPE: PRT
<213> ORGANISM: Artificial Sequence
<220> FEATURE:
<223> OTHER INFORMATION: Synthetic: 14E3 (full length wild-type heavy
      chain)

<400> SEQUENCE: 180
```

-continued

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

```
            420                 425                 430

His Asn His Tyr Thr Gln Lys Ser Leu Ser Leu Ser Pro Gly Lys
        435                 440                 445


<210> SEQ ID NO 181
<211> LENGTH: 214
<212> TYPE: PRT
<213> ORGANISM: Artificial Sequence
<220> FEATURE:
<223> OTHER INFORMATION: Synthetic: 14E3 (full length wild-type light
      chain)

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 182
<211> LENGTH: 446
<212> TYPE: PRT
<213> ORGANISM: Artificial Sequence
<220> FEATURE:
<223> OTHER INFORMATION: Synthetic: 14E3.IgG1 (VH + IgG1)

<400> SEQUENCE: 182

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Tyr Tyr Asn Pro Ser Leu Lys
    50                  55                  60
```

```
Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 183
<211> LENGTH: 446
<212> TYPE: PRT
<213> ORGANISM: Artificial Sequence
<220> FEATURE:

-continued

<223> OTHER INFORMATION: Synthetic: 14E3.IgG1.1 (VH + IgG1.1)

<400> SEQUENCE: 183

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 184
<211> LENGTH: 214
<212> TYPE: PRT
<213> ORGANISM: Artificial Sequence
<220> FEATURE:
<223> OTHER INFORMATION: Synthetic: 14E3.IgG1 (VL + CL)

<400> SEQUENCE: 184

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 185
<211> LENGTH: 5
<212> TYPE: PRT
<213> ORGANISM: Artificial Sequence
<220> FEATURE:
<223> OTHER INFORMATION: Synthetic: 14E3 VH CDR1

<400> SEQUENCE: 185

Gly Tyr Tyr Trp Ser
1 5

<210> SEQ ID NO 186
<211> LENGTH: 16
<212> TYPE: PRT
<213> ORGANISM: Artificial Sequence
<220> FEATURE:
<223> OTHER INFORMATION: Synthetic: 14E3 VH CDR2

<400> SEQUENCE: 186

Glu Ile Asn His Ser Gly Asn Thr Tyr Tyr Asn Pro Ser Leu Lys Ser
1               5                   10                  15

<210> SEQ ID NO 187
<211> LENGTH: 9
<212> TYPE: PRT
<213> ORGANISM: Artificial Sequence
<220> FEATURE:
<223> OTHER INFORMATION: Synthetic: 14E3 VH CDR3

<400> SEQUENCE: 187

Phe Gly Ser Asn Asp Ala Phe Asp Ile
1               5

<210> SEQ ID NO 188
<211> LENGTH: 11
<212> TYPE: PRT
<213> ORGANISM: Artificial Sequence
<220> FEATURE:
<223> OTHER INFORMATION: Synthetic: 14E3 VL CDR1

<400> SEQUENCE: 188

Arg Ala Ser Gln Gly Ile Ser Ser Trp Leu Ala
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Synthetic: 14E3 VL CDR2

<400> SEQUENCE: 189

Ala Ala Ser Ser Leu Gln Ser
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic: 14E3 VL CDR3

<400> SEQUENCE: 190

Gln Gln Tyr Asn Ser Tyr Pro Pro Thr
1               5

<210> SEQ ID NO 191
<211> LENGTH: 442
<212> TYPE: PRT
<213> ORGANISM: Artificial Sequence
<220> FEATURE:
<223> OTHER INFORMATION: Synthetic: 14E3 (VH + G2) or 14E3-IgG2

<400> SEQUENCE: 191

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

```
Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440
```

<210> SEQ ID NO 192
<211> LENGTH: 442
<212> TYPE: PRT

<213> ORGANISM: Artificial Sequence
<220> FEATURE:
<223> OTHER INFORMATION: Synthetic: 14E3 (VH + G2(C219S)) or 14E3-IgG2-C219S

<400> SEQUENCE: 192

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380
```

-continued

Asn Asn Tyr Lys Thr Thr Pro Pro Met Leu Asp Ser Asp Gly Ser Phe
385 390 395 400

Phe Leu Tyr Ser Lys Leu Thr Val Asp Lys Ser Arg Trp Gln Gln Gly
405 410 415

Asn Val Phe Ser Cys Ser Val Met His Glu Ala Leu His Asn His Tyr
420 425 430

Thr Gln Lys Ser Leu Ser Leu Ser Pro Gly
435 440

<210> SEQ ID NO 193
<211> LENGTH: 443
<212> TYPE: PRT
<213> ORGANISM: Artificial Sequence
<220> FEATURE:
<223> OTHER INFORMATION: Synthetic: 14E3 (VH + G2.g1) or 14E3-IgG2-IgG1

<400> SEQUENCE: 193

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Asn Thr Tyr Tyr Asn Pro Ser Leu Lys
50 55 60

Ser Arg Val Thr Ile Ser Val Asp Thr Ser Lys Asn Gln Leu Ser Leu
65 70 75 80

Lys Leu Ser Ser Val Thr Ala Ala Asp Thr Ala Val Tyr Tyr Cys Ala
85 90 95

Arg Phe Gly Ser Asn Asp Ala Phe Asp Ile Trp Gly Gln Gly Thr Met
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Asn
180 185 190

Phe Gly Thr Gln Thr Tyr Thr Cys Asn Val Asp His Lys Pro Ser Asn
195 200 205

Thr Lys Val Asp Lys Thr Val Glu Arg Lys Cys Cys Val Glu Cys Pro
210 215 220

Pro Cys Pro Ala Pro Glu Leu Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser His Glu Asp Pro Glu Val Lys Phe
260 265 270

Asn Trp Tyr Val Asp Gly Val Glu Val His Asn Ala Lys Thr Lys Pro
275 280 285

Arg Glu Glu Gln Tyr Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Ala Leu Pro Ala Pro Ile Glu Lys Thr Ile Ser Lys Ala
325 330 335

Lys Gly Gln Pro Arg Glu Pro Gln Val Tyr Thr Leu Pro Pro Ser Arg
340 345 350

Glu Glu Met Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly
435 440

<210> SEQ ID NO 194
<211> LENGTH: 442
<212> TYPE: PRT
<213> ORGANISM: Artificial Sequence
<220> FEATURE:
<223> OTHER INFORMATION: Synthetic: 14E3 (VH + G2.g1.1) or 14E3-IgG2-IgG1.1

<400> SEQUENCE: 194

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Asn Thr Tyr Tyr Asn Pro Ser Leu Lys
50 55 60

Ser Arg Val Thr Ile Ser Val Asp Thr Ser Lys Asn Gln Leu Ser Leu
65 70 75 80

Lys Leu Ser Ser Val Thr Ala Ala Asp Thr Ala Val Tyr Tyr Cys Ala
85 90 95

Arg Phe Gly Ser Asn Asp Ala Phe Asp Ile Trp Gly Gln Gly Thr Met
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Asn
180 185 190

Phe Gly Thr Gln Thr Tyr Thr Cys Asn Val Asp His Lys Pro Ser Asn
195 200 205

Thr Lys Val Asp Lys Thr Val Glu Arg Lys Cys Cys Val Glu Cys Pro
210 215 220

Pro Cys Pro Ala Pro Pro Val Ala Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Lys Phe Asn
260 265 270

Trp Tyr Val Asp Gly Val Glu Val His Asn Ala Lys Thr Lys Pro Arg
275 280 285

Glu Glu Gln Tyr Asn Ser Thr Tyr Arg Val Val Ser Val Leu Thr Val
290 295 300

Leu His Gln Asp Trp Leu Asn Gly Lys Glu Tyr Lys Cys Lys Val Ser
305 310 315 320

Asn Lys Ala Leu Pro Ser Ser Ile Glu Lys Thr Ile Ser Lys Ala Lys
325 330 335

Gly Gln Pro Arg Glu Pro Gln Val Tyr Thr Leu Pro Pro Ser Arg Glu
340 345 350

Glu Met Thr Lys Asn Gln Val Ser Leu Thr Cys Leu Val Lys Gly Phe
355 360 365

Tyr Pro Ser Asp Ile Ala Val Glu Trp Glu Ser Asn Gly Gln Pro Glu
370 375 380

Asn Asn Tyr Lys Thr Thr Pro Pro Val Leu Asp Ser Asp Gly Ser Phe
385 390 395 400

Phe Leu Tyr Ser Lys Leu Thr Val Asp Lys Ser Arg Trp Gln Gln Gly
405 410 415

Asn Val Phe Ser Cys Ser Val Met His Glu Ala Leu His Asn His Tyr
420 425 430

Thr Gln Lys Ser Leu Ser Leu Ser Pro Gly
435 440

<210> SEQ ID NO 195
<211> LENGTH: 443
<212> TYPE: PRT
<213> ORGANISM: Artificial Sequence
<220> FEATURE:
<223> OTHER INFORMATION: Synthetic: 14E3 (VH + G2(C219S).g1) or 14E3-IgG2-C219S-IgG1

<400> SEQUENCE: 195

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Asn Thr Tyr Tyr Asn Pro Ser Leu Lys
50 55 60

Ser Arg Val Thr Ile Ser Val Asp Thr Ser Lys Asn Gln Leu Ser Leu
65 70 75 80

Lys Leu Ser Ser Val Thr Ala Ala Asp Thr Ala Val Tyr Tyr Cys Ala
85 90 95

Arg Phe Gly Ser Asn Asp Ala Phe Asp Ile Trp Gly Gln Gly Thr Met
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys

```
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440


<210> SEQ ID NO 196
<211> LENGTH: 442
<212> TYPE: PRT
<213> ORGANISM: Artificial Sequence
<220> FEATURE:
<223> OTHER INFORMATION: Synthetic: 14E3 (VH + G2(C219S).g1.1) or 14E3-
      IgG2-C219S-IgG1.1

<400> SEQUENCE: 196

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

-continued

```
Gly Glu Ile Asn His Ser Gly Asn Thr Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Arg Phe Gly Ser Asn Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440
```

<210> SEQ ID NO 197
<211> LENGTH: 124
<212> TYPE: PRT

```
<213> ORGANISM: Artificial Sequence
<220> FEATURE:
<223> OTHER INFORMATION: Synthetic: 19H8 (VH)

<400> SEQUENCE: 197

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser
        115                 120


<210> SEQ ID NO 198
<211> LENGTH: 107
<212> TYPE: PRT
<213> ORGANISM: Artificial Sequence
<220> FEATURE:
<223> OTHER INFORMATION: Synthetic: 19H8 (VL1)

<400> SEQUENCE: 198

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Gln
                85                  90                  95

Thr Phe Gly Gln Gly Thr Lys Val Glu Ile Lys
            100                 105


<210> SEQ ID NO 199
<211> LENGTH: 107
<212> TYPE: PRT
<213> ORGANISM: Artificial Sequence
<220> FEATURE:
<223> OTHER INFORMATION: Synthetic: 19H8 (VL2)

<400> SEQUENCE: 199

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105


<210> SEQ ID NO 200
<211> LENGTH: 450
<212> TYPE: PRT
<213> ORGANISM: Artificial Sequence
<220> FEATURE:
<223> OTHER INFORMATION: Synthetic: 19H8 (full length wild-type heavy
      chain)

<400> SEQUENCE: 200

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
```

```
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 201
<211> LENGTH: 214
<212> TYPE: PRT
<213> ORGANISM: Artificial Sequence
<220> FEATURE:
<223> OTHER INFORMATION: Synthetic: 19H8 L1 (full length wild-type light chain 1)

<400> SEQUENCE: 201

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 202
<211> LENGTH: 214
<212> TYPE: PRT
<213> ORGANISM: Artificial Sequence
<220> FEATURE:
<223> OTHER INFORMATION: Synthetic: 19H8 L2 (full length wild-type light
      chain 2)

<400> SEQUENCE: 202

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 203
<211> LENGTH: 453
<212> TYPE: PRT
<213> ORGANISM: Artificial Sequence
<220> FEATURE:
<223> OTHER INFORMATION: Synthetic: 19H8.IgG1 (VH + IgG1)

<400> SEQUENCE: 203

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
```

```
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 204

<211> LENGTH: 453
<212> TYPE: PRT
<213> ORGANISM: Artificial Sequence
<220> FEATURE:
<223> OTHER INFORMATION: Synthetic: 19H8.IgG1.1 (VH + IgG1.1)

<400> SEQUENCE: 204

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 205
<211> LENGTH: 214
<212> TYPE: PRT
<213> ORGANISM: Artificial Sequence
<220> FEATURE:
<223> OTHER INFORMATION: Synthetic: 19H8.IgG1 (VL1 + CL)

<400> SEQUENCE: 205

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 206
<211> LENGTH: 214
<212> TYPE: PRT
<213> ORGANISM: Artificial Sequence
<220> FEATURE:
<223> OTHER INFORMATION: Synthetic: 19H8.IgG1.2 (VL2 + CL)

<400> SEQUENCE: 206

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 207
<211> LENGTH: 5
<212> TYPE: PRT
<213> ORGANISM: Artificial Sequence
<220> FEATURE:
<223> OTHER INFORMATION: Synthetic: 19H8 VH CDR1

<400> SEQUENCE: 207

Asn Tyr Gly Met His
1               5


<210> SEQ ID NO 208
<211> LENGTH: 17
<212> TYPE: PRT
<213> ORGANISM: Artificial Sequence
<220> FEATURE:
<223> OTHER INFORMATION: Synthetic: 19H8 VH CDR2

<400> SEQUENCE: 208

Val Ile Trp Tyr Gly Gly Ser Asn Lys Phe Tyr Ala Asp Ser Val Lys
1               5                   10                  15

Gly


<210> SEQ ID NO 209
<211> LENGTH: 15
<212> TYPE: PRT
<213> ORGANISM: Artificial Sequence
<220> FEATURE:
<223> OTHER INFORMATION: Synthetic: 19H8 VH CDR3

<400> SEQUENCE: 209
```

-continued

Gly Gly Ala Met Val Arg Gly Val Tyr Tyr Tyr Gly Met Asp Val
1 5 10 15

<210> SEQ ID NO 210
<211> LENGTH: 11
<212> TYPE: PRT
<213> ORGANISM: Artificial Sequence
<220> FEATURE:
<223> OTHER INFORMATION: Synthetic: 19H8 VL1 CDR1

<400> SEQUENCE: 210

Arg Ala Ser Gln Gly Ile Ser Ser Ala Leu Ala
1 5 10

<210> SEQ ID NO 211
<211> LENGTH: 7
<212> TYPE: PRT
<213> ORGANISM: Artificial Sequence
<220> FEATURE:
<223> OTHER INFORMATION: Synthetic: 19H8 VL1 CDR2

<400> SEQUENCE: 211

Asp Ala Ser Ser Leu Glu Ser
1 5

<210> SEQ ID NO 212
<211> LENGTH: 9
<212> TYPE: PRT
<213> ORGANISM: Artificial Sequence
<220> FEATURE:
<223> OTHER INFORMATION: Synthetic: 19H8 VL1 CDR3

<400> SEQUENCE: 212

Gln Gln Phe Asn Ser Tyr Pro Gln Thr
1 5

<210> SEQ ID NO 213
<211> LENGTH: 11
<212> TYPE: PRT
<213> ORGANISM: Artificial Sequence
<220> FEATURE:
<223> OTHER INFORMATION: Synthetic: 19H8 VL2 CDR1

<400> SEQUENCE: 213

Arg Ala Ser Gln Ser Val Ser Ser Tyr Leu Ala
1 5 10

<210> SEQ ID NO 214
<211> LENGTH: 7
<212> TYPE: PRT
<213> ORGANISM: Artificial Sequence
<220> FEATURE:
<223> OTHER INFORMATION: Synthetic: 19H8 VL2 CDR2

<400> SEQUENCE: 214

Asp Ala Ser Asn Arg Ala Thr
1 5

<210> SEQ ID NO 215
<211> LENGTH: 9
<212> TYPE: PRT
<213> ORGANISM: Artificial Sequence
<220> FEATURE:
<223> OTHER INFORMATION: Synthetic: 19H8 VL2 CDR3

<400> SEQUENCE: 215

Gln Gln Arg Ser Asn Trp Pro Leu Thr 1 5

<210> SEQ ID NO 216
<211> LENGTH: 449
<212> TYPE: PRT
<213> ORGANISM: Artificial Sequence
<220> FEATURE:
<223> OTHER INFORMATION: Synthetic: 19H8 (VH + G2(C219S)) or 19H8-IgG2-
C219S

<400> SEQUENCE: 216

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Met His Trp Val Arg Gln Ala Pro Gly Lys Gly Leu Glu Trp Met
35 40 45

Ala Val Ile Trp Tyr Gly Gly Ser Asn Lys Phe Tyr Ala Asp Ser Val
50 55 60

Lys Gly Arg Phe Thr Ile Ser Arg Asp Asn Ser Lys Asn Ser Leu Ser
65 70 75 80

Leu Gln Met Asn Ser Leu Arg Ala Glu Asp Thr Ala Val Tyr Tyr Cys
85 90 95

Ala Arg Gly Gly Ala Met Val Arg Gly Val Tyr Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Asn Phe Gly Thr Gln Thr Tyr Thr Cys Asn
195 200 205

Val Asp His Lys Pro Ser Asn Thr Lys Val Asp Lys Thr Val Glu Arg
210 215 220

Lys Ser Cys Val Glu Cys Pro Pro Cys Pro Ala Pro Pro Val Ala Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Phe Arg
290 295 300

Val Val Ser Val Leu Thr Val Val His Gln Asp Trp Leu Asn Gly Lys
305 310 315 320

Glu Tyr Lys Cys Lys Val Ser Asn Lys Gly Leu Pro Ala Pro Ile Glu
325 330 335

Lys Thr Ile Ser Lys Thr Lys Gly Gln Pro Arg Glu Pro Gln Val Tyr
340 345 350

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 217
<211> LENGTH: 450
<212> TYPE: PRT
<213> ORGANISM: Artificial Sequence
<220> FEATURE:
<223> OTHER INFORMATION: Synthetic: 19H8 (VH + G2.g1) or 19H8-IgG2-IgG1

<400> SEQUENCE: 217

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 218
<211> LENGTH: 449
<212> TYPE: PRT
<213> ORGANISM: Artificial Sequence
<220> FEATURE:
<223> OTHER INFORMATION: Synthetic: 19H8 (VH + G2.g1.1) or 19H8-IgG2-
      IgG1.1

<400> SEQUENCE: 218

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 219
<211> LENGTH: 450
<212> TYPE: PRT
<213> ORGANISM: Artificial Sequence
<220> FEATURE:
<223> OTHER INFORMATION: Synthetic: 19H8 (VH + G2(C219S).g1) or 19H8-
      IgG2-C219S-IgG1

<400> SEQUENCE: 219

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60
```

```
Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 220
<211> LENGTH: 449
<212> TYPE: PRT

<213> ORGANISM: Artificial Sequence
<220> FEATURE:
<223> OTHER INFORMATION: Synthetic: 19H8 (VH + G2(C219S).g1.1) or 19H8-IgG2-C219S-IgG1.1

<400> SEQUENCE: 220

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Gly Gly Ser Asn Lys Phe Tyr Ala Asp Ser Val
    50                  55                  60

Lys Gly Arg Phe Thr Ile Ser Arg Asp Asn Ser Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Ala Met Val Arg Gly Val Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 221
<211> LENGTH: 453
<212> TYPE: PRT
<213> ORGANISM: Artificial Sequence
<220> FEATURE:
<223> OTHER INFORMATION: Synthetic: 6G10.IgG1 (VH + IgG1)

<400> SEQUENCE: 221

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
```

```
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 222
<211> LENGTH: 453
<212> TYPE: PRT
<213> ORGANISM: Artificial Sequence
<220> FEATURE:
<223> OTHER INFORMATION: Synthetic: 6G10.IgG1.1 (VH + IgG1.1)

<400> SEQUENCE: 222

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
```

```
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 223
<211> LENGTH: 214
<212> TYPE: PRT
<213> ORGANISM: Artificial Sequence
<220> FEATURE:
<223> OTHER INFORMATION: Synthetic: 6G10.IgG1 (VL + CL)

<400> SEQUENCE: 223

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 224
<211> LENGTH: 449
<212> TYPE: PRT
<213> ORGANISM: Artificial Sequence
<220> FEATURE:
<223> OTHER INFORMATION: Synthetic: 6G10 (VH + G2(C219S)) or 6G10-IgG2-
      C219S

<400> SEQUENCE: 224

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 225
<211> LENGTH: 450
<212> TYPE: PRT
<213> ORGANISM: Artificial Sequence
<220> FEATURE:
<223> OTHER INFORMATION: Synthetic: 6G10 (VH + G2.g1) or 6G10-IgG2-IgG1

<400> SEQUENCE: 225

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
```

```
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 226
<211> LENGTH: 449
<212> TYPE: PRT
<213> ORGANISM: Artificial Sequence
<220> FEATURE:
<223> OTHER INFORMATION: Synthetic: 6G10 (VH + G2.g1.1) or 6G10-IgG2-
      IgG1.1

<400> SEQUENCE: 226

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45
```

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 227

<211> LENGTH: 450
<212> TYPE: PRT
<213> ORGANISM: Artificial Sequence
<220> FEATURE:
<223> OTHER INFORMATION: Synthetic: 6G10 (VH + G2(C219S).g1) or 6G10-
IgG2-C219S-IgG1

<400> SEQUENCE: 227

```
Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
```

```
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 228
<211> LENGTH: 449
<212> TYPE: PRT
<213> ORGANISM: Artificial Sequence
<220> FEATURE:
<223> OTHER INFORMATION: Synthetic: 6G10 (VH + G2(C219S).g1.1) or 6G10-
      IgG2-C219S-IgG1.1

<400> SEQUENCE: 228

Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Thr Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Ser Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

ANTI-GITR ANTIBODIES FOR CANCER DIAGNOSTICS

CROSS-REFERENCE TO RELATED APPLICATIONS

This application is a continuation of U.S. application Ser. No. 15/578,874 (allowed), filed Dec. 1, 2017, which is a 35 U.S.C. 371 national stage filing of International Application No. PCT/US2016/035514, filed Jun. 2, 2016, which claims priority to U.S. Provisional Patent Application Ser. No. 62/170,579, filed Jun. 3, 2015. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on May 8, 2020, is named MXI_544USCN_Sequence_Listing.txt and is 486,026 bytes in size.

BACKGROUND

Glucocorticoid-inducible TNF receptor (GITR) is a T cell costimulatory type I cell surface transmembrane glycoprotein expressed by activated effector T (Teff) cells and at low levels on B cells, eosinophils, basophils, and macrophages (Nocentini et al., *Adv Exp Med Biol* 2009; 647:156-73). GITR is constitutively expressed on regulatory T (Treg) cells. Signaling through GITR potentiates T cell receptor activation of T cells and renders Teff cells resistant to Treg-mediated suppression (Stephens et al., *J Immunol* 2004; 173:5008-20). Determining GITR positivity in tumor tissue may provide an opportunity to target patients that are most likely to benefit from (i.e., be responsive to) anti-GITR immunotherapy, as well as monitoring the status of GITR-positive tumors and efficacy of anti-GITR immunotherapy.

SUMMARY

Provided herein are diagnostic anti-GITR antibodies and methods for detecting GITR protein expression in biological samples, such as tumor tissue samples. Such methods may be useful for, e.g., identifying cancer patients who are likely to respond to anti-GITR immunotherapy and monitoring the status of GITR-positive tumors and efficacy of anti-GITR immunotherapy.

Accordingly, in one aspect, provided herein are methods for detecting human GITR in a biological sample, for example, a human tissue sample (e.g., tumor tissue sample), comprising contacting the sample with an antibody, or antigen-binding fragment thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, and detecting the binding of the antibody to GITR in the sample.

Also provided herein are methods of determining whether a tumor of a cancer patient is GITR-positive comprising:

(a) contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (b) detecting the binding of the antibody to GITR in the sample, and (c) determining the level of GITR protein expression in the sample, wherein a level of GITR protein above a threshold level indicates that the tumor is GITR-positive.

Also provided herein are methods of identifying a cancer patient likely to respond to an anti-GITR immunotherapy comprising:

(a) contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (b) detecting the binding of the antibody to GITR in the tumor sample, (c) determining the level of GITR protein expression in the sample, wherein a level of GITR protein above a threshold level indicates that the tumor is GITR-positive tumor and that the patient is likely to or predicted to respond to anti-GITR immunotherapy.

Also provide herein are methods of treating a cancer patient comprising:

(a) determining whether a tumor of a cancer patient is GITR-positive by (i) contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (ii) detecting the binding of the antibody to GITR in the tumor sample, and (iii) determining the level of GITR protein expression in the sample, wherein a level of GITR protein above a threshold level indicates that the tumor is GITR-positive, and (b) if the tumor is determined to be GITR-positive, administering to the patient an agent that modulates GITR signaling. In certain embodiments, the agent that modulates GITR signaling is an agonistic (i.e., agonist) anti-GITR antibody.

Also provided herein are methods of monitoring a GITR-positive tumor in a cancer patient comprising:

(a) detecting GITR protein expression in the GITR-positive tumor at a first time point by using an antibody comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (b) determining the level of GITR protein expression at the first time point, (c) detecting GITR protein expression in the tumor at a second time point using the same antibody used in step (a), (d) determining the level of GITR protein expression in the tumor from the second time point;

(e) comparing the levels of GITR protein expression determined at the first and second time points, wherein a higher level at the first time point relative to the second time point is indicative of tumor regression, a lower score at the first time point relative to the second time point is indicative of tumor progression, and a relatively unchanged level at the first time point relative to the second time point is indicative of a stable tumor.

Also provided herein are methods of monitoring the efficacy of anti-GITR immunotherapy in a patient having a GITR-positive tumor comprising:

(a) detecting GITR protein expression in the GITR-positive tumor at a first time point before or after initiating anti-GITR immunotherapy by using an antibody comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (b) determining the level of GITR protein expression in the tumor from the first time point, (c) detecting GITR protein expression in the GITR-positive tumor at a second time point after initiating anti-GITR immunotherapy using the same antibody from step (a), (d) determining the level of GITR protein expression in the tumor from the second time point;

(e) comparing the levels of GITR protein expression determined at the first and second time points, wherein a higher level at the first time point relative to the second time point is indicative of effective anti-GITR immunotherapy, a lower score at the first time point relative to the second time point is indicative of ineffective anti-GITR immunotherapy, and an unchanged score at the first time point relative to the second time point is indicative of anti-GITR immunotherapy being stabilizing. In certain embodiments, the anti-GITR immunotherapy comprises administering to the patient a therapeutically effective amount of an anti-GITR antibody, or antigen binding portion thereof.

In certain embodiments, the tumor sample used in the methods described herein is a formalin-fixed paraffin-embedded tumor sample. In certain embodiments, the tumor sample is a frozen tumor tissue sample. In certain embodiments, the methods described herein are performed by immunohistochemistry. In certain embodiments, the level of GITR expression is determined using a scoring system, e.g., the H score system, the Allred score system, the AQUA system, or an automated scoring system.

In certain embodiments, the antibody used in the methods described herein comprises heavy and light chain variable regions comprising the amino acid sequences set forth in SEQ ID NOs: 11 and 12, respectively. In certain embodiments, the antibody used in the methods described herein comprises heavy and light chains comprising the amino acid sequences set forth in SEQ ID NOs: 13 and 14, respectively. In certain embodiments, the heavy chain lacks the C-terminal lysine. In certain embodiments, the antibody is an IgG1, IgG2, IgG3, or IgG4 antibody. In certain embodiments, the antibody binds to soluble human GITR with a $K_D$ of 10 nM or less, as assessed by Biacore.

In certain embodiments, the antibody is a humanized, human, or chimeric antibody. In certain embodiments, the antibody is a chimeric antibody comprising human variable region sequences and non-human constant region sequences, for example, a mouse heavy and light chain constant region. In certain embodiments, the mouse Fc region is a mouse IgG2a Fc region. In certain embodiments, the chimeric antibody comprises heavy and light chain sequences set forth in SEQ ID NOs: 15 and 16, respectively. In certain embodiments, the heavy chain lacks the C-terminal lysine.

In certain embodiments, the antibody used in the methods described herein comprises a detectable moiety, such as a radiolabel, fluorescent label, an enzymatic label, biotin, chromophore, or an ECL label.

Also provided herein are diagnostic kits comprising an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, wherein the antibody or antigen-binding fragment thereof specifically binds to human GITR, and instructions for use. In certain embodiments, the antibody, or antigen-binding portion thereof, comprises the heavy and light chain variable region sequences set forth in SEQ ID NOs: 11 and 12, respectively. In certain embodiments, the antibody comprises the heavy and light chain sequences set forth in SEQ ID NOs: 13 and 14, respectively. In certain embodiments, the antibody comprises the heavy and light chain sequences set forth in SEQ ID NOs: 15 and 16, respectively. In certain embodiments, the heavy chain lacks the C-terminal lysine.

BRIEF DESCRIPTION OF THE FIGURES

FIG. 1 shows the nucleotide sequence (SEQ ID NO: 17) and amino acid sequence (SEQ ID NO: 11) of the heavy chain variable region of the 6G10 human monoclonal antibody. The CDR1 (SEQ ID NO: 5), CDR2 (SEQ ID NO: 6) and CDR3 (SEQ ID NO: 7) regions are delineated and the V, D and J germline derivations are indicated.

FIG. 2 shows the nucleotide sequence (SEQ ID NO: 18) and amino acid sequence (SEQ ID NO: 12) of the kappa light chain variable region of the 6G10 human monoclonal antibody. The CDR1 (SEQ ID NO: 8), CDR2 (SEQ ID NO: 9) and CDR3 (SEQ ID NO: 10) regions are delineated and the V and J germline derivations are indicated.

FIG. 3 shows an alignment of the amino acid sequence of the heavy chain variable regions of 6G10 (SEQ ID NO: 11) with the human germline $V_H$ 3-33, 3-10, and JH6 amino acid sequences.

FIG. 4 shows an alignment of the amino acid sequence of the light chain variable region (VK1) of 6G10 (SEQ ID NO: 12) with the human germline $V_k$ L18 and JK2 amino acid sequences.

FIG. 5 shows the nucleotide sequence (SEQ ID NO: 21) and amino acid sequence (SEQ ID NO: 15) of the heavy chain of the chimeric 6G10 antibody.

FIG. 6 shows the nucleotide sequence (SEQ ID NO: 22) and amino acid sequence (SEQ ID NO: 16) of the light chain of the chimeric 6G10 antibody.

DETAILED DESCRIPTION

Figure 7:
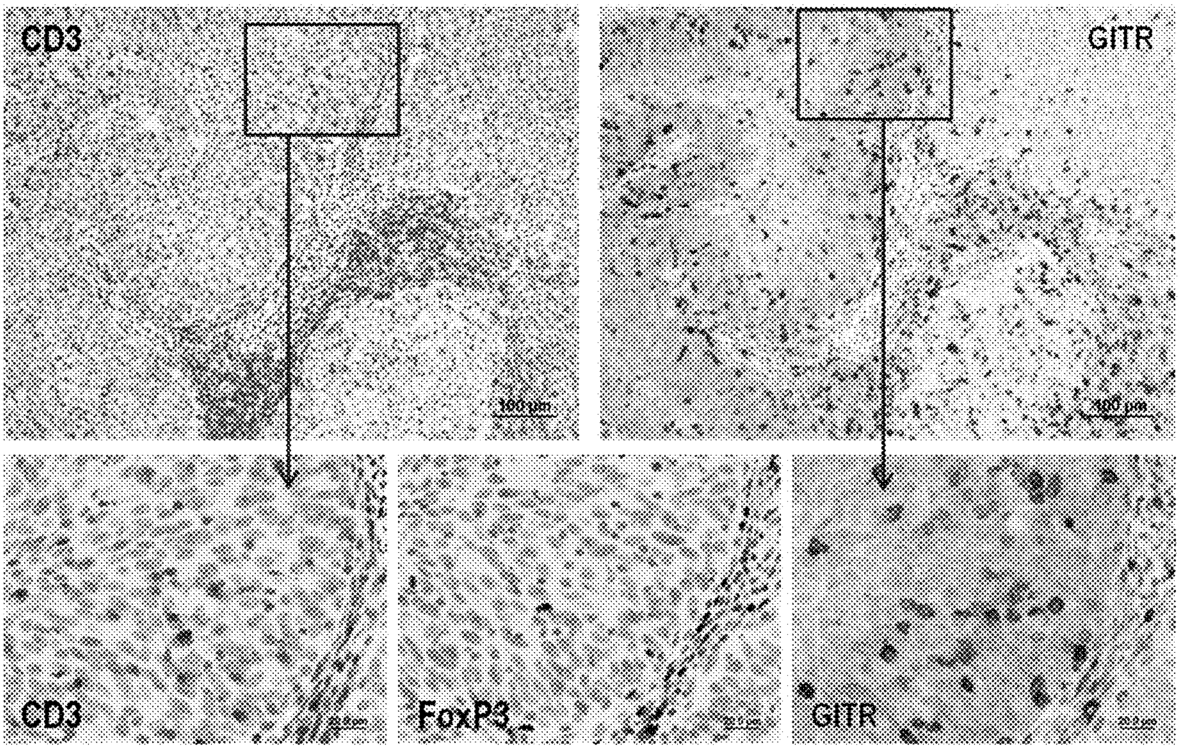
FIG. 7 shows staining of CD3, FoxP3, and GITR on adjacent formalin-fixed paraffin embedded (FFPE) sections from cervical squamous cell carcinoma samples by immunohistochemistry using the chimeric 6G10 antibody.

Disclosed herein are various methods for detecting GITR expression in biological samples, e.g., tumor specimens, using diagnostic anti-GITR antibodies. Such antibodies may be useful for, e.g., monitoring GITR protein levels in a subject; identifying the specific cells that are GITR positive in a specific tissue, such as a tumor tissue (e.g., identifying the presence of GITR in Treg cells and/or tumor cells); the early detection of cancers; monitoring and identification of existing cancers; and assessing the therapeutic efficacy of anti-GITR immunotherapy.

Definitions

In order that the present description may be more readily understood, certain terms are first defined. Additional definitions are set forth throughout the detailed description.

The term "glucocorticoid-inducible TNF receptor" or "GITR" as used herein refers to a receptor that is a member of the TNF-receptor superfamily, which binds to GITR ligand (GITR-L). GITR is also referred to as tumor necrosis factor receptor superfamily, member 18 (TNFRSF18), AITR and CD357. The term "GITR" includes any variants or isoforms of GITR which are naturally expressed by cells. Accordingly, antibodies described herein may cross-react with GITR from species other than human (e.g., cynomolgus GITR). Alternatively, the antibodies may be specific for human GITR and may not exhibit any cross-reactivity with other species. GITR or any variants and isoforms thereof, may either be isolated from cells or tissues which naturally express them or be recombinantly produced using well-known techniques in the art and/or those described herein.

Three isoforms of human GITR have been identified, all of which share the same extracellular domain, except for its C-terminal portion. Variant 1 (Accession No. NP_004186; SEQ ID NO: 1) consists of 241 amino acids and represents the longest transcript. It contains an extra coding segment that leads to a frame shift, compared to variant 2. The resulting protein (isoform 1) contains a distinct and shorter C-terminus, as compared to isoform 2. Variant 2 (Accession No. NP_683699; SEQ ID NO: 2) encodes the longest protein (isoform 2), consisting of 255 amino acids, and is soluble. Variant 3 (Accession No. NP_683700; SEQ ID NO: 3) contains an extra coding segment that leads to a frame shift, compared to variant 2. The resulting protein (isoform 3) contains a distinct and shorter C-terminus, as compared to isoform 2, and consists of 234 amino acids. The amino acid sequences of human GITR isoforms 1, 2, and 3 are set forth in SEQ ID NOs: 1, 2, and 3, respectively, and the extracellular domain of mature GITR has the amino acid sequence set forth in SEQ ID NO: 4.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the anti-GITR antibodies described herein are of the IgG1 or IgG2 subtype. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human GITR). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-GITR antibody described herein, include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg, *Nature Biotech* 2005; 23:1117-25), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species (e.g., human variable regions) and the constant regions are derived from another species (e.g., mouse constant regions), such as an antibody in which the variable regions are derived from a mouse antibody and the constant regions are derived from a human antibody. Constant region sequences for various species are known in the art and could be readily obtained by the skilled artisan to generate chimeric antibodies. An exemplary chimeric anti-GITR antibody comprises human variable region sequences and mouse constant chain sequences. For example, in one embodiment, a chimeric anti-GITR antibody comprises the heavy and light chain sequences set forth in SEQ ID NOs: 15 and 16, respectively. In certain embodiments, the heavy chain of the chimeric antibody lacks the C-terminal lysine.

An "isolated antibody," as used herein, is intended to refer to an antibody which is substantially free of other antibodies having different antigenic specificities (e.g., an isolated antibody that specifically binds to GITR is substantially free of antibodies that specifically bind antigens other than GITR). An isolated antibody that specifically binds to an epitope of GITR may, however, have cross-reactivity to other GITR proteins from different species.

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 instrument using the predetermined antigen, e.g., recombinant human GITR, as the analyte and the antibody as the ligand.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. A "protein" may comprise one or more polypeptides.

"Immunotherapy" refers to the treatment of a subject afflicted with, or at risk of contracting or suffering a recurrence of, a disease by a method comprising inducing, enhancing, suppressing or otherwise modifying an immune response. In this context, "anti-GITR immunotherapy" refers to the treatment of a subject afflicted with, or at risk of contracting or suffering a recurrence of, a disease (e.g., cancer) by a method comprising inducing, enhancing, suppressing or otherwise modifying an immune response by administering an agent (e.g., an agonistic anti-GITR antibody) that modulates GITR signaling and results in, e.g., the induction and/or enhancement of T cell activation (e.g., increase in IL-2 and/or IFN-γ production by T cells and/or increase in proliferation of T cells), depletion of regulatory T cells, etc.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "cancer" refers to a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

As used herein, a "tumor" refers to an abnormal mass of tissue resulting from excessive cell division that is uncontrolled and progressive. Tumors can be benign or malignant.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc. Various aspects described herein are described in further detail in the following subsections.

As used herein, the singular forms "a," "an," and "the" include plural referents unless the context clearly dictates otherwise. The use of "or" or "and" means "and/or" unless stated otherwise. Furthermore, use of the term "including" as well as other forms, such as "include," "includes," and "included," is not limiting.

The term "about" as used herein when referring to a measurable value such as an amount, temporal duration, and the like, encompasses variations of up to ±10% from the specified value. Unless otherwise indicated, all numbers expressing quantities of ingredients, properties such as molecular weight, reaction conditions, scores in an art-recognized scoring system, etc., used herein are understood as being modified by the term "about."

The term "sample of a subject" refers to cells (e.g., tumor cells, T cells, B cells or other), tissues (e.g., tumor), fluids and/or combination thereof isolated from a subject.

The term "control sample" or "reference sample" as used herein refers to any clinically relevant control or reference sample, including, e.g., a sample from a healthy subject or a sample made at an earlier time from the subject being assessed. For example, a control sample or reference sample can be a sample taken from a subject prior to onset of cancer, an earlier stage of disease, or before administration of treatment.

As used herein, "threshold level" or "cut-off level" in the context of expression levels refers to a level of GITR protein expression above which a patient sample (e.g., a patient tumor sample) is deemed "GITR-positive" and below which the sample is deemed "GITR-negative." The threshold level may be based on, e.g., one or more compilations of data from "normal" patient samples (e.g., a patient population who do not have GITR-positive tumors) or matching normal tissue from the patient being assessed. The threshold level may be placed in the framework of an art-recognized scoring system (e.g., the H score system). For example, in one embodiment, the tumor of a patient having an H score of 1 in matching normal tissue would be considered GITR-positive if the H score of the tumor is greater than 1. A threshold detection level may be the lowest detection level using a given detection method. For example, a threshold level may be the level below which GITR cannot be detected using immunohistochemistry, e.g., using an immunohistochemistry method described herein.

Diagnostic Anti-GITR Antibodies

Provided herein are diagnostic anti-GITR antibodies that are useful for detecting GITR protein expression in human tissue, e.g., tumor tissue. Such antibodies are useful, e.g., for identifying/selecting subjects who are likely to benefit from (i.e., be responsive to) treatment with anti-GITR immunotherapy, monitoring the progression of a GITR-positive tumor, and/or monitoring the efficacy of anti-GITR immunotherapy.

Accordingly, in certain embodiments, a diagnostic anti-GITR antibody useful for detecting GITR protein expression in tissue samples, e.g., human tumor tissue samples, comprises the heavy and light chain variable region CDR sequences, heavy and light chain variable region sequences, or full length heavy and light chain sequences of antibody 6G10 (a fully human anti-GITR antibody). A summary of the relevant sequences for 6G10 is provided in Table 2.

In some embodiments, the anti-GITR antibody has the heavy chain variable region CDR1, CDR2, and CDR3 sequences set forth in SEQ ID NOs: 5-7, and the light chain variable region CDR1, CDR2, and CDR3 sequences set forth in SEQ ID NOs: 8-10, and specifically binds to human GITR.

In some embodiments, the anti-GITR antibody has the heavy chain variable region sequence set forth in SEQ ID NO: 11, and the light chain variable region sequence set forth in SEQ ID NO: 12.

In some embodiments, the anti-GITR antibody has heavy chain and light chain sequences set forth in SEQ ID NOs: 13 and 14, respectively. In certain embodiments, the heavy chain lacks the C-terminal lysine.

In some embodiments, the anti-GITR antibody is an IgG1, IgG2, IgG3, or IgG4 antibody, or a variant thereof. In other embodiments, the antibody is an IgA, IgD, IgE, or IgM antibody.

In some embodiments, the anti-GITR antibody is a human antibody, a humanized antibody, or a chimeric antibody.

In some embodiments, the anti-GITR antibody binds to soluble GITR with a $K_D$ of 10 nM or less as determined by Biacore.

In certain embodiments, the anti-GITR antibody is a chimeric antibody. In one embodiment, the anti-GITR antibody has the heavy and light chain variable region sequences of the 6G10 antibody (SEQ ID NOs: 11 and 12, respectively), and the constant regions of a non-human species, e.g., a mouse IgG2a constant region (SEQ ID NO: 25). Such chimeric 6G10 antibodies are useful for, e.g., reducing background staining in immunohistochemistry when detecting GITR protein expression in human tissue. Accordingly, in one embodiment, the diagnostic anti-GITR antibody is a chimeric antibody comprising the heavy and light chain sequences set forth in SEQ ID NOs: 15 and 16, respectively. In certain embodiments, the heavy chain of the chimeric antibody lacks the C-terminal lysine.

In certain embodiments, the diagnostic anti-GITR antibodies described herein comprise a detectable moiety to facilitate detection of GITR expression in, for example, tumor samples by, e.g., immunohistochemistry, as described infra. Exemplary detection moieties include luminescent labels, fluorescent labels, radiolabels (e.g., $^{99}$Tc, $^{45}$Ti, $^{112}$In, $^{111}$In, $^{3}$H, $^{121}$I, $^{125}$I, $^{131}$I, $^{14}$C, $^{18}$F, $^{36}$Cl, $^{55}$Co, $^{51}$Cr, $^{67}$Cu, $^{66}$Ga, $^{68}$Ga, $^{76}$Br, $^{89}$Zr, $^{35}$S, $^{32}$P, $^{90}$Y, $^{13}$N, $^{15}$O, $^{211}$At, $^{186}$Re, $^{188}$Re, $^{75}$Se), and enzymatic labels (e.g., horseradish peroxidase, alkaline phosphatase, glucose oxidase, urease, acetylcholinetransferase, luciferase, and beta-galactosidase), epitope tags, chromophore labels, phosphorescent labels, photoaffinity molecules, ECL labels, dyes, biotin, haptens, and the like. Such labels are well known in the art and can be attached to the anti-GITR antibodies using art-recognized methods. Preferably, attachment of the detectable label does not significantly interfere with binding of the antibody to GITR. The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, methods of conjugating the labels result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter et al., *Curr Opin Chem Biol* 2009; 13 235-44; WO 2009/059278; WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger et al., *Angew Chem Int Ed Engl* 2008; 47:10030-74). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul et al., *Org Biomol Chem* 2009; 7:3361-71.

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese et al. *ChemBioChem* 2009; 10:425-7). It is also possible to obtain a desired amino acid modification by utilizing the specific enzymatic reactivity of certain enzymes with a natural amino acid in a given sequence context (see, e.g., Taki et al., *Prot Eng Des Sel* 2004; 17:119-26; Gautier et al. *Chem Biol* 2008; 15:128-36; Bordusa et al., *Bioorganic Chemistry* (2004) 389-403).

Site specific reaction and covalent coupling can also be achieved by the selective reaction of terminal amino acids with appropriate modifying reagents.

The reactivity of an N-terminal cysteine with benzonitrils (see Ren et al., *Angew Chem Int Ed Engl* 2009; 48:9658-62) can be used to achieve a site-specific covalent coupling.

Native chemical ligation can also rely on C-terminal cysteine residues (Taylor et al., *Nucleic Acids and Molecular Biology* 2009; 22:65-96). EP 1 074 563 describes a conjugation method which is based on the faster reaction of a cysteine within a stretch of negatively charged amino acids with a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see, e.g., de Graaf et al., *Bioconjug Chem* 2009; 20:1281-95). Since a great variety of orthogonal functional groups is at stake and can be introduced into a synthetic peptide, conjugation of such peptide to a linker is standard chemistry.

In some embodiments, the detectable label is indirectly conjugated to the antibody. For example, the antibody can be conjugated to biotin, and the label can be conjugated to avidin using methods well known in the art. In another embodiment, an unlabeled antibody is detected using a labeled antibody which binds to the unlabeled antibody. In certain embodiments, the labeled antibody that is used for detection is labeled with any of the labels set forth above. In certain embodiments, the labeling and detection is conducted as described in the Examples, e.g., using the Leica Bond Polymer Refine Detection System (Leica, Buffalo Grove, Ill., Catalog DS9800).

Methods of Production

The diagnostic anti-GITR antibodies described herein can be produced using art-recognized techniques. In certain embodiments, the antibody can be purified from a hybridoma producing the antibody (e.g., the 6G10 antibody). For example, a hybridoma producing the antibody can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using the 1.43 extinction coefficient.

In certain embodiments, the antibodies described herein can be produced recombinantly. For example, DNAs encoding partial or full-length light and heavy chains described herein can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (*Gene Expression Technology. Methods in Enzymology* 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., *MCB* 1988; 8:466-72).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss et al., *Immunology Today* 1985; 6:12-13).

Preferred mammalian host cells for expressing the recombinant antibodies described herein include Chinese Hamster Ovary (CHO cells) (including dhfr− CHO cells, described in Urlaub and Chasin, *PNAS* 19809; 77:4216-220, used with a DHFR selectable marker, e.g., as described in Kaufman et al., *Mol Biol* 1982; 159:601-21, NSO myeloma cells, COS cells, and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The chimeric anti-GITR antibodies described herein can be prepared based on the sequence of a human monoclonal antibody prepared as described above. For instance, in one embodiment, DNA encoding the human heavy and light variable regions of the 6G10 antibody can be operatively linked to a non-human constant region (e.g., a murine constant region) using routine recombinant technology.

Methods of Detection of Human GITR on Cells

Provided herein are methods for detecting GITR protein expression in a biological sample, e.g., a human tumor tissue sample, by contacting the sample with an anti-GITR antibody, e.g., described herein, such as an anti-GITR antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, respectively, wherein the antibody or antigen-binding fragment thereof specifically binds to human GITR, and detecting the binding of the antibody to GITR in the sample, e.g., by immunohistochemistry. In certain embodiments, the heavy chain lacks the C-terminal lysine. In some embodiments, the anti-GITR antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine.

In certain embodiments, exemplary biological samples include blood samples, serum samples, cells, surgically-resected tissue, and biopsied tissue (e.g. cancer tissue) obtained from the cancer patient. Biological samples for use in the methods described herein can be fresh, frozen, or fixed. Biological samples, e.g., tumor samples, can be obtained from the patient using routine methods, such as, but not limited to, biopsy, surgical resection, or aspiration.

The methods used to detect GITR expression in human tissue, e.g., tumor tissue, can be qualitative, semi-quantitative, or quantitative. Art-recognized antibody-based methods for detecting GITR protein levels in biological samples include, but are not limited to, enzyme-linked immunosorbent assay (ELISA), radioimmunoassays, electrochemiluninescence (ECL) assays, surface plasmon resonance, western blot, immunoprecipitation, fluorescence-activated cell sorting (FACS), immunofluorescence, immunohistochemistry, and the like. Methods for detecting GITR expression in a biological sample may include control samples (negative and positive controls). For example, a negative control sample may be a sample containing no GITR protein, and a positive controls sample is a sample containing GITR protein. Comparing the results with the negative and positive controls can confirm the presence or absence of GITR in the biological sample.

In one embodiment, GITR expression in a tumor tissue sample is assessed by immunohistochemistry. This technique allows detection of GITR on specific cell types, e.g., Treg cells, e.g., Treg cells within a tumor, and tumor cells.

General immunohistochemical methods are well-known in the art. Specific conditions, considerations, and guidance for performing immunohistochemistry are described in, e.g., Immunohistochemical Staining Methods 6th Edition 2013, Taylor C R, Rudbeck L, eds., Dako North America, available as an Education Guide at www.dako.com; "Immunohistochemical Staining Method guide"). Immunohistochemical staining may be conducted on fixed tissue sections or on frozen tissue sections. When using fixed tissue sections, e.g., formalin fixed paraffin embedded (FFPE) tissue sections, the procedure generally involves the following steps: obtaining a tumor tissue sample (e.g., by biopsy), fixation of the tumor sample; embedding (e.g., in paraffin); sectioning and mounting; antigen retrieval; incubation with a primary antibody (e.g., chimeric 6G10 antibody described herein), detection (e.g., after amplification of the antigen/antibody complex signal), and interpretation by a pathologist (e.g., using an art-recognized scoring system).

Suitable, non-limiting fixatives include, for example, paraformaldehyde, glutaraldehyde, formaldehyde, acetic acid, acetone, osmium tetroxide, chromic acid, mercuric chloride, picric acid, alcohols (e.g., methanol, ethanol), Gendre's fluid, Rossman's fluid, B5 fixative, Bouin's fluid, Carnoy's fixative, and methacarn. In a preferred embodiment, the tumor sample is fixed in formaldehyde (e.g., 10% buffered formalin, which corresponds to 4% formaldehyde in a buffered solution). Once fixed, the tumor sample is serially dehydrated using alcohol or xylene, embedded in paraffin, and cut with a microtome to generate tumor tissue sections (e.g., with a thickness of about 4-5 μm), which can then be mounted onto microscope slides (e.g., adhesive-coated glass slides).

Exemplary embedding materials include paraffin, celloidin, OCT™ compound, agar, plastics, or acrylics. In a preferred embodiment, the embedding agent is paraffin.

Antigen retrieval can be performed using any method known in the art. Antigen retrieval treatment can involve heat (e.g., heat-induced epitope retrieval (HIER), as described in Example 3), or enzymatic degradation (proteolytic-induced epitope retrieval (PIER)). Exemplary antigen retrieval methods include microwave heating, proteolytic treatment (e.g., with proteinase K), pressure cooker heating, and water bath heating. Detailed general methods for antigen retrieval are described in Chapter 3 of the Immunohistochemical Staining Method guide. In certain embodiments, the antigen retrieval is performed by HIER in combination with commercially available antigen retrieval buffers (as described in Example 3).

The methods described herein employ anti-GITR antibodies to detect the expression levels of human GITR protein. In certain embodiments, the diagnostic anti-GITR antibody comprises the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, respectively, wherein the antibody or antigen-binding fragment thereof specifically binds to human GITR, as described supra. In certain embodiments, the heavy chain lacks the C-terminal lysine. In some embodiments, the anti-GITR antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine. Such antibodies are particularly useful for detecting GITR expression in tumor tissue sections (see, e.g., Example 3).

GITR protein expression in tissue, e.g., tumor, samples can be detected using direct or indirect methods. For example, the primary antibody may comprise a detectable moiety, such as the enzyme horseradish peroxidase (HRP) or a fluorescent label (e.g., FITC, TRITC), as described herein. In certain embodiments, the primary antibody does not itself comprise a detectable moiety, but is detected by binding of a secondary antibody to it, for indirect immunohistochemistry. Accordingly, in certain embodiments, the secondary antibody comprises a detectable label, e.g., an enzymatic, chromogenic, or fluorescent label. In certain embodiments, the primary antibody is a chimeric antibody comprising human variable region sequences and a non-human Fc region. A secondary antibody can be used to recognize the non-human Fc region of the primary antibody in order to reduce background staining.

In some embodiments, GITR protein expression can be detected using the avidin-biotin complex method (ABC method). In these embodiments, the secondary antibody is biotinylated and can serve as a bridge between the primary antibody and biotin-avidin-peroxidase complex. Other suitable non-limiting methods for immunohistochemistry include those described in Chapter 6 of the Immunohistochemical Staining Method guide, e.g., methods described in Chilosi et al., *Biotech Histochem* 1994; 69:235; Sabattini et al., *J Clin Pathol* 1998; 51:506-11; and Gross et al., JBC 1959; 234:1622.

General methods for preparing and staining frozen tissue sections are well known in the art, and are described in, e.g., the Immunohistochemical Staining Method guide, Chapter 3 of Immunohistochemistry and Methods (Buchwalow and Bocker, Springer-Verlag Berlin Heidelberg 2010), and Chapter 21 of *Theory and Practice of Histological Techniques* (Bancroft and Gamble, $6^{th}$ Edition, Elsevier Ltd., 2008). Frozen tissue section staining can be performed as described in Example 3.

GITR protein can be detected as described in the Examples.

In some embodiments, slides stained with the anti-GITR antibodies described herein can be further counterstained with, e.g., hematoxylin and/or eosin, using methods well known in the art.

In the interpretation step, GITR protein expression detected by immunohistochemistry can be scored using art-recognized scoring methods. Non-limiting examples of scoring methods are described below.

For example, in certain embodiments, GITR expression is evaluated using the H-score (histochemical score) system, which is widely used in the art and is useful given its dynamic range and use of weighted percentiles. The H-score is a semiquantitative scoring system based on the formula: 3×percentage of strongly staining cells (3+ staining)+2× percentage of moderately staining (2+ staining) cells+1× percentage of weakly staining (1+ staining) cells+0×percentage of non-stained (0 staining) cells, giving a score range of 0 to 300. See, e.g., McCarty et al., *Cancer Res* 1986; 46:4244-8; Bosman et al., *J Clin Pathol* 1992; 45:120-4; Dieset et al., *Analyt Quant Cytol Histol* 1996; 18:351-4. Control tissue can include, e.g., matching non-tumor tissue from the same subject. Accordingly, in certain embodiments, the number of cells staining positive for GITR using the anti-GITR antibodies herein, and the intensity of staining, can be used to determine an H-score.

In other embodiments, GITR expression is evaluated using the Allred scoring system (Allred et al., *Mod Pathol* 1998; 11:155-68; Harvey et al., *J Clin Oncol* 1999; 17:1474-91). This scoring system involves adding proportion and intensity scores to obtain a total score. Accordingly, in some embodiments, the proportion score is obtained based on the estimated proportion of tumor cells that are positive for GITR (0: none, 1: <1/100, 2: 1/100 to 1/10, 3: 1/10 to 1/3; 4: 1/3 to 2/3; and 5: >2/3), and the intensity score is obtained based on the average intensity of GITR expression in positive tumor cells (0: none, 1: weak, 2: intermediate, 3: strong). Thus, Allred scores range from 0 to 8, with a score ranging from 3 to 8 considered positive (i.e., positive detection). Accordingly, in certain embodiments, tumors with an Allred score of 3 to 8, for example, an Allred score of 3, 4, 5, 6, 7, or 8, for GITR staining are considered GITR-positive tumors.

In other embodiments, the scoring system is automated, e.g., computerized, and quantified by image analysis. Automated methods are well known in the art. For example, an average threshold measure (ATM) score, which obtains an average of 255 staining intensity levels, can be calculated as described in, e.g., Choudhury et al., *J Histochem Cytochem* 2010; 58:95-107, Rizzardi et al., *Diagnostic Pathology* 2012; 7:42-52. Another automated scoring system is AQUA® (automated quantitative analysis), which is performed using, e.g., tissue microarrays (TMAs), on a continuous scale. AQUA® is a hybrid of standard immunohistochemistry and flow cytometry that provides an objective numeric score ranging from 1-255, and involves antigen retrieval, use of primary and secondary antibodies, and multiplexed fluorescent detection. Optimal cutoff points can be determined as described in Camp et al. *Clin Cancer Res* 2004; 10:7252-9. The AQUA® scoring system is described in detail in Camp et al., *Nat Med* 2002; 8:1323-7; Camp et al., *Cancer Res* 2003; 63:1445-8; Ghosh et al., *Hum Pathol* 2008; 39:1835-43; Bose et al., *BMC Cancer* 2012; 12:332; Mascaux et al., *Clin Cancer Res* 2011; 17:7796-807. Other suitable automated immunohistochemistry platforms include commercially available platforms, such as the Leica BOND RX staining platform. The platform detects GITR expression in tumor tissue on the basis of staining intensity on the following scale: minimal, <1 cells per 20× objective field; mild, 1~<10 cells per 20× objective field; moderate, 10~<50 cells per 20× objective field, marked, 50~<200 cells per 20× objective; and intense, >200 cells per 20× objective field.

Accordingly, provided herein are methods for determining whether a tumor of a cancer patient is GITR-positive and/or comprises GITR positive cells, comprising contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR.

Also provided herein are methods for determining whether a tumor of a cancer patient is GITR-positive and/or comprises GITR positive cells, comprising:

(a) contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, and (b) detecting the binding of the antibody to GITR in the sample.

Also provided herein are methods for determining whether a tumor of a cancer patient is GITR-positive and/or comprises GITR positive cells comprising:

(a) contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, (b) detecting the binding of the antibody to GITR in the sample, and (c) determining the level of GITR protein expression in the sample, wherein a level of GITR protein above a threshold level, e.g., level of detection using a given detection method, indicates that the tumor is GITR-positive tumor.

Also provided herein are methods for identifying GITR positive cells in a tissue (e.g., tumor) sample comprising:

(a) contacting a tissue (e.g., tumor) sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on specific or individual cells of the tissue (e.g., tumor) sample; and optionally (c) staining the tissue (e.g., tumor) sample, e.g., with markers of given cell types (e.g., CD3, CD4, CD8, CD25, or FoxP3 markers) and/or with hematoxylin and eosin, to identify the cells that were identified as GITR positive in step (b).

Step (c) allows identification of GITR positive cells as being, e.g., T cells, such as Treg cells, or tumor cells. Thus, provided herein are the following methods:

A method for detecting the presence of, and/or identifying the number of, T cells expressing GITR in a tissue (e.g., tumor) sample, and/or level of GITR on T cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on T cells of the tissue (e.g., tumor) sample; and optionally (c) staining the tissue (e.g., tumor) sample, e.g., with markers of T cells (e.g., CD3, CD4, CD8, CD25, or FoxP3 markers) and/or with hematoxylin and eosin, to identify the T cells that were identified as GITR positive in step (b).

A method for detecting the presence of, and/or identifying the number of, Treg cells expressing GITR in a tissue (e.g., tumor) sample, and/or the level of GITR on Treg cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on Treg cells of the tissue (e.g., tumor) sample; and optionally (c) staining the tissue (e.g., tumor) sample, e.g., with markers of Treg cells (e.g., a FoxP3 marker) and/or with hematoxylin and eosin, to identify the Treg cells that were identified as GITR positive in step (b).

A method for detecting the presence of, and/or identifying the number of, Teff cells expressing GITR in a tissue (e.g., tumor) sample, and/or the level of GITR on Teff cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on Teff cells of the tissue (e.g., tumor) sample; and optionally (c) staining the tissue (e.g., tumor) sample, e.g., with markers of Teff cells (e.g., a FoxP3 marker) and/or with hematoxylin and eosin, to identify the Teff cells that were identified as GITR positive in step (b).

A method for detecting the presence of, and/or identifying the number of Treg and Teff cells expressing GITR in a tissue (e.g., tumor) sample, and/or the level of GITR on Treg and Teff cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on Treg and Teff cells of the tissue (e.g., tumor) sample; and optionally (c) staining the tissue (e.g., tumor) sample, e.g., with markers of Treg and Teff cells (e.g., CD3, CD4, CD8, CD25, and/or FoxP3 markers) and/or with hematoxylin and eosin, to identify the Treg and Teff cells that were identified as GITR positive in step (b).

A method for detecting the presence of, or identifying the number of, tumor cells expressing GITR in a tumor sample, and/or level of GITR on tumor cells of a tumor sample comprising:

(a) contacting a tumor sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on tumor cells of the tumor sample; and optionally (c) staining the tumor sample, e.g., with markers of tumor cells or other cell type and/or with hematoxylin and eosin, to identify the tumor cells that were identified as GITR positive in step (b).

A method for detecting the presence of, and/or identifying the number of, tumor cells and Treg cells expressing GITR in a tissue (e.g., tumor) sample, and/or the level of GITR on tumor cells and Treg cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on tumor cells and Treg cells of the tissue (e.g., tumor) sample; and optionally (c) staining the tissue (e.g., tumor) sample, e.g., with markers of tumor and/or Treg cells (e.g., a FoxP3 marker) and/or with hematoxylin and eosin, to identify the tumor and Treg cells that were identified as GITR positive in step (b).

A method for detecting the presence of, and/or identifying the number of, tumor cells, Treg cells and Teff cells expressing GITR in a tissue (e.g., tumor) sample, and/or the level of GITR on tumor cells, Treg cells and Teff cells of a tissue (e.g., tumor) sample comprising:

(a) contacting a tissue (e.g., tumor) sample, e.g., from a subject, with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR; and (b) detecting the binding of the antibody to GITR on tumor cells, Treg cells and Teff cells of the tissue (e.g., tumor) sample; and optionally (c) staining the tissue (e.g., tumor) sample, e.g., with markers of tumor cells, Treg cells and/or Teff cells (e.g., CD3, CD4, CD8, CD25, and/or FoxP3 markers) and/or with hematoxylin and eosin, to identify the tumor cells, Treg cells and Teff cells that were identified as GITR positive in step (b).

Exemplary tumor markers include, for example, ErbB receptors, Melan A [MART1], gp100, tyrosinase, TRP-1/gp 75, TRP-2, MAGE-1, MAGE-3, HPV E6 and E7 proteins, Mucin [MUC-1], prostate-specific antigen [PSA], carcinoembryonic antigen [CEA] PIA tumor antigen, MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2.

T reg cell surface markers include CD4, CD25 and FOXP3.

In certain embodiments, a combination of detection methods is used to increase the accuracy of designating a tumor as being GITR-positive or GITR-negative. For example, in one embodiment, a combination of immunohistochemistry and fluorescence in situ hybridization (FISH) is used to type a tumor as being GITR positive or negative. Such approaches have been used to, e.g., optimize Her-2/neu testing. See, e.g., Ridolfi et al., *Mod Pathol* 2000; 13:866-73. Any of the antibody-based methods of detection described herein can be used in the combination, or in combination with RNA-based detection methods, such as RNAscope and quantitative PCR.

The methods of detection described above are typically performed in conjunction with a reference or control sample. In some embodiments, the control sample is a section of matched normal tissue. In some embodiments, the control or reference sample is derived from a subject that is not afflicted with a GITR-expressing tumor or cancer (e.g., a healthy subject). Such samples may provide a standardized reference for the amount of GITR-expressing cells in a biological sample.

Exemplary Prognostic Methods

Provided herein are methods for identifying a cancer patient that is likely to respond to an anti-GITR immunotherapy or predicting whether a cancer patient will respond to anti-GITR immunotherapy comprising:

(a) contacting a tumor sample from the patient with an anti-GITR antibody, or antigen-binding portion thereof, (b) detecting the binding of the antibody to GITR in the tumor sample, (c) determining the level of GITR protein expression in the sample, wherein a level of GITR protein above a threshold level indicates that the tumor is a GITR-positive tumor and that the patient is likely to or predicted to respond to anti-GITR immunotherapy. In certain embodiments, the level of expression of GITR on specific immune cells, e.g., tumor infiltration lymphocytes (TILs), such as T cells, e.g., Treg cells, e.g., in a tumor, is detected or monitored, and, e.g., determines likelihood of response of a subject to an anti-GITR therapy. In certain embodiments, the levels of expression of GITR on tumor cells is detected or monitored, and, e.g., determines likelihood of response of a subject to an anti-GITR therapy.

In certain embodiments, the anti-GITR antibody is an antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, wherein the antibody or antigen-binding fragment thereof specifically binds to human GITR. In certain embodiments, the heavy chain lacks the C-terminal lysine. In some embodiments, the anti-GITR antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine. In certain embodiments, the detection of GITR expression is performed by immunohistochemistry, as described supra. In one embodiment, immunohistochemistry is combined with another detection method, e.g., FISH.

In certain embodiments, the tumor sample is prepared as FFPE sections. In other embodiments, the tumor sample is prepared as frozen tissue sections.

In some embodiments, a tumor is considered GITR-positive and likely to benefit from anti-GITR immunotherapy if a sample of the tumor or immune cells therein, e.g., tumor infiltration lymphocytes (TILs), e.g., Treg cells, has more GITR-positive cells than a matching normal tissue, or immune cell, e.g., T reg cell, from the same cancer patient.

In certain embodiments, the cancer patient is likely to or predicted to benefit from anti-GITR immunotherapy if the number of GITR-positive cells, e.g., immune cells, e.g., tumor infiltration lymphocytes (TILs), such as T reg cells, and/or tumor cells, in the tumor sample exceeds a threshold level. A threshold level may be the lowest level of GITR as determined with a given detection system, e.g., immunohistochemistry, as further described herein, such as in the Examples. In certain embodiments, the cancer patient is likely to or predicted to benefit from anti-GITR immunotherapy if the number of GITR-positive cells, e.g., immune cells, e.g., tumor infiltration lymphocytes (TILs), such as T reg cells, and/or tumor cells, in the tumor sample exceeds a threshold number or proportion using an art-recognized scoring system described supra. Thus, in some embodiments, the number or proportion of GITR-positive cells exceeds a certain threshold number or proportion using a scoring system described herein and is defined as being "GITR-positive."

In certain embodiments, a tumor sample having at least 1%, for example, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, or at least 95% of cells in the tumor, e.g., tumor cells and/or immune cells, e.g., tumor infiltration lymphocytes (TILs), such as T reg cells, expressing GITR protein is designated as being "GITR-positive" and indicates that the cancer patient is likely to or predicted to respond to anti-GITR immunotherapy.

In some embodiments, an H score is calculated for the tumor sample. Accordingly, in certain embodiments, a tumor sample with an H score of at least 5, such as at least 10, at least 15, at least 20, at least 25, at least 30, at least 40, at least 50, at least 60, at least 70, at least 80, at least 90, at least 100, at least 125, at least 150, at least 175, at least 200, at least 225, at least 250, at least 275, or at least 290 is designated as being "GITR-positive" and indicates that the cancer patient is likely to or predicted to respond to anti-GITR immunotherapy. The score may be calculated based on all cells in a tumor, or a specific type of cells, e.g., immune cells, e.g., tumor infiltration lymphocytes (TILs), such as Treg cells, and/or tumor cells.

In some embodiments, an Allred score is calculated for the tumor sample. Accordingly, in certain embodiments, a tumor sample with an Allred score of at least 3, such as at least 4, at least 5, at least 6, at least 7, or 8 is designated as being "GITR-positive" and indicates that the cancer patient is likely to or predicted to respond to anti-GITR immunotherapy. The score may be calculated based on all cells in a tumor, or a specific type of cells, e.g., immune cells, e.g., tumor infiltration lymphocytes (TILs), such as Treg cells, and/or tumor cells.

In some embodiments, an AQUA score is calculated. Accordingly, in certain embodiments, a tumor sample with an AQUA score of at least 5, such as at least 10, at least 15, at least 20, at least 25, at least 30, at least 40, at least 50, at least 60, at least 70, at least 80, at least 90, at least 100, at least 125, at least 150, at least 175, at least 200, at least 225, or at least 250 is designated as being "GITR-positive" and indicates that the cancer patient is likely to or predicted to respond to anti-GITR immunotherapy. The score may be calculated based on all cells in a tumor, or a specific type of cells, e.g., immune cells, e.g., tumor infiltration lymphocytes (TILs), such as Treg cells, and/or tumor cells.

In certain embodiments, a combination of one of the scoring systems above with another detection modality, such as FISH, is used to increase the accuracy of determining whether a tumor is GITR-positive or GITR-negative.

In certain embodiments, the patient has a cancer selected from the group consisting of squamous cell carcinoma, small-cell lung cancer, non-small cell lung cancer, squamous non-small cell lung cancer (NSCLC), non squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. In certain embodiments, the cancer is a metastatic cancer, refractory cancer, or recurrent cancer.

Once a cancer patient has been identified as being likely to benefit from anti-GITR immunotherapy (i.e., has a GITR-positive tumor), the patient can be treated with a therapeutic anti-GITR antibody (i.e., anti-GITR immunotherapy).

Accordingly, provided herein are method of treating a cancer patient with a GITR-positive tumor, as determined by the level of GITR protein expression using the anti-GITR antibodies and methods provided herein, comprising administering to the patient a therapeutically-effective amount of an anti-GITR antibody, or antigen-binding portion thereof.

In certain embodiments, the anti-GITR antibody used to determine the level of GITR protein expression is an antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, respectively, wherein the antibody or antigen-binding fragment thereof specifically binds to human GITR. In certain embodiments, the heavy chain lacks the C-terminal lysine. In some embodiments, the antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine. In certain embodiments, the detection of GITR expression is performed by immunohistochemistry, as described supra.

In certain embodiments, a cancer patient determined as having a GITR-positive tumor (ie., GITR-positive tumor cells and/or immune cells, e.g., tumor infiltration lymphocytes (TILs), such as T reg cells) using the methods described herein is treated with any agent that modulates GITR signaling (e.g., an agonist anti-GITR antibody) and results in, e.g., the induction and/or enhancement of T cell activation (e.g., increase in IL-2 and/or IFN-γ production by T cells and/or increase in proliferation of T cells), depletion of regulatory T cells, etc. Accordingly, provided herein are methods of treating a cancer patient comprising:

(a) determining whether a tumor (tumor cells and/or immune cells, e.g., tumor infiltration lymphocytes (TILs), such as Treg cells) of a cancer patient is GITR-positive using the methods described herein, e.g., contacting a tumor sample from the patient with an antibody, or antigen-binding portion thereof, comprising heavy chain variable region CDR1, CDR2, and CDR3 comprising the amino acid sequences set forth in SEQ ID NOs: 5-7, respectively, and light chain variable region CDR1, CDR2, and CDR3 comprising the amino acid sequences set forth in SEQ ID NOs: 8-10, respectively, wherein the antibody or antigen-binding fragment thereof specifically binds to human GITR, detecting the binding of the antibody to GITR in the sample, and determining the level of GITR protein expression in the sample, wherein a level of GITR protein above a threshold level in tumor cells and/or immune cells therein, e.g., tumor infiltration lymphocytes (TILs), such as Treg cells, indicates that the tumor is GITR-positive, and (b) if the tumor is determined to be GITR-positive, then administering a therapeutically effective amount of an agent that modulates GITR signaling, e.g., an agent that increases IL-2, increases IFN-γ production by T cells, and/or increases the proliferation of T cells and/or depletion of regulatory T cells.

For example, in one embodiment, the patient is treated with a therapeutically-effective amount of an agonist anti-GITR antibody disclosed in WO15187835, the contents of which are herein incorporated by reference, e.g., antibodies having the heavy and light chain variable region CDRs, heavy and light chain variable regions, or heavy and light chains of antibodies 28F3, 19D3, 18E10, 3C3-1, 3C3-2, 2G6, 9G7-1, 9G7-2, 14E3, 19H8-1, 19H8-2, and/or 6G10, and variants thereof. The sequences of the antibodies disclosed in PCT Patent Application No. WO15187835 are provided in Table 2 (see SEQ ID NOs: 5-14 and 27-228). The patient may also be treated with any other anti-GITR antibodies, e.g., TRX518 (Leap Therapeutics), MK-4166 (Merck), LKZ-145 (Novartis), GWN-323 (Novartis Pharmaceuticals Corp.), Medi 1873 (MedImmune), INBRX-110 (Inhibrx), GITR-Fc protein (OncoMed) and antibodies described in WO2006105021, WO2009009116, WO2011028683, US2014/0072565, US20140072566, US20140065152, WO2015031667, WO15184099, WO2015184099, or WO2016054638.

Exemplary Methods of Monitoring GITR-Positive Tumors/Cancer

Provided herein are methods for monitoring a GITR-expressing tumor(s) in a cancer patient. Methods for monitoring may be performed in a similar manner to methods for determining whether a cancer patient is likely to respond to anti-GITR immunotherapy described above.

The presence of GITR may be monitored in whole tissues, e.g., tumors, or in specific cells thereof. For example, the presence of GITR may be monitored on tumor cells and/or tumor infiltrating lymphocytes (TILs), e.g., T reg cells and Teff cells.

Monitoring GITR presence (or expression) may comprise determining GITR presence at two or more time points. For example, a first and a second tissue sample may be obtained (and the presence and/or level of GITR determined) from a subject, wherein, e.g., the first and the second tissue sample are obtained within 3-7 days, 1 week to 3 weeks, or 1 month to 3 months from each other. A tissue sample may also be obtained for determining the presence and/or level of GITR every week or every month.

Accordingly, in certain embodiments, a method for monitoring a GITR-expressing tumor in a cancer patient comprises:

(a) detecting GITR protein expression in a tissue (e.g., tumor) sample at a first time point by using an anti-GITR antibody, or antigen-binding portion thereof, (b) determining the level of GITR protein expression at the first time point, (c) detecting GITR protein expression in a tissue (e.g., tumor, which may be the same tumor as the one that was biopsied at the first time point) sample at a second time point using the same antibody used in step (a), and (d) determining the level of GITR protein expression in the tumor from the second time point.

Also provided is a method for monitoring GITR-expressing tumor in a cancer patient comprising:

(a) detecting GITR protein expression in Treg cells in a tissue (e.g., tumor) sample at a first time point by using an anti-GITR antibody, or antigen-binding portion thereof, (b) determining the level of GITR protein expression at the first time point, (c) detecting GITR protein expression in Treg cells in a tissue (e.g., tumor, which may be the same tumor as the one that was biopsied at the first time point) sample at a second time point using the same antibody used in step (a), (d) determining the level of GITR protein expression in the Treg cells from the second time.

Also provided is a method for monitoring a GITR expressing tumor in a cancer patient comprising:

(a) detecting GITR protein expression in Teff cells in a tissue (e.g., tumor) sample at a first time point by using an anti-GITR antibody, or antigen-binding portion thereof, (b) determining the level of GITR protein expression at the first time point, (c) detecting GITR protein expression in Teff cells in a tissue (e.g., tumor, which may be the same tumor as the one that was biopsied at the first time point) sample at a second time point using the same antibody used in step (a), (d) determining the level of GITR protein expression in the Teff cells from the second time.

Also provided is a method for monitoring a GITR-expressing tumor in a cancer patient comprising:

(a) detecting GITR protein expression in tumor cells in a tumor sample at a first time point by using an anti-GITR antibody, or antigen-binding portion thereof, (b) determining the level of GITR protein expression at the first time point, (c) detecting GITR protein expression in tumor cells in a tumor sample (which may be from the same tumor as the one that was biopsied at the first time point) at a second time point using the same antibody used in step (a), (d) determining the level of GITR protein expression in the tumor cells from the second time.

In certain methods, the presence and/or level of GITR are determined in Treg cells and/or Teff cells and/or tumor cells.

Accordingly, in certain embodiments, a method for monitoring a GITR-expressing tumor in a cancer patient comprises:

(a) detecting GITR protein expression in the GITR-positive tumor at a first time point by using an anti-GITR antibody, or antigen-binding portion thereof, (b) determining the level of GITR protein expression at the first time point, (c) detecting GITR protein expression in the tumor at a second time point using the same antibody used in step (a), (d) determining the level of GITR protein expression in the tumor from the second time point; and (e) comparing the levels of GITR protein expression determined at the first and second time points.

GITR expression may be determined in the tumor cells and/or in immune cells, e.g., tumor infiltration lymphocytes (TILs), such as T reg cells and/or Teff cells within the tumor. A higher level at the first time point relative to the second time point may be indicative of tumor regression, a lower score at the first time point relative to the second time point may be indicative of tumor progression, and a relatively unchanged level at the first time point relative to the second time point may be indicative of a stable tumor.

In certain embodiments, the anti-GITR antibody used to determine the level of GITR protein expression is an antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, respectively, wherein the antibody or antigen-binding fragment thereof specifically binds to human GITR. In certain embodiments, the heavy chain lacks the C-terminal lysine. In some embodiments, the antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine. In a preferred embodiment, the detection of GITR expression is performed by immunohistochemistry, as described herein. In some embodiments, the level of GITR protein expression is determined using a scoring system selected from the group consisting of: the H score system, the Allred score system, an AQUA® system, or an automated scoring system, as described herein.

Such methods of monitoring are also useful for determining whether anti-GITR immunotherapy may be effective.

Accordingly, provided herein are methods for monitoring the efficacy of anti-GITR immunotherapy in a patient having a GITR-positive tumor comprising:

(a) detecting GITR protein expression in the GITR-positive tumor at a first time point before or after initiating anti-GITR immunotherapy by using an anti-GITR antibody, (b) determining the level of GITR protein expression in the tumor from the first time point, (c) detecting GITR protein expression in the GITR-positive tumor at a second time point after initiating anti-GITR immunotherapy using the same antibody from step (a), (d) determining the level of GITR protein expression in the tumor from the second time point;

(e) comparing the levels of GITR protein expression determined at the first and second time points, wherein a higher level at the first time point relative to the second time point may be indicative of effective anti-GITR immunotherapy, a lower score at the first time point relative to the second time point is indicative of ineffective anti-GITR immunotherapy, and an unchanged score at the first time point relative to the second time point may be indicative of anti-GITR immunotherapy being stabilizing. GITR expression may be determined in the tumor cells and/or in immune cells, e.g., tumor infiltration lymphocytes (TILs), such as T reg cells, within the tumor.

In certain embodiments, the anti-GITR antibody used to determine the level of GITR protein expression is an antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, or full length heavy and light chain sequences of antibody 6G10 (a fully human anti-GITR antibody) set forth in SEQ ID NOs: 13 and 14, respectively, wherein the antibody or antigen-binding fragment thereof specifically binds to human GITR. In certain embodiments, the heavy chain lacks the C-terminal lysine. In some embodiments, the antibody is a chimeric antibody comprising the variable regions of antibody 6G10, but non-human constant regions (e.g., mouse constant regions), e.g., a chimeric 6G10 antibody comprising the heavy and light chain sequences set forth in SEQ ID NOs: 15 and 16, respectively. In certain embodiments, the heavy chain of the chimeric antibody lacks the C-terminal lysine. In a preferred embodiment, the detection of GITR expression is performed by immunohistochemistry, as described herein. In some embodiments, the level of GITR protein expression is determined using a scoring system selected from the group consisting of: the H score system, the Allred score system, an AQUA® system, or an automated scoring system, as described herein.

In certain embodiments, the anti-GITR immunotherapy comprises administering to the cancer patient a therapeutically-effective amount of an anti-GITR antibody disclosed in WO15187835, the contents of which are herein incorporated by reference, e.g., antibodies having the heavy and light chain variable region CDRs, heavy and light chain variable regions, or heavy and light chains of antibodies 28F3, 19D3, 18E10, 3C3-1, 3C3-2, 2G6, 9G7-1, 9G7-2, 14E3, 19H8-1, 19H8-2, and/or 6G10, and variants thereof. The sequences of the antibodies disclosed in PCT Patent Application No. WO15187835 are provided in Table 2 (see SEQ ID NOs: 5-14 and 27-228). The patient may also be treated with any other anti-GITR antibodies, e.g., TRX518 (Leap Therapeutics), MK-4166 (Merck), LKZ-145 (Novartis), GWN-323 (Novartis Pharmaceuticals Corp.), Medi 1873 (MedImmune), INBRX-110 (Inhibrx), GITR-Fc protein (OncoMed) and antibodies described in WO2006105021, WO2009009116, WO2011028683, US2014/0072565, US20140072566, US20140065152, WO2015031667, WO15184099, WO2015184099, or WO2016054638.

In certain embodiments, the status of a GITR-expressing tumor can be monitored repeatedly after initial diagnosis (i.e., after making a determination that the tumor is GITR-positive), such as one month after initial diagnosis, two months after initial diagnosis, three months after initial diagnosis, four months after initial diagnosis, five months after initial diaimosis, six months after initial diagnosis, one year after initial diagnosis, etc. In other embodiments, the efficacy of anti-GITR immunotherapy against a GITR-expressing tumor can be monitored repeatedly after initiating anti-GITR immunotherapy, such as one month after initiation of therapy, two months after initiation of therapy, three months after initiation of therapy, four months after initiation of therapy, five months after initiation of therapy, six months after initiation of therapy, one year after initiation of therapy, etc.

Diagnostic Kits

Provided herein are kits which include the diagnostic anti-GITR antibodies described herein and instructions for use. Accordingly, in some embodiments, the kit comprises an antibody comprising the heavy and light chain variable region CDR sequences set forth in SEQ ID NOs: 5-7 and 8-10, respectively, heavy and light chain variable region sequences set forth in SEQ ID NOs: 11 and 12, respectively, wherein the antibody or antigen-binding fragment thereof specifically binds to human GITR, or full length heavy and light chain sequences of antibody 6G10 set forth in SEQ ID NOs: 13 and 14, respectively. In certain embodiments, the heavy chain lacks the C-terminal lysine. In some embodiments, the anti-GITR antibody is a chimeric antibody comprising the variable regions of antibody 6G10, but non-human constant regions (e.g., mouse constant regions), e.g., a chimeric antibody comprising the heavy and light chain sequences set forth in SEQ ID NOs: 15 and 16, respectively. In certain embodiments, the heavy chain of the chimeric antibody lacks the C-terminal lysine. In certain embodiments, the antibody comprises a detectable label, e.g., an antibody-label conjugate. Such kits may comprise at least one additional reagent. For example, in certain embodiments, the kits comprise buffers, stabilizers, substrates, immunodetection reagent (e.g., secondary antibodies for use in immunohistochemistry), and/or cofactors required for the assay. In certain embodiments, the antibody and, optionally the reagents, are suitably aliquoted. In certain embodiments, the kit comprises a means for obtaining the biological sample from a cancer patient. Such means can comprise, for example, reagents that can be used to obtain fluid or tissue sample from the cancer patient.

The present disclosure is further illustrated by the following examples, which should not be construed as further limiting. The contents of all figures and all references, Genbank sequences, patents and published patent applications cited throughout this application are expressly incorporated herein by reference. In particular, the disclosure of WO15187835 is expressly incorporated herein by reference.

EXAMPLES

Example 1: Generation of the 6G10 Antibody

The human anti-GITR antibody 6G10 was generated during the course of immunizing HuMAb® transgenic mice ("HuMAb" is a Trade Mark of Medarex, Inc., Princeton, N.J.) and KM mice (the KM Mouse® strain contains the SC20 transchromosome as described in PCT Publication WO 02/43478) and screening fusions for antibodies that bound to GITR (see concurrently filed PCT Application No. PCT/US15/33991). cDNA sequencing identified one heavy and one light chain for the 6G10 antibody. The variable region amino acid sequences and the isotype of the 6G10 antibody is set forth in FIGS. 1-4 and Table 2.

Example 2: Binding Properties of the 6G10 Antibody

Binding of the 6G10 antibody to soluble GITR was determined by Biacore. The 6G10 antibody was captured on human kappa coated chips (~5 KRUs; Southernbiotech), and recombinant human GITR (rHGITR/Fc: R&D systems) was flowed across the chip at concentrations of 500 nM, 250 nM, 125 nM, 62 nM, and 31 nM. The capture concentration of the antibody/volume was 2-40 μg/mL (5 μL at 10 μL/min). The antigen association time was 5 minutes at 15 μL/min, the antigen dissociation time was 6 minutes, and regeneration was performed with 50 mM HCl/50 mM NaOH (12 μL each at 100 μL/min). The 6G10 exhibited a $K_D$ of $1.87\times10^{-9}$ M for binding to soluble human GITR, with a $k_a$ of $3.83\times10^{5}$ $M^{-1}s^{-1}$ and a $k_d$ of 7.15×10 $s^{-1}$.

Example 3: Immunohistochemistry of Cancer Tissue with a Chimeric 6G10 Antibody Two immunohistochemistry (IHC) techniques were used to detect GITR in tissue sections: one IHC method was conducted on formalin fixed paraffin embedded (FFPE) tissue sections, and the other one was conducted on frozen tissue sections.

Several anti-GITR antibodies have been tested in these IHC methods and 6G10 was consistently better.

To detect GITR expression in human tissues, a fluoresceinated form of the 6G10 antibody was prepared and designated 6G10-FITC. To further develop a user and clinical friendly method, the 6G10 antibody was engineered to a mouse chimeric IgG2a format and optimized for automated immunohistochemistry using the Leica BondRX platform. The heavy and light chain sequences of the chimeric 6G10 antibody is set forth in FIGS. 5 and 6, respectively, and Table 2. The heavy chain may or may not contain a C-terminal lysine.

Briefly, slides were deparaffinized and rehydrated following routine histology procedures, and subjected to HIER (heat-induced antigen retrieval) manually with pH6 target retrieval buffer (Dako) for 10 min at 110° C. using Decloaking Chamber (BioCare Medical). Slides were then loaded onto the Leica BondRX automated immunohistochemistry stainer. Tissue sections were incubated with the chimeric 6G10 antibody at 0.5 μg/ml for 60 minutes, followed by detection with the Leica Bond Polymer Refine Detection System (DS9800) using the manufacturer's instructions. Briefly, the tissue sections were incubated with rabbit anti-mouse linker (Leica) for 30 minutes and Novolink Max polymer (Leica) for 30 minutes. Finally, slides were reacted with a DAB substrate-chromogen solution for 6 minutes. Slides were then counterstained with Mayer's hematoxylin, dehydrated, cleared, and coverslipped with Permount following routine histological procedure. Dako protein block supplemented with 0.5% Hu-gamma-globulins (Sigma) was used to block non-specific binding and PBS supplemented with 0.5% human gamma globulins and 0.5% BSA was used as diluent for both primary and secondary antibodies.

To profile tumor infiltrating lymphocytes (TILs), commercial monoclonal antibodies to CD3 (T cell marker) and FoxP3 (regulatory T cell marker) were used to stain adjacent sections. In-house engineered mouse chimeric human anti-KLH IgG2a and commercial mouse IgG1 were used as negative control antibodies. HEK-293T cells stably expressing human GITR and hyperplasic human tonsil tissue sections were used as positive controls. FFPE tissue samples from 5 tumor types were purchased from commercial tissue vendors, with 13-26 cases for each tumor type.

After immunostaining, the slides were examined under a light microscope. For scoring of GITR and TILs, an automated and quantitative analysis using Aperio® ScanScope and HALO™ image analysis software was performed on the whole slide. Representative images were taken either with Aperio ScanScope or Olympus DP71 digital microscope camera.

Table 1 summarizes the distribution of GITR positive TILs in cervical carcinoma (CC), melanoma (Mel), hepatocellular carcinoma (HCC), colorectal carcinoma (CRC), and head and neck squamous cell carcinoma (HNSCC). A manual score of 13 to 26 cases by estimation of number of positive cells under 20× objective of microscope. Minimum, <1 cells per 20× objective field; Mild, 1~<10 cells per 20× objective field; Moderate, 10~<50 cells per 20× objective field; Marked, 50~<200 cells per 20× objective; Intense, >200 cells per 20× objective field. At least ⅓ of the whole tumor section met the above criteria.

GITR-positive staining was present in a small fraction of TILs. In general, the abundance of GITR+ cells was in proportion to that of TILs. GITR-positive TILs were abundant in cervical carcinoma (CC), melanoma (Mel), and hepatocellular carcinoma (HCC), and some staining was also observed in colorectal carcinoma (CRC) and head and neck squamous cell carcinoma (HNSCC), among which cervical squamous cell carcinoma showed the most abundant staining.

GITR-positive staining was also observed in tumor cells in NSCLC (non-small cell lung carcinoma), CC, HNSCC, and HCC (FIG. 7). In NSCLC and CC, the specificity of the staining was confirmed by complete displacement of staining upon incubation with GITR fusion protein.

Immunohistochemistry was also performed on frozen tissue samples. Cryostat sections at 5 μm were fixed with acetone for 10 minutes and immunostained using an indirect immunoperoxidase method at room temperature. For staining with CD3 (T cell marker), CD8 (cytotoxic T cell marker), and FoxP3 (regulatory T cell marker) monoclonal antibodies, slides were further fixed with 10% NBF for 2 minutes. For staining with 6G10-FITC and HuIgG2-FITC, slides were immersed in 10% NBF for 1 minute. Peroxidase block supplied with the EnVision+System and Dako protein block supplemented with 0.5% human gamma globulins were used for endogenous peroxidase activity and nonspecific binding blocks, respectively. Primary antibodies (6G10-FITC at 5 μg/mL, CD3 at 1:100, CD8 at 1:100 or FoxP3 at 5 or 10 μg/mL) or an isotype control antibody (HuIgG2-FITC at 5 μg/mL) were applied to sections and incubated for 1 hour. The EnVison+system for either mouse or rabbit IgG was used as the detection system. For 6G10-FITC and its isotype control HuIgG2-FITC, rabbit anti-FITC antibody (5 μg/mL) was used as bridging antibody. Finally, slides were reacted with the DAB substrate-chromogen solution for 6 minutes, and then counterstained with Mayer's hematoxylin, dehydrated, cleared, and coverslipped with Permount using routine histological procedures. For CD3, CD8, and FoxP3 monoclonal antibodies, Dako protein block was used as the diluent, whereas for 6G10-FITC and HuIgG2-FITC, PBS supplemented with 0.5% human gamma globulins and 0.5% BSA was used as the diluent for both primary and secondary antibodies. Frozen tissue samples from 3 tumor types were purchased from commercial tissue vendors.

TABLE 1

| Staining intensity | Cervical carcinoma (n = 24) | Melanoma (n = 17) | Hepatocellular carcinoma (n = 25) | Colorectal carcinoma (n = 26) | Head and neck squamous cell carcinoma (n = 13) |
|---|---|---|---|---|---|
| Minimum | 0% | 6% | 8% | 12% | 15% |
| Mild | 0% | 24% | 16% | 15% | 23% |
| Moderate | 58% | 29% | 36% | 46% | 38% |
| Marked | 33% | 29% | 40% | 27% | 24% |
| Intense | 8% | 12% | 0% | 0% | 0% |

In hyperplastic tonsil, strong scattered positive cells were distributed in the interfollicular region and germinal center, as well as scattered epithelium-infiltrating lymphocytes. There was a tendency for more positive cells to be distributed in focal clusters of MNC beneath the epithelium. CD3+ TILs were present in all cancer samples examined, although the quantity varied across cancers and the distribution within the same tissue was heterogeneous. CD8+ TILs were present in the vast majority of tissues. In multiple cancers examined, Different amounts of GITR+ TILs were observed in the 3 tumor types. FoxP3 was present in a small subset of TILs. Staining of a subset of tumor cells with the anti-GITR antibody was also observed, and the specificity of the staining was confirmed by complete displacement of staining upon incubation with GITR fusion protein. The presence of GITR mRNA in GITR tumor cells was also observed by RNAscope on the frozen sections, which further confirms the IHC results.

These results indicate that anti-GITR antibody 6G10 can efficiently detect human GITR protein in fixed and frozen tissue samples.

TABLE 2

Summary table of sequences

| SEQ ID | DESCRIPTION | SEQUENCE |
|---|---|---|
| 1 | human GITR isoform 1 | MAQHGAMGAFRALCGLALLCALSLGQRPTGGPGCGPGRLLLGTGTDA<br>RCCRVHTTRCCRDYPGEECCSEWDCMCVQPEFHCGDPCCTTCRHHPC<br>PPGQGVQSQGKFSFGFQCIDCASGTFSGGHEGHCKPWTDCTQFGFLT<br>VFPGNKTHNAVCVPGSPPAEPLGWLTVVLLAVAACVLLLTSAQLGLH<br>IWQLRSQCMWPRETQLLLEVPPSTEDARSCQFPEEERGERSAEEKGR<br>LGDLWV |
| 2 | human GITR isoform 2 | MAQHGAMGAFRALCGLALLCALSLGQRPTGGPGCGPGRLLLGTGTDA<br>RCCRVHTTRCCRDYPGEECCSEWDCMCVQPEFHCGDPCCTTCRHHPC<br>PPGQGVQSQGKFSFGFQCIDCASGTFSGGHEGHCKPWTDCCWRCRRR<br>PKTPEAASSPRKSGASDRQRRRGGWETCGCEPGRPPGPPTAASPSPG<br>APQAAGALRSALGRALLPWQQKWVQEGGSDQRPGPCSSAAAAGPCRR<br>ERETQSWPPSSLAGPDGVGS |
| 3 | human GITR isoform 3 | MAQHGAMGAFRALCGLALLCALSLGQRPTGGPGCGPGRLLLGTGTDA<br>RCCRVHTTRCCRDYPGEECCSEWDCMCVQPEFHCGDPCCTTCRHHPC<br>PPGQGVQSQGKFSFGFQCIDCASGTFSGGHEGHCKPWTDCTQFGFLT<br>VFPGNKTHNAVCVPGSPPAEPLGWLTVVLLAVAACVLLLTSAQLGLH<br>IWQLRKTQLLLEVPPSTEDARSCQFPEEERGERSAEEKGRLGDLWV |
| 4 | extracellular portion of mature human GITR | QRPTGGPGCGPGRLLLGTGTDARCCRVHTTRCCRDYPGEECCSEWDC<br>MCVQPEFHCGDPCCTTCRHHPCPPGQGVQSQGKFSFGFQCIDCASGT<br>FSGGHEGHCKPWTDCTQFGFLTVFPGNKTHNAVCVPGSPPAEP |
| 5 | 6G10 VH CDR1 | TYGMH |
| 6 | 6G10 VH CDR2 | VTWYAGSNKFYADSVKG |
| 7 | 6G10 VH CDR3 | GGSMVRGLYYYGMDV |
| 8 | 6G10 VL CDR1 | RASQGISSALA |
| 9 | 6G10 VL CDR2 | DASSLES |
| 10 | 6G10 VL CDR3 | QQFNSYPYT |
| 11 | 6G10 VH | QVQLVESGGDVVQPGRSLRLSCAASGFTFSTYGMHWVRQAPGKGLEW<br>VAVTWYAGSNKFYADSVKGRFTISRDNSKNTLYLQMNSLRAEDTAVY<br>YCARGGSMVRGLYYYGMDVWGQGTTVTVSS |
| 12 | 6G10 VL | AIQLTQSPSSLSASVGDRVTITCRASQGISSALAWYQQKPGKAPKLL<br>IYDASSLESGVPSRFSGSGSGTDFTLTISSLQPEDFATYYCQQFNSY<br>PYTFGQGTKLEIK |
| 13 | 6G10 full length heavy chain | QVQLVESGGDVVQPGRSLRLSCAASGFTFSTYGMHWVRQAPGKGLEW<br>VAVTWYAGSNKFYADSVKGRFTISRDNSKNTLYLQMNSLRAEDTAVY<br>YCARGGSMVRGLYYYGMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPGK |
| 14 | 6G10 full length light chain | AIQLTQSPSSLSASVGDRVTITCRASQGISSALAWYQQKPGKAPKLL<br>IYDASSLESGVPSRFSGSGSGTDFTLTISSLQPEDFATYYCQQFNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 15 | chimeric 6G10 antibody-full length heavy chain<br>The constant region is underlined | QVQLVESGGDVVQPGRSLRLSCAASGFTFSTYGMHWVRQAPGKGLEW<br>VAVTWYAGSNKFYADSVKGRFTISRDNSKNTLYLQMNSLRAEDTAVY<br>YCARGGSMVRGLYYYGMDVWGQGTTVTVSSAKTTAPSVYPLAPVCGD<br>TTGSSVTLGCLVKGYFPEPVTLTWNSGSLSSGVHTFPAVLQSDLYTL<br>SSSVTVTSSTWPSQSITCNVAHPASSTKVDKKIEPRGPTIKPCPPCK<br>CPAPNLLGGPSVFIFPPKIKDVLMISLSPIVTCVVVDVSEDDPDVQI<br>SWFVNNVEVHTAQTQTHREDYNSTLRVVSALPIQHQDWMSGKEFKCK<br>VNNKDLPAPIERTISKPKGSVRAPQVYVLPPPEEEMTKKQVTLTCMV<br>TDFMPEDIYVEWTNNGKTELNYKNTEPVLDSDGSYFMYSKLRVEKKN<br>WVERNSYSCSVVHEGLHNHHTTKSFSRTPGK |

TABLE 2-continued

| Summary table of sequences | | |
| --- | --- | --- |
| SEQ ID | DESCRIPTION | SEQUENCE |
| 16 | chimeric 6G10 antibody-full length light chain<br>The constant region is underlined | AIQLTQSPSSLSASVGDRVTITCRASQGISSALAWYQQKPGKAPKLL<br>IYDASSLESGVPSRFSGSGSGTDFTLTISSLQPEDFATYYCQQFNSY<br>PYTFGQGTKLEIKRADAAPTVSIFPPSSEQLTSGGASVVCFLNNFYP<br>KDINVKWKIDGSERQNGVLNSWTDQDSKDSTYSMSSTLTLTKDEYER<br>HNSYTCEATHKTSTSPIVKSFNRNEC |
| 17 | 6G10 (VH) nucleotide sequence | CAGGTGCAGCTGGTGGAGTCTGGGGGAGACGTGGTCCAGCCTGGGAG<br>GTCCCTGAGACTCTCCTGTGCAGCGTCTGGATTCACCTTCAGTACCT<br>ATGGCATGCACTGGGTCCGCCAGGCTCCAGGCAAGGGGCTGGAGTGG<br>GTGGCAGTTACATGGTATGCTGGAAGTAATAAATTTTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGAGGAGGTAGTATGGTTCGGGGACTTTATTATTACGG<br>TATGGACGTCTGGGGCCAAGGGACCACGGTCACCGTCTCCTCA |
| 18 | 6G10 (VL) nucleotide sequence | GCCATCCAGTTGACCCAGTCTCCATCCTCCCTGTCTGCATCTGTAGG<br>AGACAGAGTCACCATCACTTGCCGGGCAAGTCAGGGCATTAGCAGTG<br>CTTTAGCCTGGTATCAGCAGAAACCAGGGAAAGCTCCTAAGCTCCTG<br>ATCTATGATGCCTCCAGTTTGGAAAGTGGGGTCCCATCAAGGTTCAG<br>CGGCAGTGGATCTGGGACAGATTTCACTCTCACCATCAGCAGCCTGC<br>AGCCTGAAGATTTTGCAACTTATTACTGTCAACAGTTTAATAGTTAC<br>CCGTACACTTTTGGCCAGGGGACCAAGCTGGAGATCAAA |
| 19 | 6G10 (full length wild-type heavy chain) nucleotide sequence<br>The sequence encoding the constant region is underlined | CAGGTGCAGCTGGTGGAGTCTGGGGGAGACGTGGTCCAGCCTGGGAG<br>GTCCCTGAGACTCTCCTGTGCAGCGTCTGGATTCACCTTCAGTACCT<br>ATGGCATGCACTGGGTCCGCCAGGCTCCAGGCAAGGGGCTGGAGTGG<br>GTGGCAGTTACATGGTATGCTGGAAGTAATAAATTTTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGAGGAGGTAGTATGGTTCGGGGACTTTATTATTACGG<br>TATGGACGTCTGGGGCCAAGGGACCACGGTCACCGTCTCCTCAGCCT<br>CCACCAAGGGCCCATCGGTCTTCCCCCTGGCGCCCTGCTCCAGGAGC<br>ACCTCCGAGAGCACAGCGGCCCTGGGCTGCCTGGTCAAGGACTACTT<br>CCCCGAACCGGTGACGGTGTCGTGGAACTCAGGCGCTCTGACCAGCG<br>GCGTGCACACCTTCCCAGCTGTCCTACAGTCCTCAGGACTCTACTCC<br>CTCAGCAGCGTGGTGACCGTGCCCTCCAGCAACTTCGGCACCCAGAC<br>CTACACCTGCAACGTAGATCACAAGCCCAGCAACACCAAGGTGGACA<br>AGACAGTTGAGCGCAAATGTTGTGTCGAGTGCCCACCGTGCCCAGCA<br>CCACCTGTGGCAGGACCGTCAGTCTTCCTCTTCCCCCCAAAACCCAA<br>GGACACCCTCATGATCTCCCGGACCCCTGAGGTCACGTGCGTGGTGG<br>TGGACGTGAGCCACGAAGACCCCGAGGTCCAGTTCAACTGGTACGTG<br>GACGGCGTGGAGGTGCATAATGCCAAGACAAAGCCACGGGAGGAGCA<br>GTTCAACAGCACGTTCCGTGTGGTCAGCGTCCTCACCGTTGTGCACC<br>AGGACTGGCTGAACGGCAAGGAGTACAAGTGCAAGGTCTCCAACAAA<br>GGCCTCCCAGCCCCCATCGAGAAAACCATCTCCAAAACCAAAGGGCA<br>GCCCCGAGAACCACAGGTGTACACCCTGCCCCCATCCCGGGAGGAGA<br>TGACCAAGAACCAGGTCAGCCTGACCTGCCTGGTCAAAGGCTTCTAC<br>CCCAGCGACATCGCCGTGGAGTGGGAGAGCAATGGGCAGCCGGAGAA<br>CAACTACAAGACCACACCTCCCATGCTGGACTCCGACGGCTCCTTCT<br>TCCTCTACAGCAAGCTCACCGTGGACAAGAGCAGGTGGCAGCAGGGG<br>AACGTCTTCTCATGCTCCGTGATGCATGAGGCTCTGCACAACCACTA<br>CACGCAGAAGAGCCTCTCCCTGTCTCCGGGTAAA |
| 20 | 6G10 (full length wild-type light chain) nucleotide sequence<br>The sequence encoding the constant region is underlined | GCCATCCAGTTGACCCAGTCTCCATCCTCCCTGTCTGCATCTGTAGG<br>AGACAGAGTCACCATCACTTGCCGGGCAAGTCAGGGCATTAGCAGTG<br>CTTTAGCCTGGTATCAGCAGAAACCAGGGAAAGCTCCTAAGCTCCTG<br>ATCTATGATGCCTCCAGTTTGGAAAGTGGGGTCCCATCAAGGTTCAG<br>CGGCAGTGGATCTGGGACAGATTTCACTCTCACCATCAGCAGCCTGC<br>AGCCTGAAGATTTTGCAACTTATTACTGTCAACAGTTTAATAGTTAC<br>CCGTACACTTTTGGCCAGGGGACCAAGCTGGAGATCAAACGAACTGT<br>GGCTGCACCATCTGTCTTCATCTTCCCGCCATCTGATGAGCAGTTGA<br>AATCTGGAACTGCCTCTGTTGTGTGCCTGCTGAATAACTTCTATCCC<br>AGAGAGGCCAAAGTACAGTGGAAGGTGGATAACGCCCTCCAATCGGG<br>TAACTCCCAGGAGAGTGTCACAGAGCAGGACAGCAAGGACAGCACCT<br>ACAGCCTCAGCAGCACCCTGACGCTGAGCAAAGCAGACTACGAGAAA<br>CACAAAGTCTACGCCTGCGAAGTCACCCATCAGGGCCTGAGCTCGCC<br>CGTCACAAAGAGCTTCAACAGGGGAGAGTGT |
| 21 | chimeric 6G10 heavy chain<br>The sequence encoding the constant region is underlined | CAGGTGCAGCTGGTGGAGTCTGGGGGAGACGTGGTCCAGCCTGGGAG<br>GTCCCTGAGACTCTCCTGTGCAGCGTCTGGATTCACCTTCAGTACCT<br>ATGGCATGCACTGGGTCCGCCAGGCTCCAGGCAAGGGGCTGGAGTGG<br>GTGGCAGTTACATGGTATGCTGGAAGTAATAAATTTTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGAGGAGGTAGTATGGTTCGGGGACTTTATTATTACGG |

TABLE 2-continued

| Summary table of sequences | | |
|---|---|---|
| SEQ ID | DESCRIPTION | SEQUENCE |
| | | TATGGACGTCTGGGGCCAAGGGACCACGGTCACCGTCTCCTCAGCCA<br>AAACAACAGCCCCATCGGTCTATCCGCTAGCCCCTGTGTGTGGAGAT<br>ACAACTGGCTCCTCGGTGACTCTAGGATGCCTGGTCAAGGGTTATTT<br>CCCTGAGCCAGTGACCTTGACCTGGAACTCTGGATCCCTGTCCAGTG<br>GTGTGCACACCTTCCCAGCTGTCCTGCAGTCTGACCTCTACACCCTC<br>AGCAGCTCAGTGACTGTAACCTCGAGCACCTGGCCCAGCCAGTCCAT<br>CACCTGCAATGTGGCCCACCCGGCAAGCAGCACCAAGGTGGACAAGA<br>AAATTGAGCCCAGAGGGCCCACAATCAAGCCCTGTCCTCCATGCAAA<br>TGCCCAGCACCTAACCTCTTGGGTGGACCATCCGTCTTCATCTTCCC<br>TCCAAAGATCAAGGATGTACTCATGATCTCCCTGAGCCCCATAGTCA<br>CATGTGTGGTGGTGGATGTGAGCGAGGATGACCCAGATGTCCAGATC<br>AGCTGGTTTGTGAACAACGTGGAAGTACACACAGCTCAGACACAAAC<br>CCATAGAGAGGATTACAACAGTACTCTCCGGGTGGTCAGTGCCCTCC<br>CCATCCAGCACCAGGACTGGATGAGTGGCAAGGAGTTCAAATGCAAG<br>GTCAACAACAAAGACCTCCCAGCGCCCATCGAGAGAACCATCTCAAA<br>ACCCAAAGGGTCAGTAAGAGCTCCACAGGTATATGTCTTGCCTCCAC<br>CAGAAGAAGAGATGACTAAGAAACAGGTCACTCTGACCTGCATGGTC<br>ACAGACTTCATGCCTGAAGACATTTACGTGGAGTGGACCAACAACGG<br>GAAAACAGAGCTAAACTACAAGAACACTGAACCAGTCCTGGACTCTG<br>ATGGTTCTTACTTCATGTACAGCAAGCTGAGAGTGGAAAAGAAGAAC<br>TGGGTGGAAAGAAATAGCTACTCCTGTTCAGTGGTCCACGAGGGTCT<br>GCACAATCACCACACGACTAAGAGCTTCTCCCGGACTCCGGGTAAAT<br>GA |
| 22 | chimeric 6G10 light chain<br>The sequence encoding the<br>constant region is underlined | GCCATCCAGTTGACCCAGTCTCCATCCTCCCTGTCTGCATCTGTAGG<br>AGACAGAGTCACCATCACTTGCCGGGCAAGTCAGGGCATTAGCAGTG<br>CTTTAGCCTGGTATCAGCAGAAACCAGGGAAAGCTCCTAAGCTCCTG<br>ATCTATGATGCCTCCAGTTTGGAAAGTGGGGTCCCATCAAGGTTCAG<br>CGGCAGTGGATCTGGGACAGATTTCACTCTCACCATCAGCAGCCTGC<br>AGCCTGAAGATTTTGCAACTTATTACTGTCAACAGTTTAATAGTTAC<br>CCGTACACTTTTGGCCAGGGGACCAAGCTGGAGATCAAACGGGCTGA<br>TGCTGCACCAACTGTATCCATCTTCCCACCATCCAGTGAGCAATTGA<br>CATCTGGAGGTGCCTCAGTCGTGTGCTTCTTGAACAACTTCTACCCC<br>AAAGACATCAATGTCAAGTGGAAGATTGATGGCAGTGAACGACAAAA<br>TGGCGTCCTGAACAGTTGGACCGATCAGGACAGCAAAGACAGCACCT<br>ACAGCATGAGCAGCACCCTCACGTTGACCAAGGACGAGTATGAACGA<br>CATAACAGCTATACCTGTGAGGCCACTCACAAGACATCAACTTCACC<br>CATTGTCAAGAGCTTCAACAGGAATGAGTGTTAG |
| 23 | human IgG2 heavy chain<br>constant region | ASTKGPSVFPLAPCSRSTSESTAALGCLVKDYFPEPVTVSWNSGALT<br>SGVHTFPAVLQSSGLYSLSSVVTVPSSNFGTQTYTCNVDHKPSNTKV<br>DKTVERKCCVECPPCPAPPVAGPSVFLFPPKPKDTLMISRTPEVTCV<br>VVDVSHEDPEVQFNWYVDGVEVHNAKTKPREEQFNSTFRVVSVLTVV<br>HQDWLNGKEYKCKVSNKGLPAPIEKTISKTKGQPREPQVYTLPPSRE<br>EMTKNQVSLTCLVKGFYPSDIAVEWESNGQPENNYKTTPPMLDSDGS<br>FFLYSKLTVDKSRWQQGNVFSCSVMHEALHNHYTQKSLSLSPGK |
| 24 | human kappa light chain<br>constant region | RTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGL<br>SSPVTKSFNRGEC |
| 25 | mouse IgG2a heavy chain<br>constant region | AKTTAPSVYPLAPVCGDTTGSSVTLGCLVKGYFPEPVTLTWNSGSLS<br>SGVHTFPAVLQSDLYTLSSSVTVTSSTWPSQSITCNVAHPASSTKVD<br>KKIEPRGPTIKPCPPCKCPAPNLLGGPSVFIFPPKIKDVLMISLSPI<br>VTCVVVDVSEDDPDVQISWFVNNVEVHTAQTQTHREDYNSTLRVVSA<br>LPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLD<br>SDGSYFMYSKLRVEKKNWVERNSYSCSVVHEGLHNHHTTKSFSRTPG<br>K |
| 26 | mouse kappa light chain constant<br>region | RADAAPTVSIFPPSSEQLTSGGASVVCFLNNFYPKDINVKWKIDGSE<br>RQNGVLNSWTDQDSKDSTYSMSSTLTLTKDEYERHNSYTCEATHKTS<br>TSPIVKSFNRNEC |
| 27 | 28F3 (VH) | QVQLVESGGGVVQPGRSLRLSCAASGFTFSSYGMHWVRQAPGKGLEW<br>VAVIWYEGSNKYYADSVKGRFTISRDNSKNTLYLQMNSLRAEDTAVY<br>YCARGGSMVRGDYYYGMDVWGQGTTVTVSS |
| 28 | 28F3 (VL) | AIQLTQSPSSLSASVGDRVTITCRASQGISSALAWYQQKPGKAPKLL<br>IYDASSLESGVPSRFSGSGSGTDFTLTISSLQPEDFATYYCQQFNSY<br>PYTFGQGTKLEIK |
| 29 | 28F3 (full length wild-type<br>heavy chain)<br>The constant region is<br>underlined | QVQLVESGGGVVQPGRSLRLSCAASGFTFSSYGMHWVRQAPGKGLEW<br>VAVIWYEGSNKYYADSVKGRFTISRDNSKNTLYLQMNSLRAEDTAVY<br>YCARGGSMVRGDYYYGMDVWGQGTTVTVSSASTKGPSVFPLAPCSRS<br>TSESTAALGCLVKDYFPEPVTVSWNSGALTSGVHTFPAVLQSSGLYS |

TABLE 2-continued

| Summary table of sequences | | |
|---|---|---|
| SEQ ID | DESCRIPTION | SEQUENCE |
| | | LSSVVTVPSSNFGTQTYTCNVDHKPSNTKVDKTVERKCCVECPPCPA PPVAGPSVFLFPPKPKDTLMISRTPEVTCVVVDVSHEDPEVQFNWYV DGVEVHNAKTKPREEQFNSTFRVVSVLTVVHQDWLNGKEYKCKVSNK GLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPGK |
| 30 | 28F3 (full length wild-type light chain) The constant region is underlined | AIQLTQSPSSLSASVGDRVTITCRASQGISSALAWYQQKPGKAPKLL IYDASSLESGVPSRFSGSGSGTDFTLTISSLQPEDFATYYCQQFNSY PYTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 31 | 28F3.IgG1 (VH + IgG1) | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 32 | 28F3.IgG1.1 (VH + IgG1.1) | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCK VSNKALPSSIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 33 | 28F3.IgG1 (VL + CL) | AIQLTQSPSSLSASVGDRVTITCRASQGISSALAWYQQKPGKAPKLL IYDASSLESGVPSRFSGSGSGTDFTLTISSLQPEDFATYYCQQFNSY PYTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 34 | 28F3 VH CDR1 | SYGMH |
| 35 | 28F3 VH CDR2 | VIWYEGSNKYYADSVKG |
| 36 | 28F3 VH CDR3 | GGSMVRGDYYYGMDV |
| 37 | 28F3 VL CDR1 | RASQGISSALA |
| 38 | 28F3 VL CDR2 | DASSLES |
| 39 | 28F3 VL CDR3 | QQFNSYPYT |
| 40 | 28F3 (VH + G2(C219S)) or 28F3-IgG2-C219S | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVQFNWYV DGVEVHNAKTKPREEQFNSTFRVVSVLTVVHQDWLNGKEYKCKVSNK GLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG |
| 41 | 28F3 (VH + G2.g1) or 28F3-IgG2-IgG1 | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |

TABLE 2-continued

Summary table of sequences

| SEQ ID | DESCRIPTION | SEQUENCE |
|---|---|---|
| 42 | 28F3 (VH + G2.g1.1) or 28F3-IgG2-IgG1.1 | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 43 | 28F3 (VH + G2(C219S).g1) or 28F3-IgG2-C219S-IgG1 | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 44 | 28F3 (VH + G2(C219S).g1.1) or 28F3-IgG2-C219S-IgG1.1 | QVQLVESGGGVVQPGRSLRLSCAASGFTFSSYGMHWVRQAPGKGLEW VAVIWYEGSNKYYADSVKGRFTISRDNSKNTLYLQMNSLRAEDTAVY YCARGGSMVRGDYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 45 | 28F3 (VH) (SEQ ID NO: 13) with signal peptide The signal peptide is underlined | MRAWIFFLLCLAGRALAQVQLVESGGGVVQPGRSLRLSCAASGFTFS SYGMHWVRQAPGKGLEWVAVIWYEGSNKYYADSVKGRFTISRDNSKN TLYLQMNSLRAEDTAVYYCARGGSMVRGDYYYGMDVWGQGTTVTVSS |
| 46 | 28F3 (VL) (SEQ ID NO: 14) with signal peptide The signal peptide is underlined | MRAWIFFLLCLAGRALAAIQLTQSPSSLSASVGDRVTITCRASQGIS SALAWYQQKPGKAPKLLIYDASSLESGVPSRFSGSGSGTDFTLTISS LQPEDFATYYCQQFNSYPYTFGQGTKLEIK |
| 47 | 28F3.IgG1 (VH + IgG1) with signal peptide The signal peptide and constant region are underlined | MRAWIFFLLCLAGRALAQVQLVESGGGVVQPGRSLRLSCAASGFTFS SYGMHWVRQAPGKGLEWVAVIWYEGSNKYYADSVKGRFTISRDNSKN TLYLQMNSLRAEDTAVYYCARGGSMVRGDYYYGMDVWGQGTTVTVSS ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHEALHNHYTQKSLSLSPG |
| 48 | 28F3.IgG1.1 (VH + IgG1.1) with signal peptide The signal peptide and constant region are underlined | MRAWIFFLLCLAGRALAQVQLVESGGGVVQPGRSLRLSCAASGFTFS SYGMHWVRQAPGKGLEWVAVIWYEGSNKYYADSVKGRFTISRDNSKN TLYLQMNSLRAEDTAVYYCARGGSMVRGDYYYGMDVWGQGTTVTVSS ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPEAEGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPSSIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHEALHNHYTQKSLSLSPG |
| 49 | 28F3.IgG1 (VL + CL) with signal peptide The signal peptide and constant region are underlined | MRAWIFFLLCLAGRALAAIQLTQSPSSLSASVGDRVTITCRASQGIS SALAWYQQKPGKAPKLLIYDASSLESGVPSRFSGSGSGTDFTLTISS LQPEDFATYYCQQFNSYPYTFGQGTKLEIKRTVAAPSVFIFPPSDEQ LKSGTASVVCLLNNFYPREAKVQWKVDNALQSGNSQESVTEQDSKDS TYSLSSTLTLSKADYEKHKVYACEVTHQGLSSPVTKSFNRGEC |
| 50 | 19D3 (VH) | QVQLVESGGGVVQPGRSLRLSCAASGFTFSSYGFHWVRQAPGKGLEW VAVIWYAGSNKFYADSVKGRFTISRDNSKNTLYLQMNSLRAEDTAVY YCARGGQLDYYYYYVMDVWGQGTTVTVSS |

TABLE 2-continued

Summary table of sequences

| SEQ ID | DESCRIPTION | SEQUENCE |
|---|---|---|
| 51 | 19D3 (VL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIK |
| 52 | 19D3 (full length wild-type heavy chain)<br>The constant region is underlined | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVD<br>GVEVHNAKTKPREEQFNSTFRVVSVLTVVHQDWLNGKEYKCKVSNKG<br>LPAPIEKTISKTKGQPREPQVYTLPPSREEMTKNQVSLTCLVKGFYP<br>SDIAVEWESNGQPENNYKTTPPMLDSDGSFFLYSKLTVDKSRWQQGN<br>VFSCSVMHEALHNHYTQKSLSLSPGK |
| 53 | 19D3 (full length wild-type light chain)<br>The constant region is underlined | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 54 | 19D3.IgG1 (VH + IgG1) | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPSSKST<br>SGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPG |
| 55 | 19D3.IgG1.1 (VH + IgG1.1) | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPSSKST<br>SGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPC<br>PAPEAEGAPSVFLFPPKPKDTLMISRTPEVTCVVVDVSHEDPEVKFN<br>WYVDGVEVHNAKTKPREEQYNSTYRVVSVLTVLHQDWLNGKEYKCKV<br>SNKALPSSIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPG |
| 56 | 19D3.IgG1 (VL + CL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 57 | 19D3 VH CDR1 | SYGFH |
| 58 | 19D3 VH CDR2 | VIWYAGSNKFYADSVKG |
| 59 | 19D3 VH CDR3 | GGQLDYYYYYVMDV |
| 60 | 19D3 VL CDR1 | RASQGISSWLA |
| 61 | 19D3 VL CDR2 | AASSLQS |
| 62 | 19D3 VL CDR3 | QQYNSYPYT |
| 63 | 19D3 (VH + G2(C219S)) or<br>19D3-IgG2-C219S | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>PVAGPSVFLFPPKPKDTLMISRTPEVTCVVVDVSHEDPEVQFNWYVD<br>GVEVHNAKTKPREEQFNSTFRVVSVLTVVHQDWLNGKEYKCKVSNKG<br>LPAPIEKTISKTKGQPREPQVYTLPPSREEMTKNQVSLTCLVKGFYP<br>SDIAVEWESNGQPENNYKTTPPMLDSDGSFFLYSKLTVDKSRWQQGN<br>VFSCSVMHEALHNHYTQKSLSLSPG |
| 64 | 19D3 (VH + G2.g1) or<br>19D3-IgG2-IgG1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST |

TABLE 2-continued

Summary table of sequences

| SEQ ID | DESCRIPTION | SEQUENCE |
|---|---|---|
| | | SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 65 | 19D3 (VH + G2.g1.1) or<br>19D3-IgG2-IgG1.1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>PVAGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPSSIEKTISKAKGQPREPQVYTLPPSREEMTKNQVSLTCLVKGFYP<br>SDIAVEWESNGQPENNYKTTPPVLDSDGSFFLYSKLTVDKSRWQQGN<br>VFSCSVMHEALHNHYTQKSLSLSPG |
| 66 | 19D3 (VH + G2(C219S).g1) or<br>19D3-IgG2-C219S-IgG1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 67 | 19D3 (VH + G2(C219S).g1.1) or<br>19D3-IgG2-C219S-IgG1.1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>PVAGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPSSIEKTISKAKGQPREPQVYTLPPSREEMTKNQVSLTCLVKGFYP<br>SDIAVEWESNGQPENNYKTTPPVLDSDGSFFLYSKLTVDKSRWQQGN<br>VFSCSVMHEALHNHYTQKSLSLSPG |
| 68 | 19D3 (VH + G2(C219S)) or<br>19D3-IgG2-C219S | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>PVAGPSVFLFPPKPKDTLMISRTPEVTCVVVDVSHEDPEVQFNWYVD<br>GVEVHNAKTKPREEQFNSTFRVVSVLTVVHQDWLNGKEYKCKVSNKG<br>LPAPIEKTISKTKGQPREPQVYTLPPSREEMTKNQVSLTCLVKGFYP<br>SDIAVEWESNGQPENNYKTTPPMLDSDGSFFLYSKLTVDKSRWQQGN<br>VFSCSVMHEALHNHYTQKSLSLSPG |
| 69 | 19D3 (VH + G2.g1) or<br>19D3-IgG2-IgG1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 70 | 19D3 (VH + G2.g1.1) or<br>19D3-IgG2-IgG1.1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>PVAGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPSSIEKTISKAKGQPREPQVYTLPPSREEMTKNQVSLTCLVKGFYP<br>SDIAVEWESNGQPENNYKTTPPVLDSDGSFFLYSKLTVDKSRWQQGN<br>VFSCSVMHEALHNHYTQKSLSLSPG |
| 71 | 19D3 (VH + G2(C219S).g1) or<br>19D3-IgG2-C219S-IgG1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY |

TABLE 2-continued

Summary table of sequences

| SEQ ID | DESCRIPTION | SEQUENCE |
|---|---|---|
| | | YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 72 | 19D3 (VH + G2(C219S).g1.1) or<br>19D3-IgG2-C219S-IgG1.1 | QVQLVESGGGVVQPGRSLRLSCAASGFTFSSYGFHWVRQAPGKGLEW<br>VAVIWYAGSNKFYADSVKGRFTISRDNSKNTLYLQMNSLRAEDTAVY<br>YCARGGQLDYYYYYVMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKSCVECPPCPAP<br>PVAGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPSSIEKTISKAKGQPREPQVYTLPPSREEMTKNQVSLTCLVKGFYP<br>SDIAVEWESNGQPENNYKTTPPVLDSDGSFFLYSKLTVDKSRWQQGN<br>VFSCSVMHEALHNHYTQKSLSLSPG |
| 73 | 18E10 (VH) | QVQLVESGGGVVQPGRSLRLSCAASGFTFSSYGMHWVRQAPGKGLEW<br>VAVIWYAGSNKYYADSVKGRFTISRDNSKNTLYLQMNSLRAEDTAVY<br>YCARGGRIAVAFYYSMDVWGQGTTVTVSS |
| 74 | 18E10 (VL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIK |
| 75 | 18E10 (full length wild-type<br>heavy chain)<br>The constant region is<br>underlined | QVQLVESGGGVVQPGRSLRLSCAASGFTFSSYGMHWVRQAPGKGLEW<br>VAVIWYAGSNKYYADSVKGRFTISRDNSKNTLYLQMNSLRAEDTAVY<br>YCARGGRIAVAFYYSMDVWGQGTTVTVSSASTKGPSVFPLAPCSRST<br>SESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVD<br>GVEVHNAKTKPREEQFNSTFRVVSVLTVVHQDWLNGKEYKCKVSNKG<br>LPAPIEKTISKTKGQPREPQVYTLPPSREEMTKNQVSLTCLVKGFYP<br>SDIAVEWESNGQPENNYKTTPPMLDSDGSFFLYSKLTVDKSRWQQGN<br>VFSCSVMHEALHNHYTQKSLSLSPGK |
| 76 | 18E10 (full length wild-type<br>light chain)<br>The constant region is<br>underlined | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 77 | 18E10.IgG1 (VH + IgG1) | QVQLVESGGGVVQPGRSLRLSCAASGFTFSSYGMHWVRQAPGKGLEW<br>VAVIWYAGSNKYYADSVKGRFTISRDNSKNTLYLQMNSLRAEDTAVY<br>YCARGGRIAVAFYYSMDVWGQGTTVTVSSASTKGPSVFPLAPSSKST<br>SGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPG |
| 78 | 18E10.IgG1.1 (VH + IgG1.1) | QVQLVESGGGVVQPGRSLRLSCAASGFTFSSYGMHWVRQAPGKGLEW<br>VAVIWYAGSNKYYADSVKGRFTISRDNSKNTLYLQMNSLRAEDTAVY<br>YCARGGRIAVAFYYSMDVWGQGTTVTVSSASTKGPSVFPLAPSSKST<br>SGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPC<br>PAPEAEGAPSVFLFPPKPKDTLMISRTPEVTCVVVDVSHEDPEVKFN<br>WYVDGVEVHNAKTKPREEQYNSTYRVVSVLTVLHQDWLNGKEYKCKV<br>SNKALPSSIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPG |
| 79 | 18E10.IgG1 (VL + CL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 80 | 18E10 VH CDR1 | SYGMH |
| 81 | 18E10 VH CDR2 | VIWYAGSNKYYADSVKG |

TABLE 2-continued

| Summary table of sequences | | |
|---|---|---|
| SEQ ID | DESCRIPTION | SEQUENCE |
| 82 | 18E10 VH CDR3 | GGRIAVAFYYSMDV |
| 83 | 18E10 VL CDR1 | RASQGISSWLA |
| 84 | 18E10 VL CDR2 | AASSLQS |
| 85 | 18E10 VL CDR3 | QQYNSYPYT |
| 86 | 18E10 (VH + G2(C219S)) or 18E10-IgG2-C219S | QVQLVESGGGVVQPGRSLRLSCAASGFTFSSYGMHWVRQAPGKGLEW VAVIWYAGSNKYYADSVKGRFTISRDNSKNTLYLQMNSLRAEDTAVY YCARGGRIAVAFYYSMDVWGQGTTVTVSSASTKGPSVFPLAPCSRST SESTAALGCLVKDYFPEPVTVSWNSGALTSGVHTFPAVLQSSGLYSL SSVVTVPSSNFGTQTYTCNVDHKPSNTKVDKTVERKSCVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSNKG LPAPIEKTISKTKGQPREPQVYTLPPSREEMTKNQVSLTCLVKGFYP SDIAVEWESNGQPENNYKTTPPMLDSDGSFFLYSKLTVDKSRWQQGN VFSCSVMHEALHNHYTQKSLSLSPG |
| 87 | 18E10 (VH + G2.g1) or 18E10-IgG2-IgG1 | QVQLVESGGGVVQPGRSLRLSCAASGFTFSSYGMHWVRQAPGKGLEW VAVIWYAGSNKYYADSVKGRFTISRDNSKNTLYLQMNSLRAEDTAVY YCARGGRIAVAFYYSMDVWGQGTTVTVSSASTKGPSVFPLAPCSRST SESTAALGCLVKDYFPEPVTVSWNSGALTSGVHTFPAVLQSSGLYSL SSVVTVPSSNFGTQTYTCNVDHKPSNTKVDKTVERKCCVECPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 88 | 18E10 (VH + G2.g1.1) or 18E10-IgG2-IgG1.1 | QVQLVESGGGVVQPGRSLRLSCAASGFTFSSYGMHWVRQAPGKGLEW VAVIWYAGSNKYYADSVKGRFTISRDNSKNTLYLQMNSLRAEDTAVY YCARGGRIAVAFYYSMDVWGQGTTVTVSSASTKGPSVFPLAPCSRST SESTAALGCLVKDYFPEPVTVSWNSGALTSGVHTFPAVLQSSGLYSL SSVVTVPSSNFGTQTYTCNVDHKPSNTKVDKTVERKCCVECPPCPAP PVAGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPSSIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| 89 | 18E10 (VH + G2(C219S).g1) or 18E10-IgG2-C219S-IgG1 | QVQLVESGGGVVQPGRSLRLSCAASGFTFSSYGMHWVRQAPGKGLEW VAVIWYAGSNKYYADSVKGRFTISRDNSKNTLYLQMNSLRAEDTAVY YCARGGRIAVAFYYSMDVWGQGTTVTVSSASTKGPSVFPLAPCSRST SESTAALGCLVKDYFPEPVTVSWNSGALTSGVHTFPAVLQSSGLYSL SSVVTVPSSNFGTQTYTCNVDHKPSNTKVDKTVERKSCVECPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 90 | 18E10 (VH + G2(C219S).g1.1) or 18E10-IgG2-C219S-IgG1.1 | QVQLVESGGGVVQPGRSLRLSCAASGFTFSSYGMHWVRQAPGKGLEW VAVIWYAGSNKYYADSVKGRFTISRDNSKNTLYLQMNSLRAEDTAVY YCARGGRIAVAFYYSMDVWGQGTTVTVSSASTKGPSVFPLAPCSRST SESTAALGCLVKDYFPEPVTVSWNSGALTSGVHTFPAVLQSSGLYSL SSVVTVPSSNFGTQTYTCNVDHKPSNTKVDKTVERKSCVECPPCPAP PVAGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPSSIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| 91 | 3C3 (VH) | QVQLQQWGAGLLKPSETLSLTCAVYGGSFSGYYWTWIRQPPGKGLEW IGKINHSGNTNYNPSLKSRVTISVDTSKNQFSLKLSSVTAADTAVYY CARLGAFDAFDIWGQGTMVTVSS |
| 92 | 3C3 (VL1) | DIQMTQSPSSLSASVGDRVTITCRASQGISSWLAWYQQKPEKAPKSL IYAASSLQSGVPSRFSGSGSGTDFTLTISSLQPEDFATYYCQQYNSY PYTFGQGTKLEIK |
| 93 | 3C3 (VL2) | EIVLTQSPATLSLSPGERATLSCRASQGVSSYLAWYQQKPGQAPRLL IYDASNRATGIPARFSGSGPGTDFTLTISSLEPEDFAVYYCQQRSNW HTFGQGTKLEIK |

TABLE 2-continued

Summary table of sequences

| SEQ ID | DESCRIPTION | SEQUENCE |
|---|---|---|
| 94 | 3C3 (full length wild-type heavy chain) The constant region is underlined | QVQLQQWGAGLLKPSETLSLTCAVYGGSFSGYYWTWIRQPPGKGLEW IGKINHSGNTNYNPSLKSRVTISVDTSKNQFSLKLSSVTAADTAVYY CARLGAFDAFDIWGQGTMVTVSS<u>ASTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKRVEPKSCDKTHTCPPCPAPELL GGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSD IAVEWESNGQPENNYKTTPPVLDSDGSFFLYSKLTVDKSRWQQGNVF SCSVMHEALHNHYTQKSLSLSPGK</u> |
| 95 | 3C3 L1 (full length wild-type light chain 1) The constant region is underlined | DIQMTQSPSSLSASVGDRVTITCRASQGISSWLAWYQQKPEKAPKSL IYAASSLQSGVPSRFSGSGSGTDFTLTISSLQPEDFATYYCQQYNSY PYTFGQGTKLEIK<u>RTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC</u> |
| 96 | 3C3 L2 (full length wild-type light chain 2) The constant region is underlined | EIVLTQSPATLSLSPGERATLSCRASQGVSSYLAWYQQKPGQAPRLL IYDASNRATGIPARFSGSGPGTDFTLTISSLEPEDFAVYYCQQRSNW HTFGQGTKLEIK<u>RTVAAPSVFIFPPSDEQLKSGTASVVCLLNNFYPR EAKVQWKVDNALQSGNSQESVTEQDSKDSTYSLSSTLTLSKADYEKH KVYACEVTHQGLSSPVTKSFNRGEC</u> |
| 97 | 3C3.IgG1 (VH + IgG1) | QVQLQQWGAGLLKPSETLSLTCAVYGGSFSGYYWTWIRQPPGKGLEW IGKINHSGNTNYNPSLKSRVTISVDTSKNQFSLKLSSVTAADTAVYY CARLGAFDAFDIWGQGTMVTVSSASTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKRVEPKSCDKTHTCPPCPAPELL GGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSREEMTKNQVSLTCLVKGFYPSD IAVEWESNGQPENNYKTTPPVLDSDGSFFLYSKLTVDKSRWQQGNVF SCSVMHEALHNHYTQKSLSLSPG |
| 98 | 3C3.IgG1.1 (VH + IgG1.1) | QVQLQQWGAGLLKPSETLSLTCAVYGGSFSGYYWTWIRQPPGKGLEW IGKINHSGNTNYNPSLKSRVTISVDTSKNQFSLKLSSVTAADTAVYY CARLGAFDAFDIWGQGTMVTVSSASTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKRVEPKSCDKTHTCPPCPAPE<u>AE GA</u>PSVFLFPPKPKDTLMISRTPEVTCVVVDVSHEDPEVKFNWYVDGV EVHNAKTKPREEQYNSTYRVVSVLTVLHQDWLNGKEYKCKVSNKALP <u>SS</u>IEKTISKAKGQPREPQVYTLPPSREEMTKNQVSLTCLVKGFYPSD IAVEWESNGQPENNYKTTPPVLDSDGSFFLYSKLTVDKSRWQQGNVF SCSVMHEALHNHYTQKSLSLSPG |
| 99 | 3C3.IgG1 (VL1 + CL) | DIQMTQSPSSLSASVGDRVTITCRASQGISSWLAWYQQKPEKAPKSL IYAASSLQSGVPSRFSGSGSGTDFTLTISSLQPEDFATYYCQQYNSY PYTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 100 | 3C3IgG1.2 (VL2 + CL) | EIVLTQSPATLSLSPGERATLSCRASQGVSSYLAWYQQKPGQAPRLL IYDASNRATGIPARFSGSGPGTDFTLTISSLEPEDFAVYYCQQRSNW HTFGQGTKLEIKRTVAAPSVFIFPPSDEQLKSGTASVVCLLNNFYPR EAKVQWKVDNALQSGNSQESVTEQDSKDSTYSLSSTLTLSKADYEKH KVYACEVTHQGLSSPVTKSFNRGEC |
| 101 | 3C3 VH CDR1 | GYYWT |
| 102 | 3C3 VH CDR2 | KINHSGNTNYNPSLKS |
| 103 | 3C3 VH CDR3 | LGAFDAFDI |
| 104 | 3C3 VL1 CDR1 | RASQGISSWLA |
| 105 | 3C3 VL1 CDR2 | AASSLQS |
| 106 | 3C3 VL1 CDR3 | QQYNSYPYT |
| 107 | 3C3 VL2 CDR1 | RASQGVSSYLA |
| 108 | 3C3 VL2 CDR2 | DASNRAT |
| 109 | 3C3 VL2 CDR3 | QQRSNWHT |

TABLE 2-continued

Summary table of sequences

| SEQ ID | DESCRIPTION | SEQUENCE |
|---|---|---|
| 110 | 3C3 (VH + G2) or<br>3C3 IgG2 | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKCCVECPPCPAPPVAGPS<br>VFLFPPKPKDTLMISRTPEVTCVVVDVSHEDPEVQFNWYVDGVEVHN<br>AKTKPREEQFNSTFRVVSVLTVVHQDWLNGKEYKCKVSNKGLPAPIE<br>KTISKTKGQPREPQVYTLPPSREEMTKNQVSLTCLVKGFYPSDIAVE<br>WESNGQPENNYKTTPPMLDSDGSFFLYSKLTVDKSRWQQGNVFSCSV<br>MHEALHNHYTQKSLSLSPG |
| 111 | 3C3 (VH + G2(C219S)) or<br>3C3-IgG2-C219S | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKSCVECPPCPAPPVAGPS<br>VFLFPPKPKDTLMISRTPEVTCVVVDVSHEDPEVQFNWYVDGVEVHN<br>AKTKPREEQFNSTFRVVSVLTVVHQDWLNGKEYKCKVSNKGLPAPIE<br>KTISKTKGQPREPQVYTLPPSREEMTKNQVSLTCLVKGFYPSDIAVE<br>WESNGQPENNYKTTPPMLDSDGSFFLYSKLTVDKSRWQQGNVFSCSV<br>MHEALHNHYTQKSLSLSPG |
| 112 | 3C3 (VH + G2.g1) or<br>3C3-IgG2-IgG1 | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKCCVECPPCPAPELLGGP<br>SVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCS<br>VMHEALHNHYTQKSLSLSPG |
| 113 | 3C3 (VH + G2.g1.1) or<br>3C3-IgG2-IgG1.1 | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKCCVECPPCPAPPVAGPS<br>VFLFPPKPKDTLMISRTPEVTCVVVDVSHEDPEVKFNWYVDGVEVHN<br>AKTKPREEQYNSTYRVVSVLTVLHQDWLNGKEYKCKVSNKALPSSIE<br>KTISKAKGQPREPQVYTLPPSREEMTKNQVSLTCLVKGFYPSDIAVE<br>WESNGQPENNYKTTPPVLDSDGSFFLYSKLTVDKSRWQQGNVFSCSV<br>MHEALHNHYTQKSLSLSPG |
| 114 | 3C3 (VH + G2(C219S).g1) or<br>3C3-IgG2-C219S-IgG1 | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKSCVECPPCPAPELLGGP<br>SVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCS<br>VMHEALHNHYTQKSLSLSPG |
| 115 | 3C3 (VH + G2(C219S).g1.1) or<br>3C3-IgG2-C219S-IgG1.1 | QVQLQQWGAGLLKPSETLSLTCAVYGGSFSGYYWTWIRQPPGKGLEW<br>IGKINHSGNTNYNPSLKSRVTISVDTSKNQFSLKLSSVTAADTAVYY<br>CARLGAFDAFDIWGQGTMVTVSSASTKGPSVFPLAPCSRSTSESTAA<br>LGCLVKDYFPEPVTVSWNSGALTSGVHTFPAVLQSSGLYSLSSVVTV<br>PSSNFGTQTYTCNVDHKPSNTKVDKTVERKSCVECPPCPAPPVAGPS<br>VFLFPPKPKDTLMISRTPEVTCVVVDVSHEDPEVKFNWYVDGVEVHN<br>AKTKPREEQYNSTYRVVSVLTVLHQDWLNGKEYKCKVSNKALPSSIE<br>KTISKAKGQPREPQVYTLPPSREEMTKNQVSLTCLVKGFYPSDIAVE<br>WESNGQPENNYKTTPPVLDSDGSFFLYSKLTVDKSRWQQGNVFSCSV<br>MHEALHNHYTQKSLSLSPG |
| 116 | 2G6 (VH) | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSS |
| 117 | 2G6 (VL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIK |

TABLE 2-continued

Summary table of sequences

| SEQ ID | DESCRIPTION | SEQUENCE |
|---|---|---|
| 118 | 2G6 (full length wild-type heavy chain)<br>The constant region is underlined | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPGK |
| 119 | 2G6 (full length wild-type light chain)<br>The constant region is underlined | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 120 | 2G6.IgG1 (VH + IgG1) | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPP<br>CPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG |
| 121 | 2G6.IgG1.1 (VH + IgG1.1) | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPP<br>CPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCK<br>VSNKALPSSIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG |
| 122 | 2G6.IgG1 (VL + CL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 123 | 2G6 VH CDR1 | DYGMH |
| 124 | 2G6 VH CDR2 | VIWYDGSNKFYVDSVKG |
| 125 | 2G6 VH CDR3 | GGRLATGHFYYVMDV |
| 126 | 2G6 VL CDR1 | RASQGISSWLA |
| 127 | 2G6 VL CDR2 | AASSLQS |
| 128 | 2G6 VL CDR3 | QQYNSYPYT |
| 129 | 2G6 (VH + G2) or<br>2G6-IgG2 | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPG |
| 130 | 2G6 (VH + G2(C219S)) or<br>2G6-IgG2-C219S | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKSCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK |

TABLE 2-continued

Summary table of sequences

| SEQ ID | DESCRIPTION | SEQUENCE |
|---|---|---|
| | | GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPG |
| 131 | 2G6 (VH + G2.g1) or<br>2G6-IG2-IgG1 | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSN<br>KALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQ<br>GNVFSCSVMHEALHNHYTQKSLSLSPG |
| 132 | 2G6 (VH + G2.g1.1) or<br>2G6-IgG2-IgG1.1 | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPSSIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 133 | 2G6 (VH + G2(C219S).g1) or<br>2G6-IgG2-C219S-IgG1 | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKSCVECPPCPA<br>PELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSN<br>KALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQ<br>GNVFSCSVMHEALHNHYTQKSLSLSPG |
| 134 | 2G6 (VH + G2(C219S).g1.1) or<br>2G6-IgG2-C219S-IgG1.1 | QVQLVESGGGVVQPGGSLRLSCAASGFILSDYGMHWVRQAPGKGLEW<br>VTVIWYDGSNKFYVDSVKGRFTISRDNSKNTLYLQMNSLRVEDTAVY<br>YCARGGRLATGHFYYVMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKSCVECPPCPA<br>PPVAGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPSSIEKTISKAKGQPREPQVYTLPPSREEMTKNQVSLTCLVKGFY<br>PSDIAVEWESNGQPENNYKTTPPVLDSDGSFFLYSKLTVDKSRWQQG<br>NVFSCSVMHEALHNHYTQKSLSLSPG |
| 135 | 8A6 (VH) | QVQLVESGGGVVQPGRSLRLSCTASGFTFSSYGMQWVRQAPGKGLEW<br>VAVIWYEGSNKYYADSVKGRFTISRENSKNTLYLQMNSLRAEDTAVY<br>YCARGGLMVRGLFYYGMDVWGQGTTVTVSS |
| 136 | 8A6 (VL) | AIQLTQSPSSLSASVGDRVTITCRASQGISSALAWYQQKPGKAPKFL<br>IYDASSLESGVPSRFSGSGSGTDFTLTISSLQPEDFATYYCQQFNSY<br>PYTFGQGTKLEIK |
| 137 | 8A6 (full length wild-type heavy chain)<br>The constant region is underlined | QVQLVESGGGVVQPGRSLRLSCTASGFTFSSYGMQWVRQAPGKGLEW<br>VAVIWYEGSNKYYADSVKGRFTISRENSKNTLYLQMNSLRAEDTAVY<br>YCARGGLMVRGLFYYGMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPGK |
| 138 | 8A6 (full length wild-type light chain)<br>The constant region is underlined | AIQLTQSPSSLSASVGDRVTITCRASQGISSALAWYQQKPGKAPKFL<br>IYDASSLESGVPSRFSGSGSGTDFTLTISSLQPEDFATYYCQQFNSY<br>PYTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 139 | 8A6.IgG1 (VH + IgG1) | QVQLVESGGGVVQPGRSLRLSCTASGFTFSSYGMQWVRQAPGKGLEW<br>VAVIWYEGSNKYYADSVKGRFTISRENSKNTLYLQMNSLRAEDTAVY<br>YCARGGLMVRGLFYYGMDVWGQGTTVTVSSASTKGPSVFPLAPSSKS |

TABLE 2-continued

Summary table of sequences

| SEQ ID | DESCRIPTION | SEQUENCE |
| --- | --- | --- |
| | | TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 140 | 8A6.IgG1.1 (VH + IgG1.1) | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCK VSNKALPSSIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 141 | 8A6.IgG1 (VL + CL) | AIQLTQSPSSLSASVGDRVTITCRASQGISSALAWYQQKPGKAPKFL IYDASSLESGVPSRFSGSGSGTDFTLTISSLQPEDFATYYCQQFNSY PYTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 142 | 8A6 VH CDR1 | SYGMQ |
| 143 | 8A6 VH CDR2 | VIWYEGSNKYYADSVKG |
| 144 | 8A6 VH CDR3 | GGLMVRGLFYYGMDV |
| 145 | 8A6 VL CDR1 | RASQGISSALA |
| 146 | 8A6 VL CDR2 | DASSLES |
| 147 | 8A6 VL CDR3 | QQFNSYPYT |
| 148 | 8A6(VH + G2(C219S)) or 8A6-IgG2-C219S | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVQFNWYV DGVEVHNAKTKPREEQFNSTFRVVSVLTVVHQDWLNGKEYKCKVSNK GLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG |
| 149 | 8A6 (VH + G2.g1) or 8A6-IgG2-IgG1 | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 150 | 8A6 (VH + G2.g1.1) or 8A6-IgG2-IgG1.1 | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 151 | 8A6 (VH + G2(C219S).g1) or 8A6-IgG2-C219S-IgG1 | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PELLGGPSVFLFPPKPKDTLMISRTPEVTCVVVDVSHEDPEVKFNWY |

TABLE 2-continued

Summary table of sequences

| SEQ ID | DESCRIPTION | SEQUENCE |
|---|---|---|
| | | VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 152 | 8A6 (VH + G2(C219S).g1.1) or 8A6-IgG2-C219S-IgG1.1 | QVQLVESGGGVVQPGRSLRLSCTASGFTFSSYGMQWVRQAPGKGLEW VAVIWYEGSNKYYADSVKGRFTISRENSKNTLYLQMNSLRAEDTAVY YCARGGLMVRGLFYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 153 | 9G7 (VH) | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSS |
| 154 | 9G7 (VL1) | EIVLTQSPGTLSLSPGERATLSCRASQSVSSSYLAWYQQKPGQAPRL LIYGASSRATGIPDRFSGSGSGTDFTLTISRLEPEDFAVYYCQQYGS SPWTFGQGTKVEIK |
| 155 | 9G7 (VL2) | EIVLTQSPGTLSLSPGERATLSCRASQSVTSSYLAWYQQKPGQAPRL LIYGASSRATGIPERFSGSGSGTDFTLTISRLEPEDFAVYYCQQYGS SPITFGQGTRLEIK |
| 156 | 9G7 (full length wild-type heavy chain) The constant region is underlined | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSSLGTKTYTCNVDHKPSNTKVDKRVESKYGPPCPSCP APEFLGGPSVFLFPPKPKDTLMISRTPEVTCVVVDVSQEDPEVQFNW YVDGVEVHNAKTKPREEQFNSTYRVVSVLTVLHQDWLNGKEYKCKVS NKGLPSSIEKTISKAKGQPREPQVYTLPPSQEEMTKNQVSLTCLVKG FYPSDIAVEWESNGQPENNYKTTPPVLDSDGSFFLYSRLTVDKSRWQ EGNVFSCSVMHEALHNHYTQKSLSLSLGK |
| 157 | 9G7 L2 (full length wild-type light chain 2) The constant region is underlined | EIVLTQSPGTLSLSPGERATLSCRASQSVTSSYLAWYQQKPGQAPRL LIYGASSRATGIPERFSGSGSGTDFTLTISRLEPEDFAVYYCQQYGS SPITFGQGTRLEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC |
| 158 | 9G7.IgG1 (VH + IgG1) | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPELLGGPSVFLFPPKPKDTLMISRTPEVTCVVVDVSHEDPEVK FNWYVDGVEVHNAKTKPREEQYNSTYRVVSVLTVLHQDWLNGKEYKC KVSNKALPAPIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 159 | 9G7.IgG1.1 (VH + IgG1.1) | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPEAEGAPSVFLFPPKPKDTLMISRTPEVTCVVVDVSHEDPEVK FNWYVDGVEVHNAKTKPREEQYNSTYRVVSVLTVLHQDWLNGKEYKC KVSNKALPSSIEKTISKAKGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG |
| 160 | 9G7.IgG1 (VL1 + CL) | EIVLTQSPGTLSLSPGERATLSCRASQSVSSSYLAWYQQKPGQAPRL LIYGASSRATGIPDRFSGSGSGTDFTLTISRLEPEDFAVYYCQQYGS SPWTFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC |
| 161 | 9G7.IgG1.2 (VL2 + CL) | EIVLTQSPGTLSLSPGERATLSCRASQSVTSSYLAWYQQKPGQAPRL LIYGASSRATGIPERFSGSGSGTDFTLTISRLEPEDFAVYYCQQYGS SPITFGQGTRLEIKRTVAAPSVFIFPPSDEQLKSGTASVVCLLNNFY |

TABLE 2-continued

Summary table of sequences

| SEQ ID | DESCRIPTION | SEQUENCE |
|---|---|---|
| | | PREAKVQWKVDNALQSGNSQESVTEQDSKDSTYSLSSTLTLSKADYE KHKVYACEVTHQGLSSPVTKSFNRGEC |
| 162 | 9G7 VH CDR1 | TVWMS |
| 163 | 9G7 VH CDR2 | RIKSKTDGGTTDYAAPVKG |
| 164 | 9G7 VH CDR3 | GQLIPYSYYYGMDV |
| 165 | 9G7 VL1 CDR1 | RASQSVSSSYLA |
| 166 | 9G7 VL1 CDR2 | GASSRAT |
| 167 | 9G7 VL1 CDR3 | QQYGSSPWT |
| 168 | 9G7 VL2 CDR1 | RASQSVTSSYLA |
| 169 | 9G7 VL2 CDR2 | GASSRAT |
| 170 | 9G7 VL2 CDR3 | QQYGSSPIT |
| 171 | 9G7 (VH + G2) or 9G7-IgG2 | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSNFGTQTYTCNVDHKPSNTKVDKTVERKCCVECPPCP APPVAGPSVFLFPPKPKDTLMISRTPEVTCVVVDVSHEDPEVQFNWY VDGVEVHNAKTKPREEQFNSTFRVVSVLTVVHQDWLNGKEYKCKVSN KGLPAPIEKTISKTKGQPREPQVYTLPPSREEMTKNQVSLTCLVKGF YPSDIAVEWESNGQPENNYKTTPPMLDSDGSFFLYSKLTVDKSRWQQ GNVFSCSVMHEALHNHYTQKSLSLSPG |
| 172 | 9G7 (VH + G2(C219S)) or 9G7-IgG2-C219S | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSNFGTQTYTCNVDHKPSNTKVDKTVERKSCVECPPCP APPVAGPSVFLFPPKPKDTLMISRTPEVTCVVVDVSHEDPEVQFNWY VDGVEVHNAKTKPREEQFNSTFRVVSVLTVVHQDWLNGKEYKCKVSN KGLPAPIEKTISKTKGQPREPQVYTLPPSREEMTKNQVSLTCLVKGF YPSDIAVEWESNGQPENNYKTTPPMLDSDGSFFLYSKLTVDKSRWQQ GNVFSCSVMHEALHNHYTQKSLSLSPG |
| 173 | 9G7 (VH + G2.g1) or 9G7-IgG2-IgG1 | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSNFGTQTYTCNVDHKPSNTKVDKTVERKCCVECPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCKVS NKALPAPIEKTISKAKGQPREPQVYTLPPSREEMTKNQVSLTCLVKG FYPSDIAVEWESNGQPENNYKTTPPVLDSDGSFFLYSKLTVDKSRWQ QGNVFSCSVMHEALHNHYTQKSLSLSPG |
| 174 | 9G7 (VH + G2.g1.1) or 9G7-IgG2-IgG1.1 | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSNFGTQTYTCNVDHKPSNTKVDKTVERKCCVECPPCP APPVAGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPSSIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 175 | 9G7 (VH + G2(C219S).g1) or 9G7-IgG2-C219S-IgG1 | EVQLVESGGGLVKPGGSLRLSCAASGFTFSTVWMSWVRQAPGKGLEW VGRIKSKTDGGTTDYAAPVKGRFTISRDDSKNTLYLQMNSLHTEDTA VYYCTTGQLIPYSYYYGMDVWGQGTSVTVSSASTKGPSVFPLAPCSR STSESTAALGCLVKDYFPEPVTVSWNSGALTSGVHTFPAVLQSSGLY SLSSVVTVPSSNFGTQTYTCNVDHKPSNTKVDKTVERKSCVECPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCKVS NKALPAPIEKTISKAKGQPREPQVYTLPPSREEMTKNQVSLTCLVKG FYPSDIAVEWESNGQPENNYKTTPPVLDSDGSFFLYSKLTVDKSRWQ QGNVFSCSVMHEALHNHYTQKSLSLSPG |

TABLE 2-continued

| Summary table of sequences | | |
|---|---|---|
| SEQ ID | DESCRIPTION | SEQUENCE |
| 176 | 9G7 (VH + G2(C219S).g1.1) or<br>9G7-IgG2-C219S-IgG1.1 | EVQLVESGGGLVKPGGSLRLSCAASGFTFSTVWMSWVRQAPGKGLEW<br>VGRIKSKTDGGTTDYAAPVKGRFTISRDDSKNTLYLQMNSLHTEDTA<br>VYYCTTGQLIPYSYYYGMDVWGQGTSVTVSSASTKGPSVFPLAPCSR<br>STSESTAALGCLVKDYFPEPVTVSWNSGALTSGVHTFPAVLQSSGLY<br>SLSSVVTVPSSNFGTQTYTCNVDHKPSNTKVDKTVERKSCVECPPCP<br>APPVAGPSVFLFPPKPKDTLMISRTPEVTCVVVDVSHEDPEVKFNWY<br>VDGVEVHNAKTKPREEQYNSTYRVVSVLTVLHQDWLNGKEYKCKVSN<br>KALPSSIEKTISKAKGQPREPQVYTLPPSREEMTKNQVSLTCLVKGF<br>YPSDIAVEWESNGQPENNYKTTPPVLDSDGSFFLYSKLTVDKSRWQQ<br>GNVFSCSVMHEALHNHYTQKSLSLSPG |
| 177 | 9G7 L1 (full length wild-type<br>light chain 1)<br>The constant region is<br>underlined | EIVLTQSPGTLSLSPGERATLSCRASQSVSSSYLAWYQQKPGQAPRL<br>LIYGASSRATGIPDRFSGSGSGTDFTLTISRLEPEDFAVYYCQQYGS<br>SPWTFGQGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC |
| 178 | 14E3 (VH) | QVQLQQWGAGLLKPSETLSLTCAVYGGSFSGYYWSWIRQPPGKGLEW<br>IGEINHSGNTYYNPSLKSRVTISVDTSKNQLSLKLSSVTAADTAVYY<br>CARFGSNDAFDIWGQGTMVTVSS |
| 179 | 14E3 (VL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PPTFGQGTKVEIK |
| 180 | 14E3 (full length wild-type<br>heavy chain)<br>The constant region is<br>underlined | QVQLQQWGAGLLKPSETLSLTCAVYGGSFSGYYWSWIRQPPGKGLEW<br>IGEINHSGNTYYNPSLKSRVTISVDTSKNQLSLKLSSVTAADTAVYY<br>CARFGSNDAFDIWGQGTMVTVSSASTKGPSVFPLAPSSKSTSGGTAA<br>LGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGNVF<br>SCSVMHEALHNHYTQKSLSLSPGK |
| 181 | 14E3 (full length wild-type light<br>chain)<br>The constant region is<br>underlined | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PPTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 182 | 14E3.IgG1 (VH + IgG1) | QVQLQQWGAGLLKPSETLSLTCAVYGGSFSGYYWSWIRQPPGKGLEW<br>IGEINHSGNTYYNPSLKSRVTISVDTSKNQLSLKLSSVTAADTAVYY<br>CARFGSNDAFDIWGQGTMVTVSSASTKGPSVFPLAPSSKSTSGGTAA<br>LGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSREEMTKNQVSLTCLVKGFYPSD<br>IAVEWESNGQPENNYKTTPPVLDSDGSFFLYSKLTVDKSRWQQGNVF<br>SCSVMHEALHNHYTQKSLSLSPG |
| 183 | 14E3.IgG1.1 (VH + IgG1.1) | QVQLQQWGAGLLKPSETLSLTCAVYGGSFSGYYWSWIRQPPGKGLEW<br>IGEINHSGNTYYNPSLKSRVTISVDTSKNQLSLKLSSVTAADTAVYY<br>CARFGSNDAFDIWGQGTMVTVSSASTKGPSVFPLAPSSKSTSGGTAA<br>LGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPEAE<br>GAPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>SSIEKTISKAKGQPREPQVYTLPPSREEMTKNQVSLTCLVKGFYPSD<br>IAVEWESNGQPENNYKTTPPVLDSDGSFFLYSKLTVDKSRWQQGNVF<br>SCSVMHEALHNHYTQKSLSLSPG |
| 184 | 14E3.IgG1 (VL + CL) | DIQMTQSPSSLSASVGDRVTITCRASQGISSWLAWYQQKPEKAPKSL<br>IYAASSLQSGVPSRFSGSGSGTDFTLTISSLQPEDFATYYCQQYNSY<br>PPTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 185 | 14E3 VH CDR1 | GYYWS |
| 186 | 14E3 VH CDR2 | EINHSGNTYYNPSLKS |
| 187 | 14E3 VH CDR3 | FGSNDAFDI |

TABLE 2-continued

| Summary table of sequences | | |
|---|---|---|
| SEQ ID | DESCRIPTION | SEQUENCE |
| 188 | 14E3 VL CDR1 | RASQGISSWLA |
| 189 | 14E3 VL CDR2 | AASSLQS |
| 190 | 14E3 VL CDR3 | QQYNSYPPT |
| 191 | 14E3 (VH + G2) or 14E3-IgG2 | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 192 | 14E3 (VH + G2(C219S)) or 14E3-IgG2-C219S | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 193 | 14E3 (VH + G2.g1) or 14E3-IgG2-IgG1 | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 194 | 14E3 (VH + G2.g1.1) or 14E3-IgG2-IgG1.1 | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 195 | 14E3 (VH + G2(C219S).g1) or 14E3-IgG2-C219S-IgG1 | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 196 | 14E3 (VH + G2(C219S).g1.1) or 14E3-IgG2-C219S-IgG1.1 | QVQLQQWGAGLLKPSETLSLTCAVYGGSFSGYYWSWIRQPPGKGLEWIGEINHSGNTYYNPSLKSRVTISVDTSKNQLSLKLSSVTAADTAVYYCARFGSNDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 197 | 19H8 (VH) | QVQLVESGGGVVQPGRSLRLSCAASGFTFSNYGMHWVRQAPGKGLEWMAVIWYGGSNKFYADSVKGRFTISRDNSKNSLSLQMNSLRAEDTAVYYCARGGAMVRGVYYYGMDVWGQGTTVTVSS |

TABLE 2-continued

Summary table of sequences

| SEQ ID | DESCRIPTION | SEQUENCE |
|---|---|---|
| 198 | 19H8 (VL1) | AIQLTQSPSSLSASVGDRVTITCRASQGISSALAWYQQKPGKAPKFL<br>IYDASSLESGVPSRFSGSGSGTDFTLTISSLQPEDFATYYCQQFNSY<br>PQTFGQGTKVEIK |
| 199 | 19H8 (VL2) | EIVLTQSPATLSLSPGERATLSCRASQSVSSYLAWYQQKPGQAPRLL<br>IYDASNRATGIPARFSGSGSGTDFTLTISSLEPEDFAVYYCQQRSNW<br>PLTFGGGTKVEIK |
| 200 | 19H8 (full length wild-type heavy chain) The constant region is underlined | QVQLVESGGGVVQPGRSLRLSCAASGFTFSNYGMHWVRQAPGKGLEW<br>MAVIWYGGSNKFYADSVKGRFTISRDNSKNSLSLQMNSLRAEDTAVY<br>YCARGGAMVRGVYYYGMDVWGQGTTVTVSSASTKGPSVFPLAPCSRS<br>TSESTAALGCLVKDYFPEPVTVSWNSGALTSGVHTFPAVLQSSGLYS<br>LSSVVTVPSSNFGTQTYTCNVDHKPSNTKVDKTVERKCCVECPPCPA<br>PPVAGPSVFLFPPKPKDTLMISRTPEVTCVVVDVSHEDPEVQFNWYV<br>DGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFY<br>PSDIAVEWESNGQPENNYKTTPPMLDSDGSFFLYSKLTVDKSRWQQG<br>NVFSCSVMHEALHNHYTQKSLSLSPGK |
| 201 | 19H8 L1 (full length wild-type light chain 1) The constant region is underlined | AIQLTQSPSSLSASVGDRVTITCRASQGISSALAWYQQKPGKAPKFL<br>IYDASSLESGVPSRFSGSGSGTDFTLTISSLQPEDFATYYCQQFNSY<br>PQTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 202 | 19H8 L2 (full length wild-type light chain 2) | EIVLTQSPATLSLSPGERATLSCRASQSVSSYLAWYQQKPGQAPRLL<br>IYDASNRATGIPARFSGSGSGTDFTLTISSLEPEDFAVYYCQQRSNW<br>PLTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 203 | 19H8.IgG1 (VH + IgG1) | QVQLVESGGGVVQPGRSLRLSCAASGFTFSNYGMHWVRQAPGKGLEW<br>MAVIWYGGSNKFYADSVKGRFTISRDNSKNSLSLQMNSLRAEDTAVY<br>YCARGGAMVRGVYYYGMDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPP<br>CPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG |
| 204 | 19H8.IgG1.1 (VH + IgG1.1) | QVQLVESGGGVVQPGRSLRLSCAASGFTFSNYGMHWVRQAPGKGLEW<br>MAVIWYGGSNKFYADSVKGRFTISRDNSKNSLSLQMNSLRAEDTAVY<br>YCARGGAMVRGVYYYGMDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPP<br>CPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCK<br>VSNKALPSSIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG |
| 205 | 19H8.IgG1 (VL1 + CL) | AIQLTQSPSSLSASVGDRVTITCRASQGISSALAWYQQKPGKAPKFL<br>IYDASSLESGVPSRFSGSGSGTDFTLTISSLQPEDFATYYCQQFNSY<br>PQTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 206 | 19H8.IgG1.2 (VL2 + CL) | EIVLTQSPATLSLSPGERATLSCRASQSVSSYLAWYQQKPGQAPRLL<br>IYDASNRATGIPARFSGSGSGTDFTLTISSLEPEDFAVYYCQQRSNW<br>PLTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 207 | 19H8 VH CDR1 | NYGMH |
| 208 | 19H8 VH CDR2 | VIWYGGSNKFYADSVKG |
| 209 | 19H8 VH CDR3 | GGAMVRGVYYYGMDV |
| 210 | 19H8 VL1 CDR1 | RASQGISSALA |
| 211 | 19H8 VL1 CDR2 | DASSLES |
| 212 | 19H8 VL1 CDR3 | QQFNSYPQT |

TABLE 2-continued

| SEQ ID | DESCRIPTION | SEQUENCE |
|---|---|---|
| | Summary table of sequences | |
| 213 | 19H8 VL2 CDR1 | RASQSVSSYLA |
| 214 | 19H8 VL2 CDR2 | DASNRAT |
| 215 | 19H8 VL2 CDR3 | QQRSNWPLT |
| 216 | 19H8 (VH + G2(C219S)) or 19H8-IgG2-C219S | QVQLVESGGGVVQPGRSLRLSCAASGFTFSNYGMHWVRQAPGKGLEW MAVIWYGGSNKFYADSVKGRFTISRDNSKNSLSLQMNSLRAEDTAVY YCARGGAMVRGVYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVQFNWYV DGVEVHNAKTKPREEQFNSTFRVVSVLTVVHQDWLNGKEYKCKVSNK GLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG |
| 217 | 19H8 (VH + G2.g1) or 19H8-IgG2-IgG1 | QVQLVESGGGVVQPGRSLRLSCAASGFTFSNYGMHWVRQAPGKGLEW MAVIWYGGSNKFYADSVKGRFTISRDNSKNSLSLQMNSLRAEDTAVY YCARGGAMVRGVYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 218 | 19H8 (VH + G2.g1.1) or 19H8-IgG2-IgG1.1 | QVQLVESGGGVVQPGRSLRLSCAASGFTFSNYGMHWVRQAPGKGLEW MAVIWYGGSNKFYADSVKGRFTISRDNSKNSLSLQMNSLRAEDTAVY YCARGGAMVRGVYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 219 | 19H8 (VH + G2(C219S).g1) or 19H8-IgG2-C219S-IgG1 | QVQLVESGGGVVQPGRSLRLSCAASGFTFSNYGMHWVRQAPGKGLEW MAVIWYGGSNKFYADSVKGRFTISRDNSKNSLSLQMNSLRAEDTAVY YCARGGAMVRGVYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 220 | 19H8 (VH + G2(C219S).g1.1) or 19H8-IgG2-C219S-IgG1.1 | QVQLVESGGGVVQPGRSLRLSCAASGFTFSNYGMHWVRQAPGKGLEW MAVIWYGGSNKFYADSVKGRFTISRDNSKNSLSLQMNSLRAEDTAVY YCARGGAMVRGVYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 221 | 6G10.IgG1 (VH + IgG1) | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 222 | 6G10.IgG1.1 (VH + IgG1.1) | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPSSKS |

TABLE 2-continued

| Summary table of sequences | | |
|---|---|---|
| SEQ ID | DESCRIPTION | SEQUENCE |
| | | TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCK VSNKALPSSIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| 223 | 6G10.IgG1 (VL + CL) | AIQLTQSPSSLSASVGDRVTITCRASQGISSALAWYQQKPGKAPKLL IYDASSLESGVPSRFSGSGSGTDFTLTISSLQPEDFATYYCQQFNSY PYTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 224 | 6G10 (VH + G2(C219S)) or 6G10-IgG2-C219S | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVQFNWYV DGVEVHNAKTKPREEQFNSTFRVVSVLTVVHQDWLNGKEYKCKVSNK GLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG |
| 225 | 6G10 (VH + G2.g1) or 6G10-IgG2-IgG1 | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 226 | 6G10 (VH + G2.g1.1) or 6G10-IgG2-IgG1.1 | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKCCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 227 | 6G10 (VH + G2(C219S).g1) or 6G10-IgG2-C219S-IgG1 | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPG |
| 228 | 6G10 (VH + G2(C219S).g1.1) or 6G10-IgG2-C219S-IgG1.1 | QVQLVESGGDVVQPGRSLRLSCAASGFTFSTYGMHWVRQAPGKGLEW VAVTWYAGSNKFYADSVKGRFTISRDNSKNTLYLQMNSLRAEDTAVY YCARGGSMVRGLYYYGMDVWGQGTTVTVSSASTKGPSVFPLAPCSRS TSESTAALGCLVKDYFPEPVTVSWNSGALTSGVHTFPAVLQSSGLYS LSSVVTVPSSNFGTQTYTCNVDHKPSNTKVDKTVERKSCVECPPCPA PPVAGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPSSIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |

Table 2 provides the sequences of the mature variable regions and heavy and light chains and where indicated, sequences with signal peptides.

EQUIVALENTS

Those skilled in the art will recognize, or be able to ascertain using no more than routine experimentation, many equivalents of the specific embodiments disclosed herein. Such equivalents are intended to be encompassed by the following claims

We claim:

1. A chimeric antibody which binds to human glucocorticoid-induced tumor necrosis factor receptor (GITR) and comprises a heavy chain comprising a heavy chain constant region, and a light chain comprising a light chain constant region, wherein the heavy chain comprises heavy chain variable region CDR1, CDR2, and CDR3 comprising the amino acid sequences set forth in SEQ ID NOs: 5-7, respectively, and the light chain comprises light chain variable region CDR1, CDR2, and CDR3 comprising the amino acid sequences set forth in SEQ ID NOs: 8-10, respectively, wherein the heavy chain constant region is a non-human constant region.

2. The antibody of claim 1, wherein the non-human constant region comprises a mouse Fc region.

3. The antibody of claim 2, wherein the mouse Fc region is a mouse IgG2a Fc region.

4. The antibody of claim 1, wherein the antibody comprises the heavy and light chain sequences set forth in SEQ ID NOs: 15 and 16, respectively.

5. The antibody of claim 1, wherein the antibody comprises a detectable moiety.

6. The antibody of claim 5, wherein the detectable moiety is selected from the group consisting of: a radiolabel, a fluorescent label, an enzymatic label, biotin, a chromophore, and an ECL label.

7. The antibody of claim 6, wherein the detectable moiety is a fluorescent label, and wherein the fluorescent label is FITC.

8. A nucleic acid encoding the heavy chain and light chain of the antibody of claim 1.

9. An expression vector comprising the nucleic acid of claim 8.

10. A host cell comprising the expression vector of claim 9.

11. The antibody of claim 4, wherein the antibody comprises a detectable moiety.

12. The antibody of claim 11, wherein the detectable moiety is selected from the group consisting of: a radiolabel, a fluorescent label, an enzymatic label, biotin, a chromophore, and an ECL label.

13. A nucleic acid encoding the heavy chain and light chain of the antibody of claim 4.

14. An expression vector comprising the nucleic acid of claim 13.

15. A host cell comprising the expression vector of claim 14.

16. A method for determining the level of expression of glucocorticoid-induced tumor necrosis factor receptor (GITR) on tumor infiltrating lymphocytes (TILs) and/or tumor cells in a human tissue sample, comprising:

(a) contacting a tissue sample from a patient with cancer with the antibody of claim 1, (b) detecting the binding of the antibody to GITR on TILs and/or tumor cells of the tissue sample, and optionally (c) staining the tissue sample with markers of TILs and/or tumor cells, and/or with hematoxylin and eosin, to identify the TILs and/or tumor cells that were identified as GITR positive in step (b).

17. A method of detecting human glucocorticoid-induced tumor necrosis factor receptor (GITR) in a human biological sample comprising:

(a) contacting the sample with the antibody of claim 1, and (b) detecting the binding of the antibody to GITR in the sample.

18. A method of identifying a cancer patient likely to respond to an anti-GITR immunotherapy comprising:

(a) contacting a tumor sample from the patient with the antibody of claim 1, (b) detecting the binding of the antibody to GITR in the tumor sample, and (c) determining the level of GITR protein expression in the sample, wherein a level of GITR protein above a threshold level indicates that the tumor is a GITR-positive tumor and that the patient is likely to or predicted to respond to anti-GITR immunotherapy.

19. A method of treating a cancer patient comprising:

(a) determining whether the patient has a GITR-positive tumor according to the method of claim 17; and (b) administering to the patient an agent that modulates GITR signaling if the patient is determined to have a GITR-positive tumor.

20. A method of monitoring a glucocorticoid-induced tumor necrosis factor receptor (GITR)-positive tumor in a cancer patient comprising:

(a) detecting GITR protein expression in the GITR-positive tumor at a first time point by using the antibody of claim 1, (b) determining the level of GITR protein expression at the first time point, (c) detecting GITR protein expression in the tumor at a second time point using the same antibody used in step (a), (d) determining the level of GITR protein expression in the tumor from the second time point, and (e) comparing the levels of GITR protein expression determined at the first and second time points, wherein a higher level at the first time point relative to the second time point is indicative of tumor regression, a lower level at the first time point relative to the second time point is indicative of tumor progression, and a relatively unchanged level at the first time point relative to the second time point is indicative of a stable tumor.

* * * * *